United States Patent
Creighton

(10) Patent No.: US 10,813,997 B2
(45) Date of Patent: *Oct. 27, 2020

(54) DEVICES FOR CONTROLLING MAGNETIC NANOPARTICLES TO TREAT FLUID OBSTRUCTIONS

(71) Applicant: Pulse Therapeutics, Inc., St. Louis, MO (US)

(72) Inventor: Francis M. Creighton, Richmond Heights, MO (US)

(73) Assignee: Pulse Therapeutics, Inc., St. Louis, MO (US)

(*) Notice: Subject to any disclaimer, the term of this patent is extended or adjusted under 35 U.S.C. 154(b) by 31 days.

This patent is subject to a terminal disclaimer.

(21) Appl. No.: 16/032,796

(22) Filed: Jul. 11, 2018

(65) Prior Publication Data

US 2019/0038748 A1 Feb. 7, 2019

Related U.S. Application Data

(63) Continuation of application No. 15/155,386, filed on May 16, 2016, now Pat. No. 10,029,008, which is a (Continued)

(51) Int. Cl.
*A61K 41/00* (2020.01)
*A61B 34/00* (2016.01)
(Continued)

(52) U.S. Cl.
CPC .............. *A61K 41/00* (2013.01); *A61B 17/22* (2013.01); *A61B 17/22012* (2013.01);
(Continued)

(58) Field of Classification Search
CPC . H01F 7/0273; A61B 17/22; A61B 17/22012; A61B 2017/00876;
(Continued)

(56) References Cited

U.S. PATENT DOCUMENTS 3,474,777 A 10/1969 Figge et al.
4,141,687 A 2/1979 Forrest et al.
(Continued)

FOREIGN PATENT DOCUMENTS

DE 2450098 A1 4/1976
DE 102005030986 1/2007
(Continued)

OTHER PUBLICATIONS

Chen, Haitao, et al., "Capture of magnetic carriers within large arteries using external magnetic fields," Journal of Drug Targeting, May 2006, 16:4,262-268.
(Continued)

*Primary Examiner* — Navin Natnithithadha
*Assistant Examiner* — Sunita Reddy
(74) *Attorney, Agent, or Firm* — Knobbe, Martens, Olson & Bear, LLP

(57) ABSTRACT

A system for the physical manipulation of free magnetic rotors in a circulatory system using a remotely placed magnetic field-generating stator is provided. In one embodiment, the invention relates to the control of magnetic particles in a fluid medium using permanent magnet-based or electromagnetic field-generating stator sources. Such a system can be useful for increasing the diffusion of therapeutic agents in a fluid medium, such as a human circulatory system, which can result in substantial clearance of fluid obstructions, such as vascular occlusions, in a circulatory system resulting in increased blood flow. Examples of vascular occlusions targeted by the system include, but are not limited to, atherosclerotic plaques, including fibrous caps, fatty buildup, coronary occlusions, arterial stenosis, restenosis, vein thrombi, arterial thrombi, cerebral thrombi, embolisms, hemorrhages, other blood clots, and very small vessels.

20 Claims, 38 Drawing Sheets

Related U.S. Application Data continuation of application No. 14/268,244, filed on May 2, 2014, now Pat. No. 9,339,664, which is a continuation of application No. 13/505,447, filed as application No. PCT/US2010/055133 on Nov. 2, 2010, now Pat. No. 8,715,150.

(60) Provisional application No. 61/280,321, filed on Nov. 2, 2009.

(51) Int. Cl.

| | | |
|---|---|---|
| *A61K 47/69* | (2017.01) | |
| *A61B 17/22* | (2006.01) | |
| *A61K 9/00* | (2006.01) | |
| *A61N 2/06* | (2006.01) | |
| *A61N 2/02* | (2006.01) | |
| *A61N 2/00* | (2006.01) | |
| *A61K 38/48* | (2006.01) | |
| *H01F 7/02* | (2006.01) | |
| *B82Y 5/00* | (2011.01) | |
| *A61B 17/00* | (2006.01) | |

(52) U.S. Cl.
CPC ............ *A61B 34/73* (2016.02); *A61K 9/0019* (2013.01); *A61K 38/482* (2013.01); *A61K 38/484* (2013.01); *A61K 47/6941* (2017.08); *A61N 2/004* (2013.01); *A61N 2/02* (2013.01); *A61N 2/06* (2013.01); *C12Y 304/21007* (2013.01); *C12Y 304/21068* (2013.01); *H01F 7/0273* (2013.01); *A61B 2017/00876* (2013.01); *A61B 2017/22084* (2013.01); *A61B 2017/22094* (2013.01); *A61B 2034/733* (2016.02); *B82Y 5/00* (2013.01); *Y10S 977/811* (2013.01); *Y10S 977/905* (2013.01); *Y10S 977/909* (2013.01)

(58) Field of Classification Search
CPC .......... A61B 2017/22084; A61B 34/73; A61B 2034/733; A61N 2/004; A61N 2/02; A61N 2/06; B82Y 5/00; Y10S 977/811; Y10S 977/905; Y10S 977/909; C12Y 304/21007; C12Y 304/21068; A61K 41/00; A61K 47/6941; A61K 38/484; A61K 38/482; A61K 9/0019
USPC ....... 977/700, 737, 745, 773, 786, 833, 838, 977/839, 900–902, 904–906, 908, 915, 977/959, 963; 600/407, 427, 9, 12, 13, 600/114, 117, 118, 424; 607/1; 128/897–899; 424/489; 606/159; 335/300

See application file for complete search history.

(56) References Cited

U.S. PATENT DOCUMENTS

| | | | |
|---|---|---|---|
| 4,359,453 A | 11/1982 | Gordon | |
| 4,916,070 A | 4/1990 | Matsueda et al. | |
| 5,078,140 A | 1/1992 | Kwoh | |
| 5,110,727 A | 5/1992 | Oberhardt | |
| 5,401,253 A | 3/1995 | Reynolds | |
| 5,543,158 A | 8/1996 | Gref et al. | |
| 5,654,864 A | 8/1997 | Ritter et al. | |
| 5,665,277 A | 9/1997 | Johnson et al. | |
| 5,916,539 A | 6/1999 | Pilgrimm | |
| 5,931,818 A | 8/1999 | Werp et al. | |
| 6,014,580 A | 1/2000 | Blume et al. | |
| 6,015,414 A | 1/2000 | Werp et al. | |
| 6,128,174 A | 10/2000 | Ritter et al. | |
| 6,148,823 A | 11/2000 | Hastings | |
| 6,152,933 A | 11/2000 | Werp et al. | |
| 6,157,853 A | 12/2000 | Blume et al. | |
| 6,212,419 B1 | 4/2001 | Blume et al. | |
| 6,231,496 B1 | 5/2001 | Wilk et al. | |
| 6,241,671 B1 | 6/2001 | Ritter et al. | |
| 6,292,678 B1 | 9/2001 | Hall et al. | |
| 6,296,604 B1 | 10/2001 | Garibaldi et al. | |
| 6,304,768 B1 | 10/2001 | Blume et al. | |
| 6,311,082 B1 | 10/2001 | Creighton, IV et al. | |
| 6,315,709 B1 | 11/2001 | Garibaldi et al. | |
| 6,330,467 B1 | 12/2001 | Creighton, IV et al. | |
| 6,352,363 B1 | 3/2002 | Munger et al. | |
| 6,358,244 B1 | 3/2002 | Newman et al. | |
| 6,364,823 B1 | 4/2002 | Garibaldi et al. | |
| 6,375,606 B1 | 4/2002 | Garibaldi et al. | |
| 6,385,472 B1 | 5/2002 | Hall et al. | |
| 6,401,723 B1 | 6/2002 | Garibaldi et al. | |
| 6,428,551 B1 | 8/2002 | Hall et al. | |
| 6,459,924 B1 | 10/2002 | Creighton, IV et al. | |
| 6,475,223 B1 | 11/2002 | Werp et al. | |
| 6,482,436 B1 | 11/2002 | Volkonsky et al. | |
| 6,505,062 B1 | 1/2003 | Ritter et al. | |
| 6,507,751 B2 | 1/2003 | Blume et al. | |
| 6,522,909 B1 | 2/2003 | Garibaldi et al. | |
| 6,524,303 B1 | 2/2003 | Garibaldi | |
| 6,527,782 B2 | 3/2003 | Hogg et al. | |
| 6,529,761 B2 | 3/2003 | Creighton, IV et al. | |
| 6,537,196 B1 | 3/2003 | Creighton, IV et al. | |
| 6,541,039 B1 | 4/2003 | Lesniak et al. | |
| 6,542,766 B2 | 4/2003 | Hall et al. | |
| 6,562,019 B1 | 5/2003 | Sell | |
| 6,630,879 B1 | 10/2003 | Creighton, IV et al. | |
| 6,638,494 B1 | 10/2003 | Pilgrimm | |
| 6,662,034 B2 | 12/2003 | Segner et al. | |
| 6,677,752 B1 | 1/2004 | Creighton, IV et al. | |
| 6,702,804 B1 | 3/2004 | Ritter et al. | |
| 6,733,511 B2 | 5/2004 | Hall et al. | |
| 6,740,103 B2 | 5/2004 | Hall et al. | |
| 6,755,816 B2 | 6/2004 | Ritter et al. | |
| 6,786,219 B2 | 9/2004 | Garibaldi et al. | |
| 6,817,364 B2 | 11/2004 | Garibaldi et al. | |
| 6,834,201 B2 | 12/2004 | Gillies et al. | |
| 6,902,528 B1 | 6/2005 | Garibaldi et al. | |
| 6,911,026 B1 | 6/2005 | Hall et al. | |
| 6,940,379 B2 | 9/2005 | Creighton | |
| 6,968,846 B2 | 11/2005 | Viswanathan | |
| 6,975,197 B2 | 12/2005 | Creighton, IV | |
| 6,979,466 B2 | 12/2005 | Lesniak et al. | |
| 6,980,843 B2 | 12/2005 | Eng et al. | |
| 7,008,418 B2 | 3/2006 | Hall et al. | |
| 7,010,338 B2 | 3/2006 | Ritter et al. | |
| 7,017,584 B2 | 3/2006 | Garibaldi et al. | |
| 7,019,610 B2 | 3/2006 | Creighton, IV et al. | |
| 7,020,512 B2 | 3/2006 | Ritter et al. | |
| 7,052,777 B2 | 5/2006 | Brotzman, Jr. et al. | |
| 7,066,924 B1 | 6/2006 | Garibaldi et al. | |
| 7,074,175 B2 | 7/2006 | Handy et al. | |
| 7,137,976 B2 | 11/2006 | Ritter et al. | |
| 7,161,453 B2 | 1/2007 | Creighton, IV | |
| 7,189,198 B2 | 3/2007 | Harburn et al. | |
| 7,190,819 B2 | 3/2007 | Viswanathan | |
| 7,211,082 B2 | 5/2007 | Hall et al. | |
| 7,248,914 B2 | 7/2007 | Hastings et al. | |
| 7,249,604 B1 | 7/2007 | Mohanraj | |
| 7,264,584 B2 | 9/2007 | Ritter et al. | |
| 7,276,044 B2 | 10/2007 | Ferry et al. | |
| 7,286,034 B2 | 10/2007 | Creighton | |
| 7,305,263 B2 | 12/2007 | Creighton, IV | |
| 7,313,429 B2 | 12/2007 | Creighton, IV et al. | |
| 7,329,638 B2 | 2/2008 | Yang et al. | |
| 7,341,063 B2 | 3/2008 | Garbibaldi et al. | |
| 7,346,379 B2 | 3/2008 | Eng et al. | |
| 7,389,778 B2 | 6/2008 | Sabo et al. | |
| 7,416,335 B2 | 8/2008 | Munger | |
| 7,459,145 B2 | 12/2008 | Bao et al. | |
| 7,495,537 B2 | 2/2009 | Tunay | |
| 7,502,640 B2 | 3/2009 | Conolly et al. | |
| 7,505,615 B2 | 3/2009 | Viswanathan | |
| 7,516,416 B2 | 4/2009 | Viswanathan et al. | |

(56) References Cited

U.S. PATENT DOCUMENTS

| | | |
|---|---|---|
| 7,524,630 B2 | 4/2009 | Tan et al. |
| 7,537,570 B2 | 5/2009 | Kastelein |
| 7,540,288 B2 | 6/2009 | Viswanathan et al. |
| 7,540,866 B2 | 6/2009 | Viswanathan et al. |
| 7,543,239 B2 | 6/2009 | Viswanathan et al. |
| 7,555,331 B2 | 6/2009 | Viswanathan |
| 7,567,233 B2 | 7/2009 | Garibaldi et al. |
| 7,603,905 B2 | 10/2009 | Creighton, IV |
| 7,623,736 B2 | 11/2009 | Viswanathan |
| 7,625,382 B2 | 12/2009 | Werp et al. |
| 7,627,361 B2 | 12/2009 | Viswanathan |
| 7,630,752 B2 | 12/2009 | Viswanathan |
| 7,635,342 B2 | 12/2009 | Ferry et al. |
| 7,657,075 B2 | 2/2010 | Viswanathan |
| 7,662,126 B2 | 2/2010 | Creighton, IV |
| 7,690,619 B2 | 4/2010 | Wolfersberger |
| 7,708,696 B2 | 5/2010 | Ritter et al. |
| 7,713,239 B2 | 5/2010 | Uber, III et al. |
| 7,742,803 B2 | 6/2010 | Viswanathan et al. |
| 7,747,960 B2 | 6/2010 | Garibaldi et al. |
| 7,766,856 B2 | 6/2010 | Ferry et al. |
| 7,751,867 B2 | 7/2010 | Viswanathan |
| 7,756,308 B2 | 7/2010 | Viswanathan |
| 7,757,694 B2 | 7/2010 | Ritter et al. |
| 7,761,133 B2 | 7/2010 | Viswanathan et al. |
| 7,769,428 B2 | 8/2010 | Viswanathan et al. |
| 7,769,444 B2 | 8/2010 | Pappone |
| 7,771,415 B2 | 8/2010 | Ritter et al. |
| 7,771,437 B2 | 8/2010 | Hogg et al. |
| 7,772,950 B2 | 8/2010 | Tunay |
| 7,774,046 B2 | 8/2010 | Werp et al. |
| 7,815,580 B2 | 10/2010 | Viswanathan |
| 7,818,076 B2 | 10/2010 | Viswanathan |
| 7,831,294 B2 | 11/2010 | Viswanathan |
| 7,846,201 B2 | 12/2010 | Chorny et al. |
| 7,853,306 B2 | 12/2010 | Viswanathan et al. |
| 7,892,233 B2 | 2/2011 | Hall et al. |
| 7,961,924 B2 | 6/2011 | Viswanathan |
| 7,961,926 B2 | 6/2011 | Viswanathan |
| 7,966,059 B2 | 6/2011 | Creighton, IV et al. |
| 7,968,117 B1 | 6/2011 | Morrison et al. |
| 7,983,733 B2 | 7/2011 | Viswanathan |
| 7,998,020 B2 | 8/2011 | Kidd et al. |
| 8,024,024 B2 | 9/2011 | Viswanathan et al. |
| 8,060,184 B2 | 11/2011 | Hastings et al. |
| 8,088,129 B2 | 1/2012 | Werp et al. |
| 8,092,450 B2 | 1/2012 | Davies et al. |
| 8,114,032 B2 | 2/2012 | Ferry et al. |
| 8,135,185 B2 | 3/2012 | Blume et al. |
| 8,162,920 B2 | 4/2012 | Ritter et al. |
| 8,192,374 B2 | 6/2012 | Viswanathan |
| 8,196,590 B2 | 6/2012 | Sabo et al. |
| 8,246,975 B2 | 8/2012 | Eguchi et al. |
| 8,251,885 B2 | 8/2012 | Ueda et al. |
| 8,278,274 B2 | 10/2012 | Bussat et al. |
| 8,293,213 B2 | 10/2012 | Schwartz et al. |
| 8,308,628 B2 | 11/2012 | Creighton |
| 8,313,422 B2 | 11/2012 | Creighton |
| 8,369,934 B2 | 2/2013 | Viswanathan |
| 8,500,619 B2 | 8/2013 | Brown et al. |
| 8,529,428 B2 | 9/2013 | Creighton |
| 8,562,505 B2 | 10/2013 | Levy et al. |
| 8,568,286 B2 | 10/2013 | Sih et al. |
| 8,579,787 B2 | 11/2013 | Shapiro et al. |
| 8,689,800 B2 | 4/2014 | Lin et al. |
| 8,691,261 B2 | 4/2014 | Eguchi et al. |
| 8,715,150 B2 | 5/2014 | Creighton |
| 8,888,674 B2 | 11/2014 | Shapiro et al. |
| 8,897,856 B2 | 11/2014 | Gaitas |
| 8,926,491 B2 | 1/2015 | Creighton |
| 8,968,699 B2 | 3/2015 | Jin et al. |
| 9,028,829 B2 | 5/2015 | Levy et al. |
| 9,108,035 B2 | 8/2015 | Shapiro et al. |
| 9,138,293 B1 | 9/2015 | Weisman |
| 9,339,664 B2 | 5/2016 | Creighton |
| 9,345,498 B2 | 5/2016 | Creighton |
| 9,883,878 B2 | 2/2018 | Creighton et al. |
| 10,029,008 B2 | 7/2018 | Creighton |
| 10,159,734 B2 | 12/2018 | Creighton |
| 10,646,241 B2 | 5/2020 | Creighton et al. |
| 2001/0038683 A1 | 11/2001 | Ritter et al. |
| 2002/0019644 A1 | 2/2002 | Hastings et al. |
| 2002/0072662 A1 | 6/2002 | Hall et al. |
| 2002/0100486 A1 | 8/2002 | Creighton et al. |
| 2002/0103426 A1 | 8/2002 | Segner et al. |
| 2002/0103430 A1 | 8/2002 | Hastings et al. |
| 2002/0115904 A1 | 8/2002 | Ren |
| 2003/0009094 A1 | 1/2003 | Segner et al. |
| 2003/0028071 A1* | 2/2003 | Handy .............. A61N 1/406 600/12 |
| 2003/0032995 A1* | 2/2003 | Handy .............. A61N 1/406 607/103 |
| 2003/0086867 A1 | 5/2003 | Lanza et al. |
| 2003/0105382 A1 | 6/2003 | Brown et al. |
| 2003/0181809 A1 | 9/2003 | Hall et al. |
| 2003/0220667 A1 | 11/2003 | Van Der Burg |
| 2004/0002654 A1 | 1/2004 | Davidson et al. |
| 2004/0006301 A1 | 1/2004 | Sell et al. |
| 2004/0006350 A1 | 1/2004 | Hogg et al. |
| 2004/0064153 A1 | 4/2004 | Creighton et al. |
| 2004/0077942 A1 | 4/2004 | Hall et al. |
| 2004/0096511 A1 | 5/2004 | Harburn et al. |
| 2004/0133118 A1 | 7/2004 | Llinas |
| 2004/0133130 A1 | 7/2004 | Ferry et al. |
| 2004/0147829 A1 | 7/2004 | Segner et al. |
| 2004/0157082 A1 | 8/2004 | Ritter et al. |
| 2004/0186376 A1 | 9/2004 | Hogg et al. |
| 2004/0196127 A1 | 10/2004 | Perrin |
| 2004/0253183 A1 | 12/2004 | Uber, III et al. |
| 2004/0254419 A1 | 12/2004 | Wang et al. |
| 2004/0260172 A1 | 12/2004 | Ritter et al. |
| 2004/0267106 A1 | 12/2004 | Segner et al. |
| 2005/0004585 A1 | 1/2005 | Hall et al. |
| 2005/0020911 A1 | 1/2005 | Viswanathan et al. |
| 2005/0021063 A1 | 1/2005 | Hall et al. |
| 2005/0025797 A1 | 2/2005 | Wang et al. |
| 2005/0033162 A1 | 2/2005 | Garibaldi et al. |
| 2005/0065435 A1 | 3/2005 | Rauch et al. |
| 2005/0079132 A1 | 4/2005 | Wang et al. |
| 2005/0090732 A1* | 4/2005 | Ivkov .............. A61N 1/406 600/411 |
| 2005/0113628 A1 | 5/2005 | Creighton et al. |
| 2005/0113812 A1 | 5/2005 | Viswanathan et al. |
| 2005/0119556 A1 | 6/2005 | Gillies et al. |
| 2005/0119687 A1 | 6/2005 | Dacey et al. |
| 2005/0182315 A1 | 8/2005 | Ritter et al. |
| 2005/0256398 A1 | 11/2005 | Hastings et al. |
| 2005/0271732 A1 | 12/2005 | Seeney et al. |
| 2005/0271745 A1* | 12/2005 | Gruettner .............. A61K 33/26 424/646 |
| 2005/0273130 A1 | 12/2005 | Sell |
| 2005/0281858 A1* | 12/2005 | Kloke .............. A61L 27/34 424/423 |
| 2006/0025675 A1 | 2/2006 | Viswanathan et al. |
| 2006/0025679 A1 | 2/2006 | Viswanathan et al. |
| 2006/0025719 A1 | 2/2006 | Viswanathan et al. |
| 2006/0036163 A1 | 2/2006 | Viswanathan |
| 2006/0041181 A1 | 2/2006 | Viswanathan et al. |
| 2006/0094956 A1 | 5/2006 | Viswanathan |
| 2006/0142630 A1 | 6/2006 | Meretei |
| 2006/0142632 A1 | 6/2006 | Meretei |
| 2006/0142749 A1* | 6/2006 | Ivkov .............. A61K 41/0052 606/27 |
| 2006/0144407 A1 | 7/2006 | Aliberto et al. |
| 2006/0144408 A1 | 7/2006 | Ferry |
| 2006/0165805 A1 | 7/2006 | Steinhoff et al. |
| 2006/0228421 A1 | 10/2006 | Seeney et al. |
| 2006/0270948 A1 | 11/2006 | Viswanathan et al. |
| 2006/0276867 A1 | 12/2006 | Viswanathan |
| 2006/0278248 A1 | 12/2006 | Viswanathan |
| 2006/0281990 A1 | 12/2006 | Viswanathan et al. |
| 2007/0010702 A1 | 1/2007 | Wang et al. |
| 2007/0016010 A1 | 1/2007 | Creighton et al. |
| 2007/0016131 A1 | 1/2007 | Munger et al. |

(56) References Cited

U.S. PATENT DOCUMENTS

| | | |
|---|---|---|
| 2007/0021731 A1 | 1/2007 | Garibaldi et al. |
| 2007/0021744 A1 | 1/2007 | Creighton |
| 2007/0032746 A1 | 2/2007 | Sell |
| 2007/0038065 A1 | 2/2007 | Creighton et al. |
| 2007/0038074 A1 | 2/2007 | Ritter et al. |
| 2007/0040670 A1 | 2/2007 | Viswanathan |
| 2007/0043455 A1 | 2/2007 | Viswanathan et al. |
| 2007/0049909 A1 | 3/2007 | Munger |
| 2007/0055124 A1 | 3/2007 | Viswanathan et al. |
| 2007/0062546 A1 | 3/2007 | Viswanathan et al. |
| 2007/0135804 A1 | 6/2007 | Ritter et al. |
| 2007/0148634 A1 | 6/2007 | Bruchez et al. |
| 2007/0149946 A1 | 6/2007 | Viswanathan et al. |
| 2007/0167720 A1 | 7/2007 | Viswanathan et al. |
| 2007/0191671 A1 | 8/2007 | Kawano et al. |
| 2007/0197899 A1 | 8/2007 | Ritter et al. |
| 2007/0197906 A1 | 8/2007 | Ritter |
| 2007/0225589 A1 | 9/2007 | Viswanathan |
| 2007/0231393 A1 | 10/2007 | Ritter et al. |
| 2007/0250041 A1 | 10/2007 | Werp |
| 2007/0270686 A1 | 11/2007 | Ritter et al. |
| 2007/0287909 A1 | 12/2007 | Garibaldi et al. |
| 2008/0004595 A1 | 1/2008 | Viswanathan et al. |
| 2008/0006280 A1 | 1/2008 | Aliberto et al. |
| 2008/0015427 A1 | 1/2008 | Kastelein et al. |
| 2008/0016677 A1 | 1/2008 | Creighton |
| 2008/0039705 A1 | 2/2008 | Viswanathan |
| 2008/0039830 A1 | 2/2008 | Munger et al. |
| 2008/0045865 A1 | 2/2008 | Kislev |
| 2008/0047568 A1 | 2/2008 | Ritter et al. |
| 2008/0058608 A1 | 3/2008 | Garibaldi et al. |
| 2008/0058609 A1 | 3/2008 | Garibaldi et al. |
| 2008/0059598 A1 | 3/2008 | Garibaldi et al. |
| 2008/0064933 A1 | 3/2008 | Garibaldi et al. |
| 2008/0065061 A1 | 3/2008 | Viswanathan |
| 2008/0092993 A1 | 4/2008 | Creighton |
| 2008/0097200 A1 | 4/2008 | Blume et al. |
| 2008/0114335 A1 | 5/2008 | Flickinger et al. |
| 2008/0200913 A1 | 8/2008 | Viswanathan |
| 2008/0208912 A1 | 8/2008 | Garibaldi |
| 2008/0228065 A1 | 9/2008 | Viswanathan et al. |
| 2008/0228068 A1 | 9/2008 | Viswanathan et al. |
| 2008/0287909 A1 | 11/2008 | Viswanathan et al. |
| 2008/0294232 A1 | 11/2008 | Viswanathan |
| 2008/0312673 A1 | 12/2008 | Viswanathan et al. |
| 2009/0012821 A1 | 1/2009 | Besson et al. |
| 2009/0062646 A1 | 3/2009 | Creighton, IV et al. |
| 2009/0062828 A1 | 3/2009 | Marr |
| 2009/0082722 A1 | 3/2009 | Munger et al. |
| 2009/0105579 A1 | 4/2009 | Garibaldi |
| 2009/0131798 A1 | 5/2009 | Minar et al. |
| 2009/0131927 A1 | 5/2009 | Kastelein et al. |
| 2009/0138009 A1 | 5/2009 | Viswanathan et al. |
| 2009/0148387 A1* | 6/2009 | Bikram .................. A61K 33/24 424/9.322 |
| 2009/0177032 A1 | 7/2009 | Garibaldi et al. |
| 2009/0285759 A1 | 11/2009 | Ishikawa et al. |
| 2009/0287036 A1 | 11/2009 | Shapiro et al. |
| 2009/0299127 A1 | 12/2009 | Rudolph et al. |
| 2009/0306643 A1 | 12/2009 | Pappone et al. |
| 2010/0003197 A1* | 1/2010 | Bikram .................. A61K 33/24 424/9.323 |
| 2010/0055042 A1 | 3/2010 | Yathindranath et al. |
| 2010/0063385 A1 | 3/2010 | Garibaldi et al. |
| 2010/0069733 A1 | 3/2010 | Kastelein et al. |
| 2010/0097315 A1 | 4/2010 | Garibaldi et al. |
| 2010/0137706 A1 | 6/2010 | Viswanathan |
| 2010/0163061 A1 | 7/2010 | Creighton |
| 2010/0168553 A1 | 7/2010 | Martel |
| 2010/0204674 A1* | 8/2010 | Forbes ..................... A61F 2/82 604/500 |
| 2010/0222669 A1 | 9/2010 | Flickinger et al. |
| 2010/0233147 A1 | 9/2010 | Schwartz et al. |
| 2010/0269838 A1 | 10/2010 | Flanagan et al. |
| 2010/0298845 A1 | 11/2010 | Kidd et al. |
| 2011/0021970 A1 | 1/2011 | Vo-Dinh et al. |
| 2011/0022029 A1 | 1/2011 | Viswanathan |
| 2011/0028989 A1 | 2/2011 | Ritter et al. |
| 2011/0046618 A1 | 2/2011 | Minar et al. |
| 2011/0071335 A1 | 3/2011 | Ueda et al. |
| 2011/0087237 A1 | 4/2011 | Viswanathan |
| 2011/0130718 A1 | 6/2011 | Kidd et al. |
| 2011/0152712 A1 | 6/2011 | Cao et al. |
| 2011/0215888 A1 | 9/2011 | Abbott et al. |
| 2011/0245581 A1 | 10/2011 | Schwartz et al. |
| 2012/0021010 A1 | 1/2012 | Deb et al. |
| 2012/0157824 A1* | 6/2012 | Bossmann ............... C12Q 1/37 600/420 |
| 2013/0023714 A1 | 1/2013 | Johnston et al. |
| 2013/0296631 A1 | 11/2013 | Johnston et al. |
| 2014/0163367 A1 | 6/2014 | Eskuri |
| 2014/0248632 A1 | 9/2014 | Kopelman et al. |
| 2015/0231282 A1 | 8/2015 | Pozzo et al. |
| 2015/0366574 A1 | 12/2015 | Kovarik et al. |
| 2017/0165020 A1 | 6/2017 | Martel |
| 2018/0221041 A1 | 8/2018 | Creighton et al. |
| 2019/0255174 A1 | 8/2019 | Creighton |
| 2019/0336231 A1 | 11/2019 | Kidd et al. |
| 2020/0085730 A1 | 3/2020 | Khizroev et al. |

FOREIGN PATENT DOCUMENTS

| | | |
|---|---|---|
| EP | 1001811 | 9/2002 |
| JP | H07-213622 | 8/1995 |
| WO | WO 89/10788 | 11/1989 |
| WO | WO 2003/022360 | 3/2003 |
| WO | WO 2004/083902 A2 | 9/2004 |
| WO | WO 2005/011810 | 2/2005 |
| WO | WO 2005/072169 | 8/2005 |
| WO | WO 2006/035550 | 4/2006 |
| WO | WO 2007/125699 | 11/2007 |
| WO | WO 2010/092495 | 8/2010 |
| WO | WO 2011/047313 | 4/2011 |
| WO | WO 2011/050085 | 4/2011 |
| WO | WO 2012/009675 | 1/2012 |
| WO | WO 2012/018290 | 2/2012 |

OTHER PUBLICATIONS

Peasley, K.W., "Destruction of Human Immunodeficiency-Infected Cells by Ferrofluid Particles Manipulated by an External Magnetic Field: Mechanical Disruption and Selective Introduction of Cytotoxic or Antiretroviral Substances into Target Cells," Medical Hypothesis, Jan. 1996, pp. 5-12, vol. 46, Issue 1.

Califf, Robert M. et al., "Hemorrhagic complications associated with the use of intravenous tissue plasminogen activator in treatment of acute myocardial infarction," The American Journal of Medicine, Sep. 1988, pp. 353-359, vol. 85, Issue 3.

Leadley, Robert J. Jr., et al., "Contribution of in vivo models of thrombosis to the discovery and development of novel antithrombotic agents," Journal of Pharmacological and Toxicological Methods, Mar.-Apr. 2000, pp. 101-116, vol. 43, Issue 2.

Pouliquen, D. et. al., "Iron oxide nanoparticles for use as an MRI contrast agent: pharmacokinetics and metabolism," Magnetic Resonance Imaging, 1991, pp. 275-283, vol. 9, Issue 3.

Sugimoto, Tadao, Egoa Matijevic, "Formation of Uniform Spherical Magnetite Particles by Crystallization from Ferrous Hydroxide Gels," Journal of Colloid and Interface Science, Mar. 1980, pp. 227-243. vol. 74, Issue 1.

Wu, Sau-Ching, et al., "Functional Production and Characterization of a Fibrin-Specific Single-Chain Antibody Fragment from Bacillus subtilis: Effects of Molecular Chaperones and a Wall-Bound Protease on Antibody Fragment Production," Applied and Environmental Microbiology, Jul. 2002, p. 3261-3269, American Society for Microbiology, 2002.

Gupta, Ajay K. et al., "Synthesis and surface engineering of iron oxide nanoparticles for biomedical applications," Biomaterials, vol. 26, Issue 18, Jun. 2005, pp. 3995-4021.

Grady, M.S. et al., "Nonlinear magnetic stereotaxis: Three-dimensional, in vivo remote magnetic manipulation of a small object in canine brain," Medical Physics, vol. 17, No. 3, May/Jun. 1990, pp. 405-415.

(56) References Cited

OTHER PUBLICATIONS

Yodh, Shyarn B. et al., "A New Magnet System for 'Intravascular Navigation'", Med. & Biol. Engng., vol. 6, pp. 143-147 (1968).
Y. Yathindranath, et al. Simultaneous magnetically directed drug convection and MR imaging, Nanotechnolgy 20(40): paper #405101, 12 pgs. Sep. 2009.
A.J. Rosengart, et al., Magnetically Guided Plasminogen Activator-Loaded Designer Sphers for Acute Stroke Lysis, Medical Hypotheses and Research, 2(3): p. 413-424, Jul. 2005.
Ci Acar HY, et al., Superparamagnetic nanoparticles stabilized by polymerized PEGylated coatings, Journal of magnetism and magnetic materials, 293(1):p. 107, May 2005.
Torno MD, et al., Improvement of in vitro thrombolysis employing magnetically-guided microspheres, Thrombosis Research, 121(6): p. 799-811, Jan. 2008.

\* cited by examiner

Rotation Frequency

DEVICES FOR CONTROLLING MAGNETIC NANOPARTICLES TO TREAT FLUID OBSTRUCTIONS

CROSS-REFERENCE TO RELATED APPLICATIONS

This application is a continuation of U.S. patent application Ser. No. 15/155,386 filed May 16, 2016, now U.S. Pat. No. 10,029,008, which is a continuation of U.S. patent application Ser. No. 14/268,244 filed May 2, 2014, now issued as U.S. Pat. No. 9,339,664, which is a continuation of U.S. patent application Ser. No. 13/505,447 having a 371(c) date of Aug. 21, 2012, now issued as U.S. Pat. No. 8,715,150, which is a National Phase application of International Application Number PCT/US2010/055133 filed Nov. 2, 2010, published as International Publication Number WO 2011/053984 on May 5, 2011, which claims priority to U.S. Provisional Application Ser. No. 61/280,321 filed on Nov. 2, 2009, each of which is incorporated herein by reference in its entirety.

STATEMENT REGARDING FEDERALLY SPONSORED RESEARCH OR DEVELOPMENT

Not applicable.

FIELD

The present invention relates to a system for the physical manipulation of free magnetic rotors in a circulatory system using a remotely placed magnetic field-generating stator.

INTRODUCTION

The treatment of fluid obstructions in the circulatory system, including vascular occlusions in vessels of the brain and vessels of the extremities, has included the use of drugs that can dissolve the obstructions and obstruction removal devices, e.g., thrombectomy devices. However, side-effects of such drugs are difficult to control and such obstruction removal devices often involve invasive procedures that cause unintended or secondary tissue damage. Both the use of drugs at normal dosages and the use of thrombectomy devices can cause death.

The management of magnetic fluids is a field that has had considerable attention and effort, but with limited success in medicine. A textbook "Ferrohydro-Dynamics," R. E. Rosensweig, Dover Publications, New York, 1985, provides a useful background of the physics of magnetic particles in fluids, but with virtually no coverage of applications in medicine. In the medical field, magnetic forces are used commercially to manipulate and navigate catheters and guide wires in arteries (e.g., Stereotaxis, Inc., St Louis, Mo.; and Magnetecs, Inc., Santa Monica, Calif.). However, such invasive techniques can cause unintended or secondary tissue damage as mentioned above. In addition, very-low frequency rotational magnetic fields have been used to navigate and orient magnetically-enabled gastro-intestinal "pillcams." Although the use of magnetic nanoparticles has been proposed for magnetic resonance imaging contrast enhancement, tissue repair, immunoassays, detoxification of biological fluids, hyperthermia, drug delivery and in cell separation in the circulatory system, such uses have failed to overcome the difficulty of targeted delivery of the drug in areas of low blood flow, or total blockage because of the small magnetic moment of such nanoparticles. In other instances, magnetic nanoparticles have been conjugated to compounds, such as antibodies, that specifically bind to certain cell types or occlusions in the circulatory system, but the use of such targeting methods in a low blood flow or blocked circulatory system have not succeeded.

Therefore, what is needed are new devices and methods of treating fluid obstructions by increasing the safety of drug delivery and reducing the use of invasive surgical entry.

SUMMARY

A therapeutic system is provided comprising (a) a magnet having a magnetic field and a gradient for controlling magnetic rotors in a circulatory system, and (b) a controller for positioning and rotating the field and the gradient in a manner to agglomerate and traverse the magnetic rotors with respect to a therapeutic target in the circulatory system. Using the therapeutic system, contact of the therapeutic target with a pharmaceutical composition in the circulatory system is increased. In various aspects, the pharmaceutical composition can be attached to the magnetic rotor, and in other aspects can be administered to the circulatory system separate from the magnetic rotors. In certain instances, the pharmaceutical composition can be a thrombolytic drug.

Therapeutic targets of the system can include fluid obstructions such as atherosclerotic plaques, fibrous caps, fatty buildup, coronary occlusions, arterial stenosis, arterial restenosis, vein thrombi, arterial thrombi, cerebral thrombi, embolism, hemorrhage and very small vessels. In various aspects, the circulatory system is vasculature of a patient, in particular a human patient.

In various embodiments, the therapeutic system comprises a permanent magnet coupled to a motor, and the controller controls a motor to position the magnet at an effective distance, an effective plane with respect to the therapeutic target, and rotates the magnet at an effective frequency with respect to the therapeutic target. In various embodiments, the therapeutic system comprises an electromagnet having a magnetic field strength and magnetic field polarization driven by electrical current, and the controller positions the electromagnet at an effective distance, an effective plane with respect to the therapeutic target, and rotates the magnetic field of the electro-magnet by adjusting the electrical current.

The therapeutic system can further include a display for viewing the magnetic rotors and therapeutic target, and a user interface for controlling the magnetic rotors, such that a user controls the magnetic rotors to clear the therapeutic target by adjusting a frequency of the rotating magnetic field, a plane of the rotating magnetic field with respect to the therapeutic target, and a distance of the rotating magnetic field with respect to the therapeutic target. In various aspects, the therapeutic target can be a thrombosis in a human blood vessel. In various aspects, the magnetic rotors can be magnetic nanoparticles injected into the circulatory system.

In various aspects of the invention, the magnetic rotors traverse through the fluid in the circular motion by repeatedly (a) walking end over end along the blood vessel away from the magnetic field in response to the rotation of the rotors and an attractive force of the magnetic field, and (b) flowing back through the fluid towards the magnetic field in response to the rotation of the rotors and the attractive force of the magnetic field.

In yet another embodiment, a therapeutic system is provided for increasing fluid flow in a circulatory system comprising a magnet having a magnetic field for controlling a magnetic tool in the fluid, and a controller positioning and rotating the magnetic field with respect to the therapeutic target to rotate an abrasive surface of the magnetic tool and maneuver the rotating abrasive surface to contact and increase fluid flow through or around the therapeutic target. In various aspects, the circulatory system can be vasculature of a patient, particularly a human patient. In various aspects, the magnetic tool can be coupled to a stabilizing rod, and the magnetic tool rotates about the stabilizing rod in response to the rotating magnetic field. In yet another aspect, the magnetic tool can include an abrasive cap affixed to a magnet which engages and cuts through the therapeutic target. In another aspect, the controller positions the magnetic tool at a target point on the therapeutic target, and rotates the magnetic tool at a frequency sufficient to cut through the therapeutic target. The magnet can be positioned so that poles of the magnet periodically attract the opposing poles of the magnetic tool during rotation, the magnetic tool is pushed towards the therapeutic target by a stabilizing rod upon which the magnetic tool rotates. In another aspect, the magnet can be positioned so that the poles of the magnet continuously attract the opposing poles of the magnetic tool during rotation, and the magnetic tool is pulled towards the therapeutic target by an attractive force of the magnet.

In another embodiment, a system is provided for increasing fluid flow in a circulatory system comprising a magnet having a magnetic field for controlling magnetic rotors in the fluid, a display for displaying, to a user, the magnetic rotors and the therapeutic target in the fluid, and a controller, in response to instructions from the user, controlling the magnetic field to: (a) position the magnetic rotors adjacent to the therapeutic target, (b) adjust an angular orientation of the magnetic rotors with respect to the therapeutic target, and (c) rotate and traverse the magnetic rotors through the fluid in a circular motion to mix the fluid and substantially clear the therapeutic target.

In various aspects, the display can display real time video of the magnetic rotors and the therapeutic target, and the display can superimpose a graphic representative of a rotation plane of the magnetic field and another graphic representative of the attractive force of the magnetic field on the real time video. In another aspect, the magnet can be a permanent magnet coupled to a motor and a movable arm, and the controller can include a remote control device for a user to manipulate the position, rotation plane and rotation frequency of the magnetic field with respect to the therapeutic target.

In another aspect, the display can adjust the graphics in response to instructions given by the user through the remote control device. In various aspects, the magnet can be an electro-magnet coupled to a motor and a movable arm, and the controller can perform image processing to identify the location, shape, thickness and density of the therapeutic target, and automatically manipulates the movable arm to control the position, rotation plane and rotation frequency of the magnetic field to clear the therapeutic target.

In yet another aspect, the magnetic rotors can be formed by magnetic nanoparticles which combine in the presence of the magnetic field. In another aspect, the fluid can be a mixture of blood and a thrombolytic drug, the blood and thrombolytic drug being mixed by the circular motion of the magnetic rotors to erode and clear the therapeutic target. In yet another aspect, the circular motion of the magnetic rotors can redirect the thrombolytic drug from a high flow blood vessel to a low flow blood vessel which contains the therapeutic target.

A method is also provided for increasing fluid flow in a circulatory system comprising: (a) administering a therapeutically effective amount of magnetic rotors to the circulatory system of a patient in need thereof, and (b) applying a magnet to the patient, the magnet having a magnetic field and a gradient for controlling the magnetic rotors in a circulatory system, and (c) using a controller for positioning and rotating the field and the gradient in a manner to agglomerate and traverse the magnetic rotors with respect to a therapeutic target in the circulatory system of the patient, wherein contact of the therapeutic target with a pharmaceutical composition in the circulatory system is increased and fluid flow is increased.

In various aspects, the pharmaceutical composition can be attached to the magnetic rotor. In other aspects, the pharmaceutical composition can be administered to the circulatory system of the patient separate from the magnetic rotors. In various embodiments, the pharmaceutical composition is a thrombolytic drug.

In various aspects, therapeutic target can be a fluid obstruction such as atherosclerotic plaques, fibrous caps, fatty buildup, coronary occlusions, arterial stenosis, arterial restenosis, vein thrombi, arterial thrombi, cerebral thrombi, embolism, hemorrhage and very small vessel. In yet another aspect, the circulatory system is vasculature of a patient, particularly a human patient.

In yet another aspect, the magnet can be a permanent magnet coupled to a motor, and the controller can control a motor to position the magnet at an effective distance, an effective plane with respect to the therapeutic target, and rotates the magnet at an effective frequency. In another aspect, the magnet can be an electromagnet having a magnetic field strength and magnetic field polarization driven by electrical current, and the controller can position the electromagnet at an effective distance, an effective plane with respect to the therapeutic target, and rotates the magnetic field of the electro-magnet by adjusting the electrical current.

The system of the method can further include a display for viewing the magnetic rotors and therapeutic target, and a user interface for controlling the magnetic rotors, wherein a user controls the magnetic rotors to increase contact of the therapeutic target with a pharmaceutical composition in the circulatory system by adjusting a frequency of the rotating magnetic field, a plane of the rotating magnetic field with respect to the therapeutic target, and a distance of the rotating magnetic field with respect to the therapeutic target.

In various aspects, the therapeutic target can be a thrombosis in a human blood vessel. In another aspect, the magnetic rotors can be magnetic nanoparticles injected into the circulatory system. In particular, the therapeutic target is a full or partial blockage of a vein bivalve. In yet another aspect, the magnetic rotors traverse through the fluid in the circular motion by repeatedly (a) walking end over end along the blood vessel away from the magnetic field in response to the rotation of the rotors and an attractive force of the magnetic field, and (b) flowing back through the fluid towards the magnetic field in response to the rotation of the rotors and the attractive force of the magnetic field.

In various aspects, the rotor is a magnetic nanoparticle of a diameter from about 20 nm to about 60 nm. In another aspect, the therapeutic target is a vascular occlusion in the patient head or a vascular occlusion in the patient leg.

In yet another embodiment, a method is provided for increasing drug diffusion in a circulatory system comprising (a) administering a therapeutically effective amount of magnetic rotors to the circulatory system of a patient in need thereof, and (b) applying a magnet to the patient, the magnet having a magnetic field and a gradient for controlling the magnetic rotors in a circulatory system, and (c) using a controller for positioning and rotating the field and the gradient in a manner to agglomerate and traverse the magnetic rotors with respect to a therapeutic target in the circulatory system of the patient, wherein diffusion of a pharmaceutical composition in the circulatory system at the therapeutic target is increased.

In various aspects, the pharmaceutical composition can be attached to the magnetic rotor. In other aspects, the pharmaceutical composition can be administered to the circulatory system of the patient separate from the magnetic rotors. In various embodiments, the pharmaceutical composition is a thrombolytic drug.

In various aspects, therapeutic target can be a fluid obstruction such as atherosclerotic plaques, fibrous caps, fatty buildup, coronary occlusions, arterial stenosis, arterial restenosis, vein thrombi, arterial thrombi, cerebral thrombi, embolism, hemorrhage and very small vessel. In yet another aspect, the circulatory system is vasculature of a patient, particularly a human patient.

In yet another aspect, the magnet can be a permanent magnet coupled to a motor, and the controller can control a motor to position the magnet at an effective distance, an effective plane with respect to the therapeutic target, and rotates the magnet at an effective frequency. In another aspect, the magnet can be an electromagnet having a magnetic field strength and magnetic field polarization driven by electrical current, and the controller can position the electromagnet at an effective distance, an effective plane with respect to the therapeutic target, and rotates the magnetic field of the electro-magnet by adjusting the electrical current.

The system of the method can further include a display for viewing the magnetic rotors and therapeutic target, and a user interface for controlling the magnetic rotors, wherein a user controls the magnetic rotors to increase contact of the therapeutic target with a pharmaceutical composition in the circulatory system by adjusting a frequency of the rotating magnetic field, a plane of the rotating magnetic field with respect to the therapeutic target, and a distance of the rotating magnetic field with respect to the therapeutic target.

In various aspects, the therapeutic target can be a thrombosis in a human blood vessel. In another aspect, the magnetic rotors can be magnetic nanoparticles injected into the circulatory system. In particular, the therapeutic target is a full or partial blockage of a vein bivalve. In yet another aspect, the magnetic rotors traverse through the fluid in the circular motion by repeatedly (a) walking end over end along the blood vessel away from the magnetic field in response to the rotation of the rotors and an attractive force of the magnetic field, and (b) flowing back through the fluid towards the magnetic field in response to the rotation of the rotors and the attractive force of the magnetic field.

In various aspects, the rotor is a magnetic nanoparticle of a diameter from about 20 nm to about 60 nm. In another aspect, the therapeutic target is a vascular occlusion in the patient head or a vascular occlusion in the patient leg.

These and other features, aspects and advantages of the present teachings will become better understood with reference to the following description, examples and appended claims.

DRAWINGS

Those of skill in the art will understand that the drawings, described below, are for illustrative purposes only. The drawings are not intended to limit the scope of the present teachings in any way.

Figure 8A:
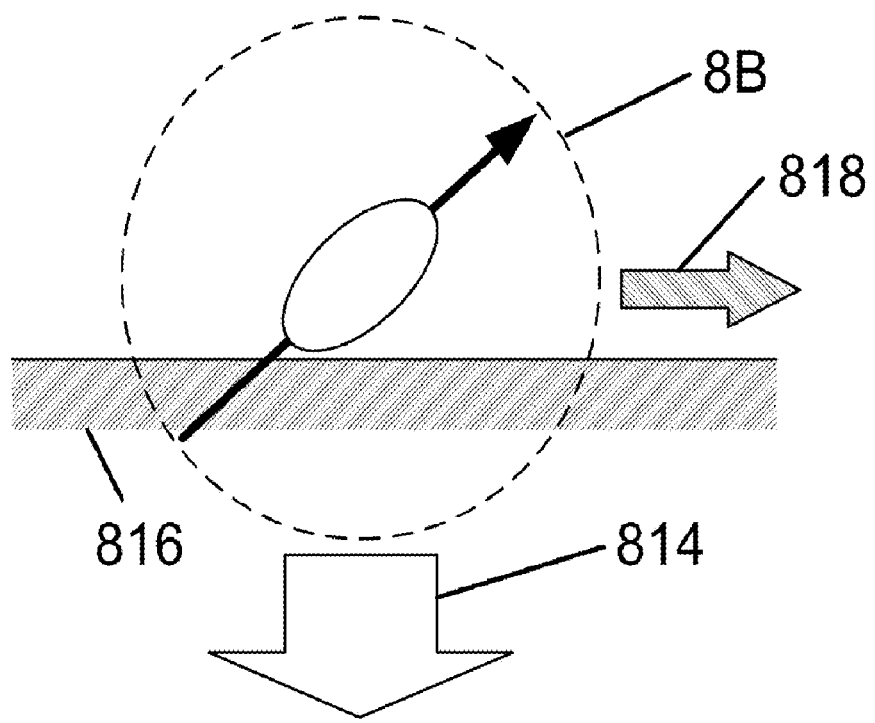
Figure 8B:
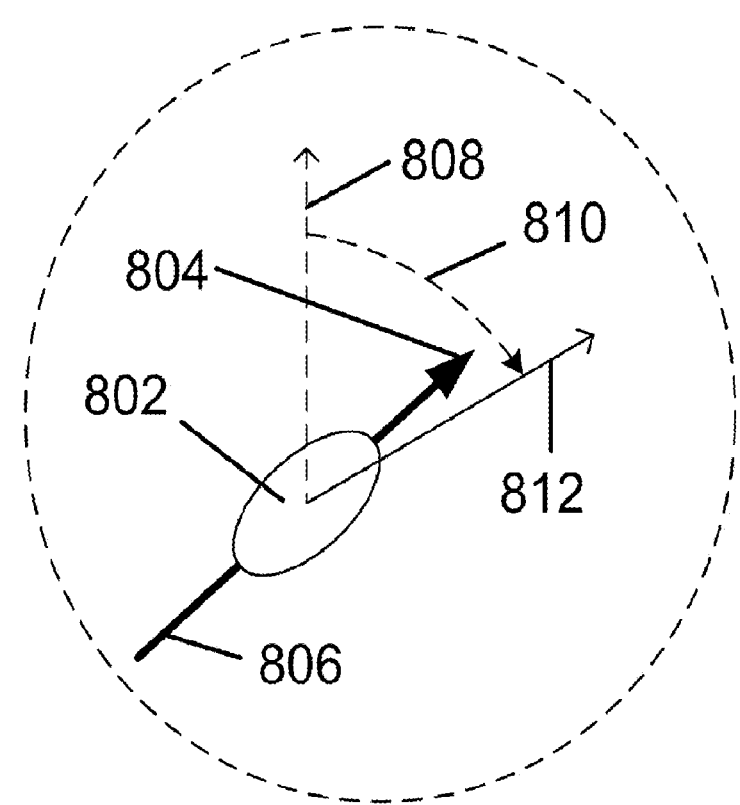
Figure 8C:
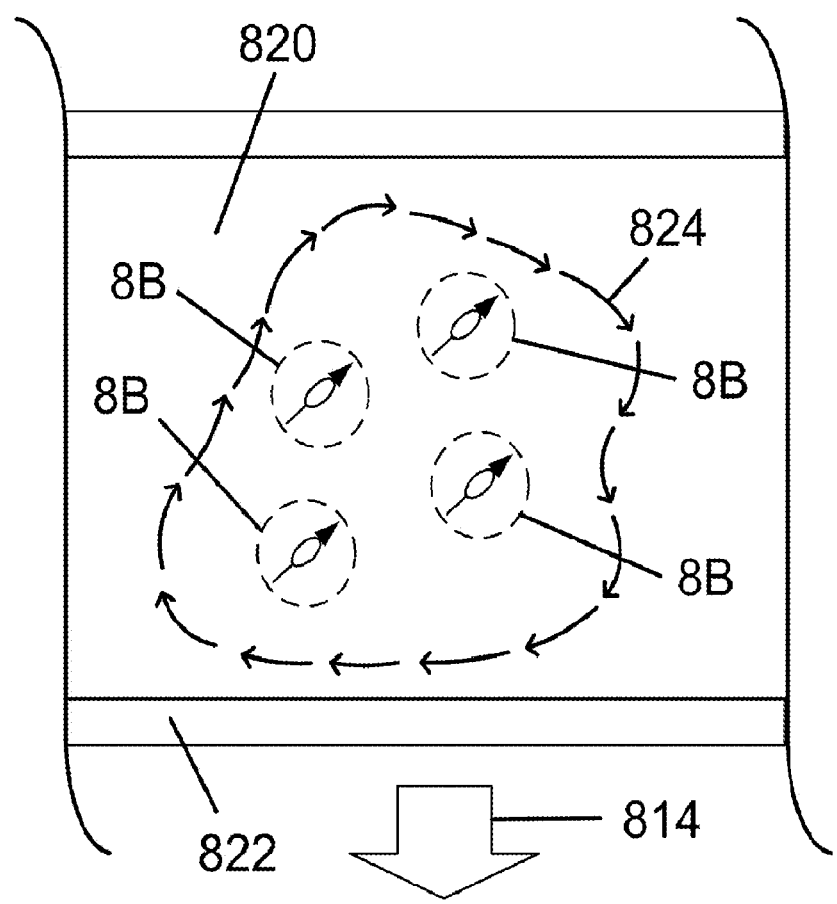
Figure 8D:
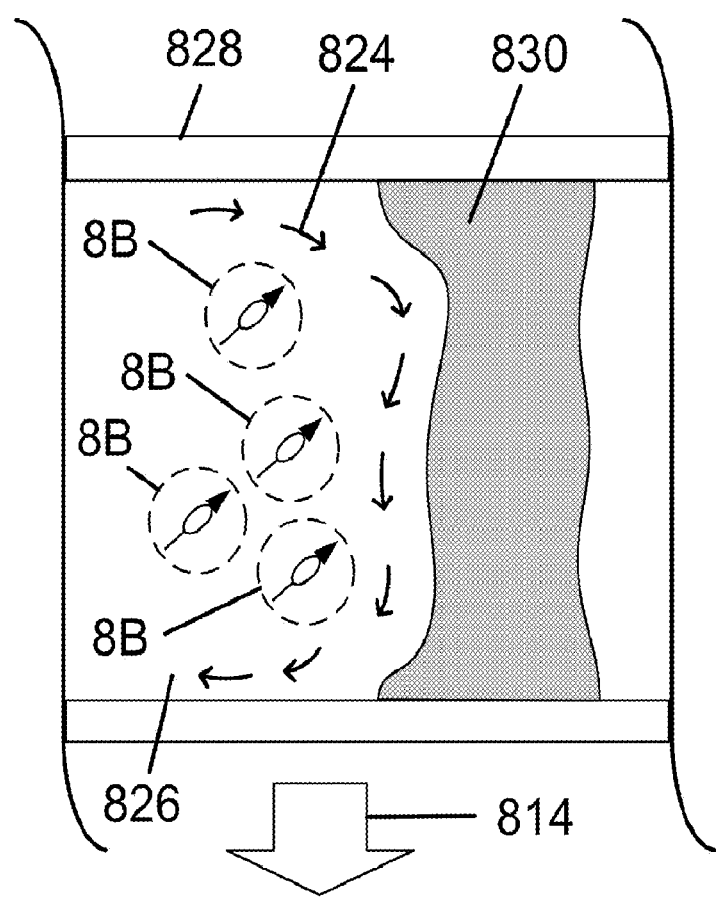

FIG. 8A shows the manipulation of magnetic particles to create motion. FIG. 8B details the action of the magnetic field on a magnetic particle to create rotation. FIG. 8C illustrates the magnetic manipulation of a magnetic particle distribution inside a fluid-filled enclosure to create flow patterns. FIG. 8D shows the magnetic manipulation of a magnetic particle distribution to amplify the effects of clot-busting drugs on a clot.

Figure 9:
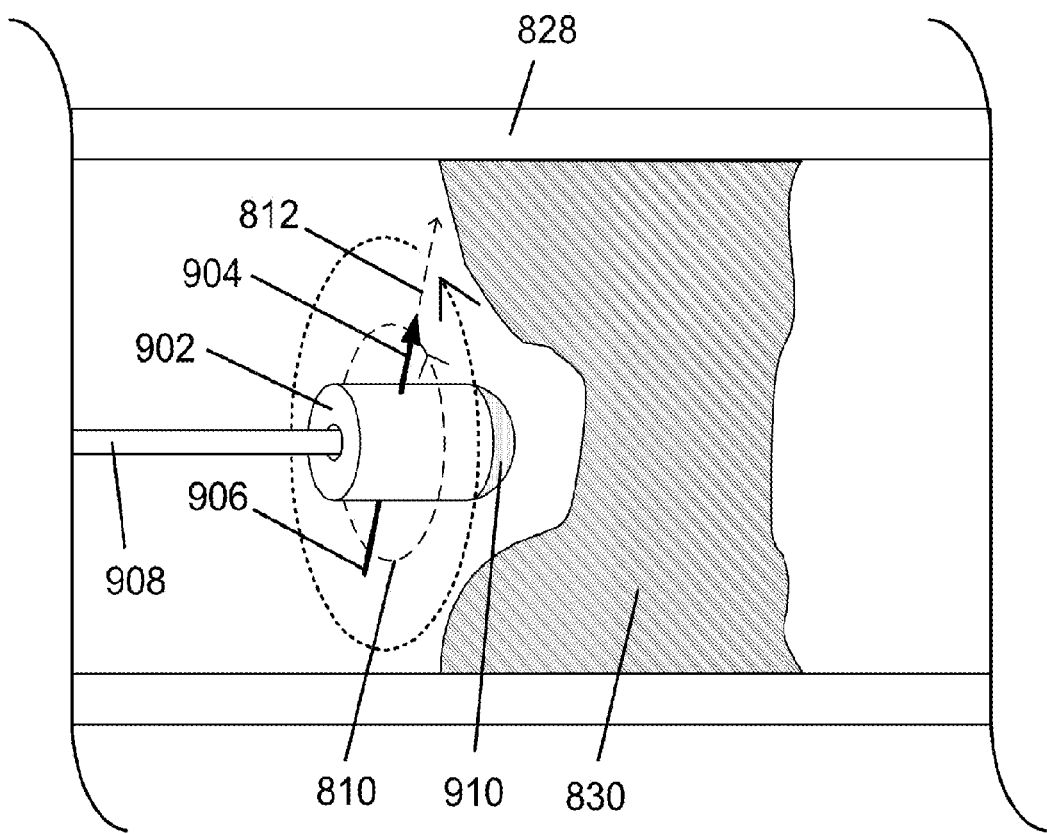

FIG. 9 illustrates the manipulation of a magnet to cross a vessel occlusion.

Figure 10A:
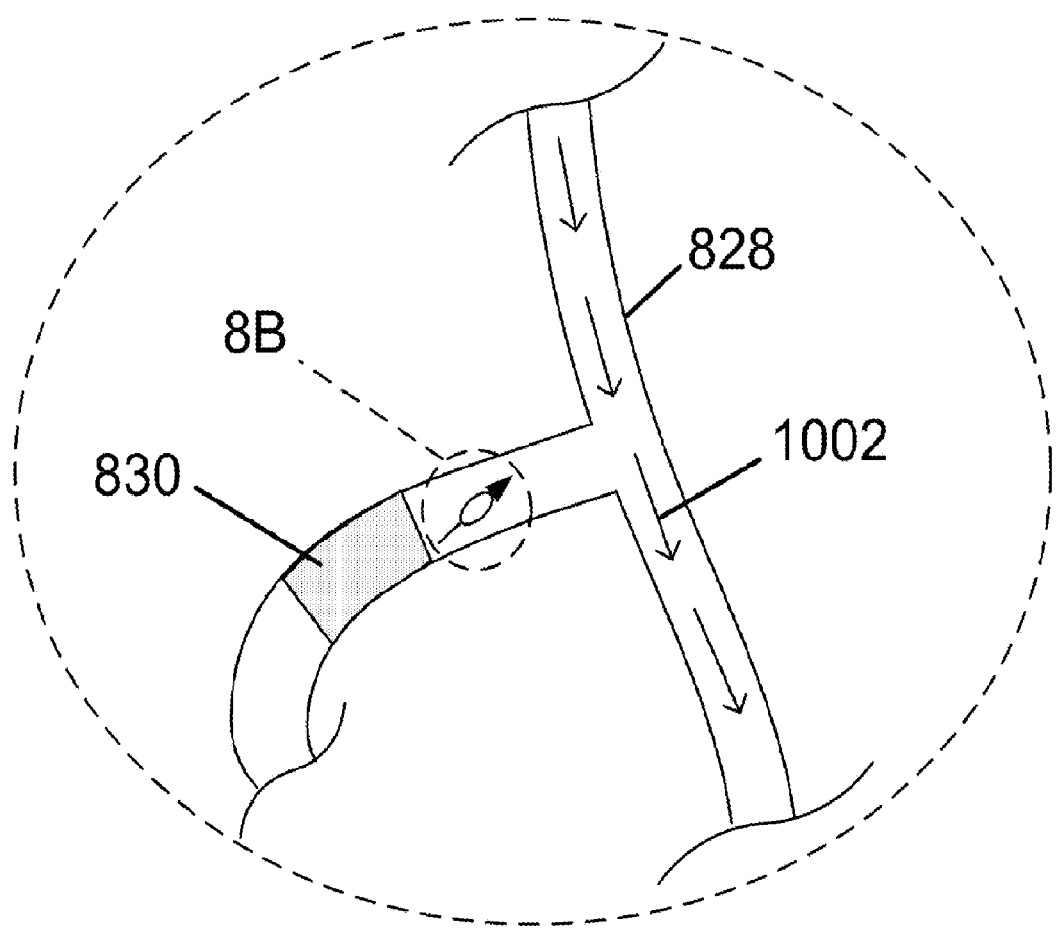
Figure 10B:
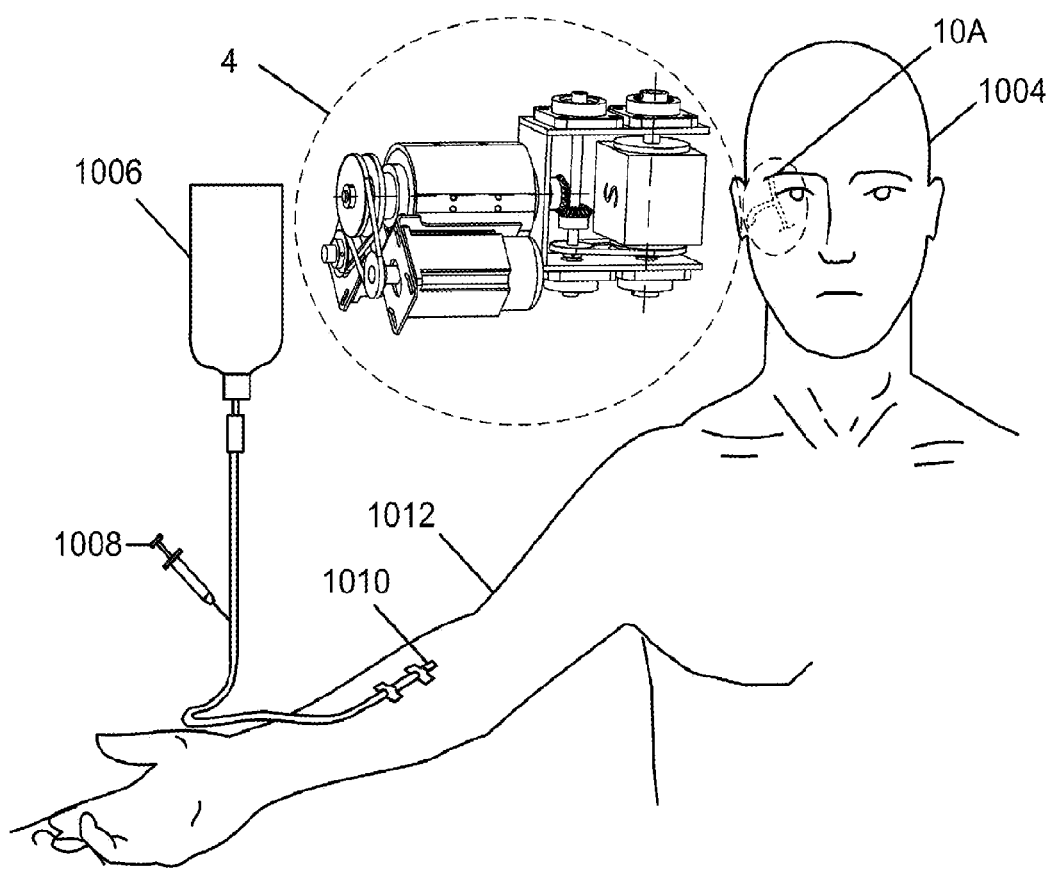

FIGS. 10A and 10B illustrate the use of the magnetomotive stator system and magnetic nanoparticles for the treatment of a vascular occlusion in the brain.

FIGS. 11A-E illustrate a model for the enhanced diffusion of pharmaceutical compounds in an area of complete blockage having no fluid flow, where (A) shows a vessel having no drug, (B) shows the addition of a drug to the system (grey), but the inability to mix at the site of the blockage, (C) the addition of magnetic nanoparticles to the system and drawn to the blockage site via magnet (not shown), (D) turbulence created by applying the magnetic field and gradient in a time-dependent fashion and mixing the drug to come closer to contacting the blockage site, and (E) showing completed diffusion of the drug and contact at the blockage site via mixing using the magnetic nanoparticles.

Figure 12:
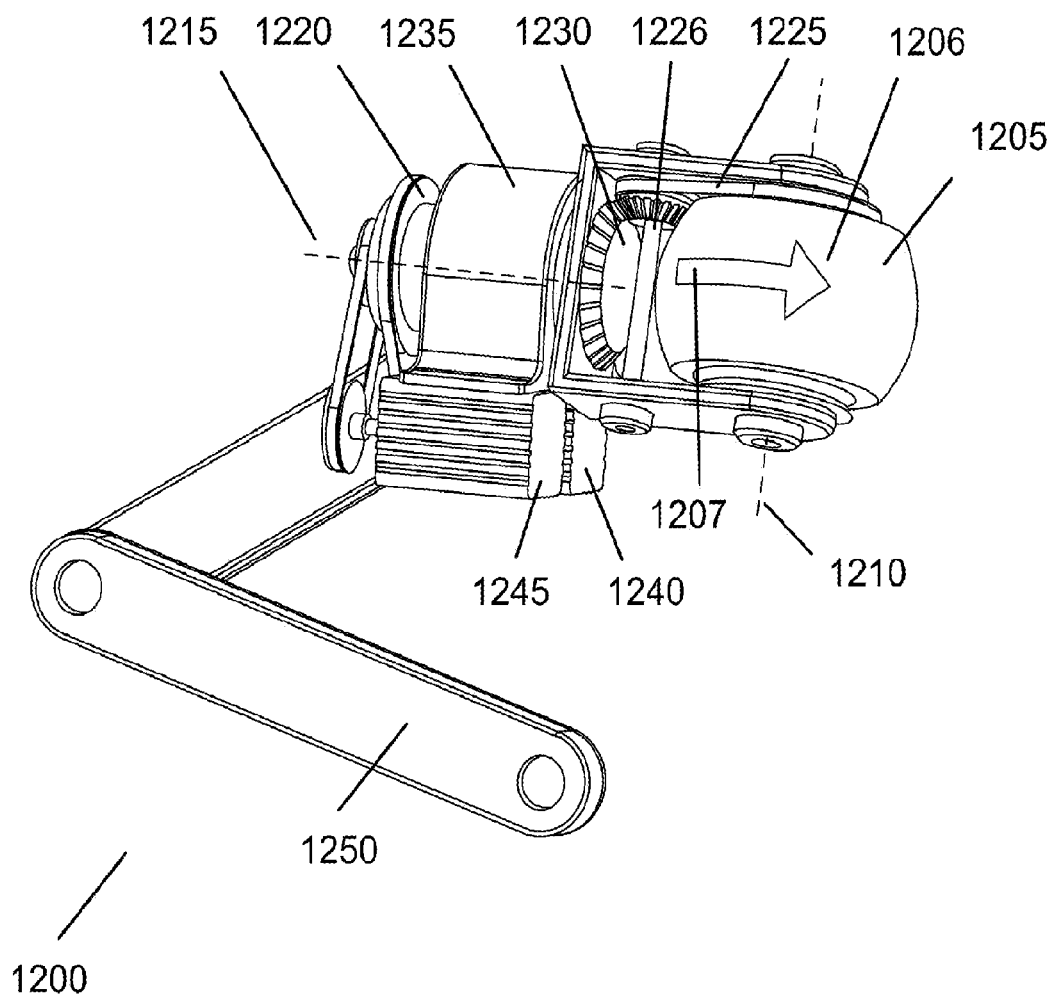

FIG. 12 is a drawing of the magnetic system that is a first preferred embodiment of this invention.

Figure 13:
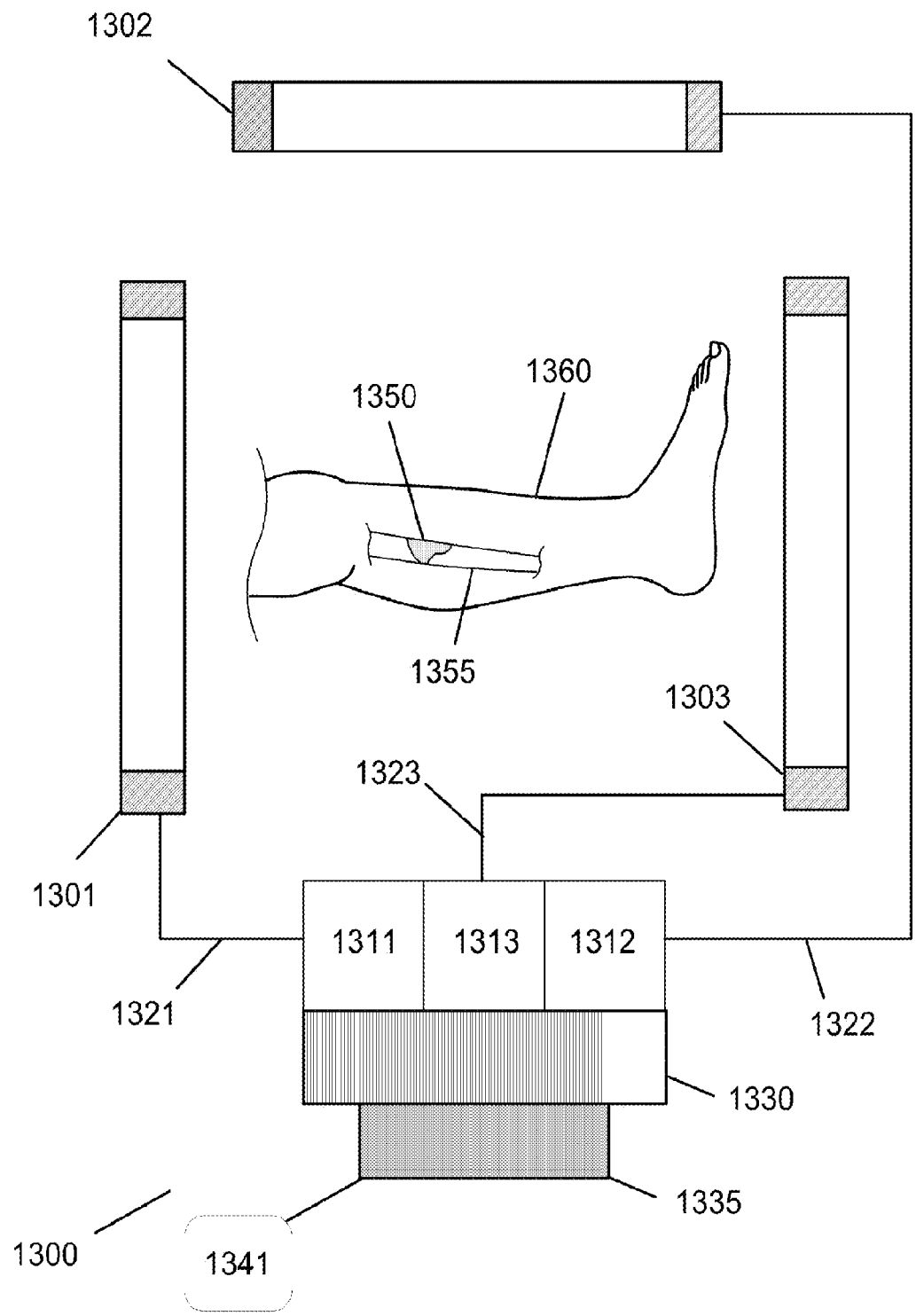

FIG. 13 is a drawing of the magnetic system that is a second preferred embodiment of this invention.

Figure 14A:
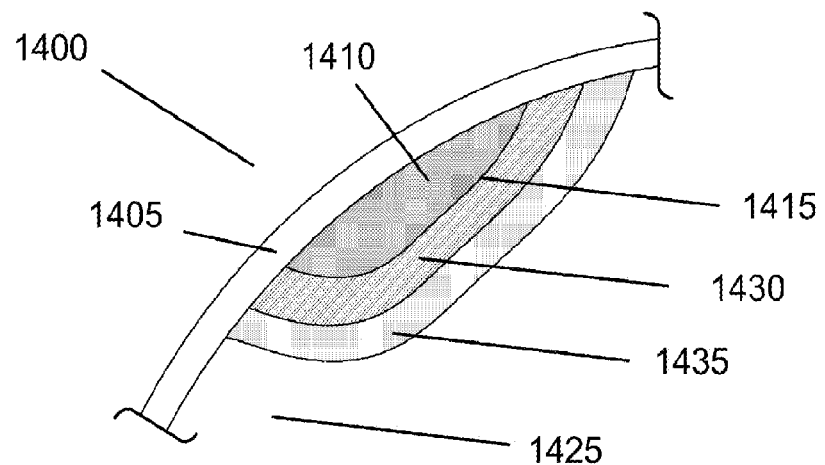

FIG. 14A is a cross sectional drawing displaying a representative targeted region of a blocked lumen with no flow, under conventional treatment.

Figure 14B:
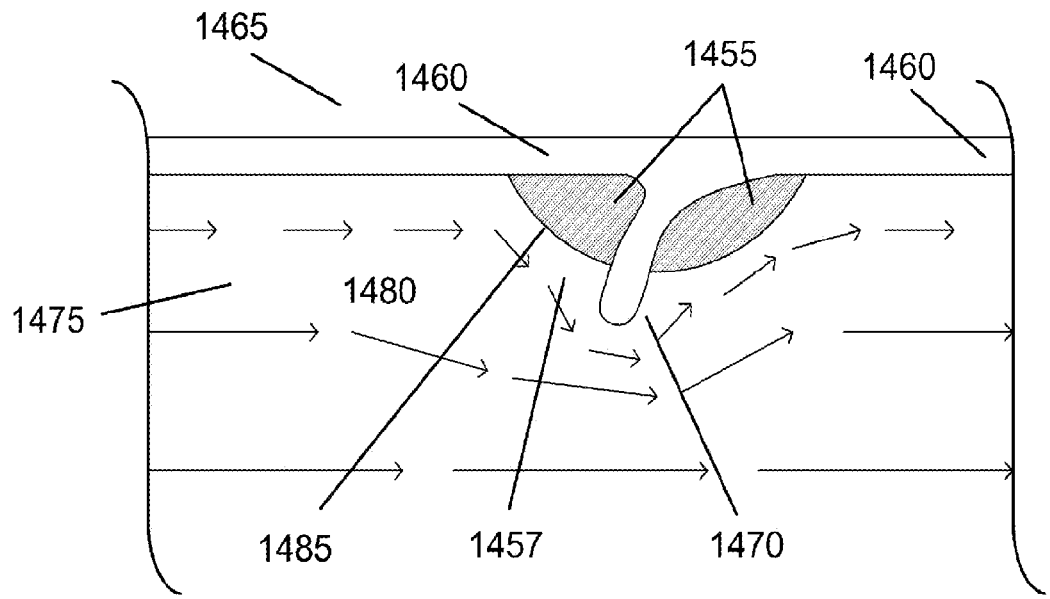

FIG. 14B is a cross sectional drawing of a targeted region having blood flow, but with ineffective drug clearance using standard drug delivery.

Figure 15A:
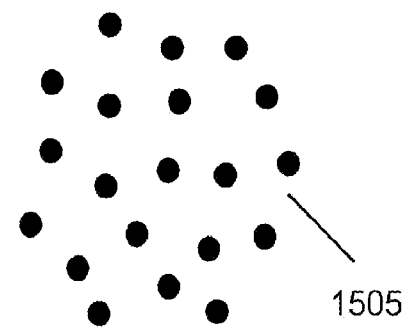
Figure 15B:
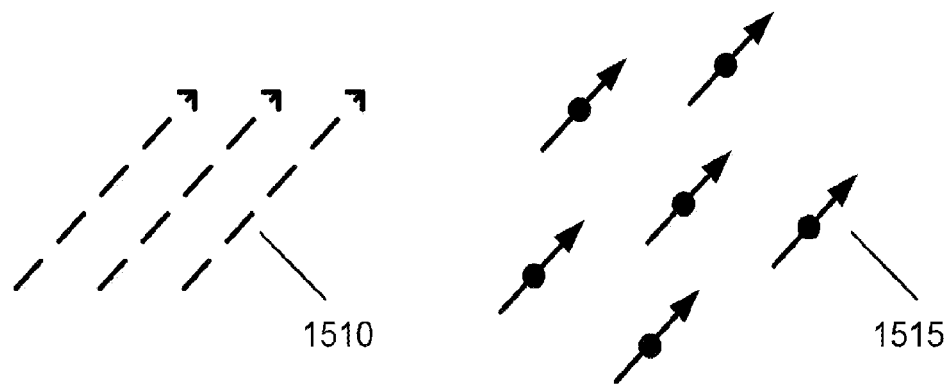
Figure 15C:
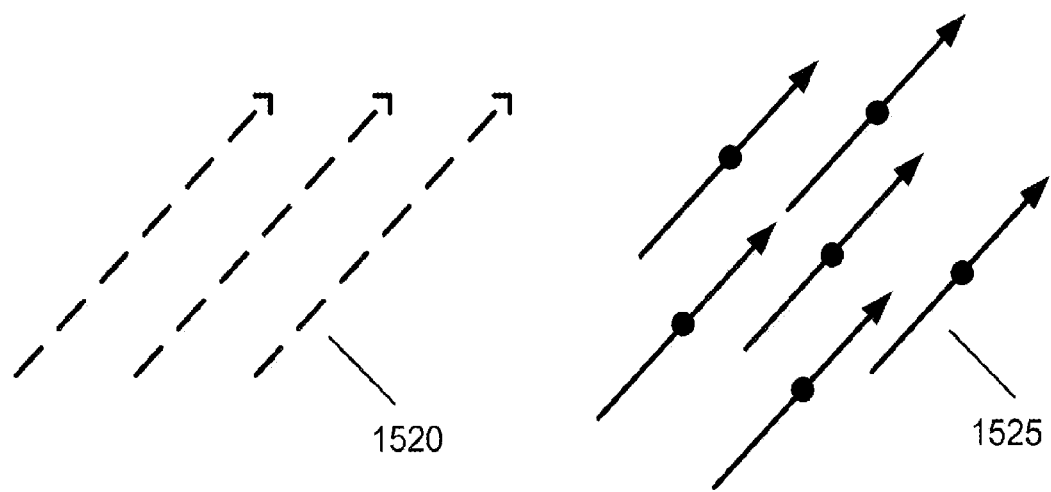

FIGS. 15A-15C show arranged structuring of magnetic nanoparticles to create rods as used in procedures with the present invention, where (A) shows unorganized nanoparticles in zero field, (B) shows a small field applied to the nanoparticles and organization into "rods," and (C) shows a larger field applied to the nanoparticles.

Figure 16:
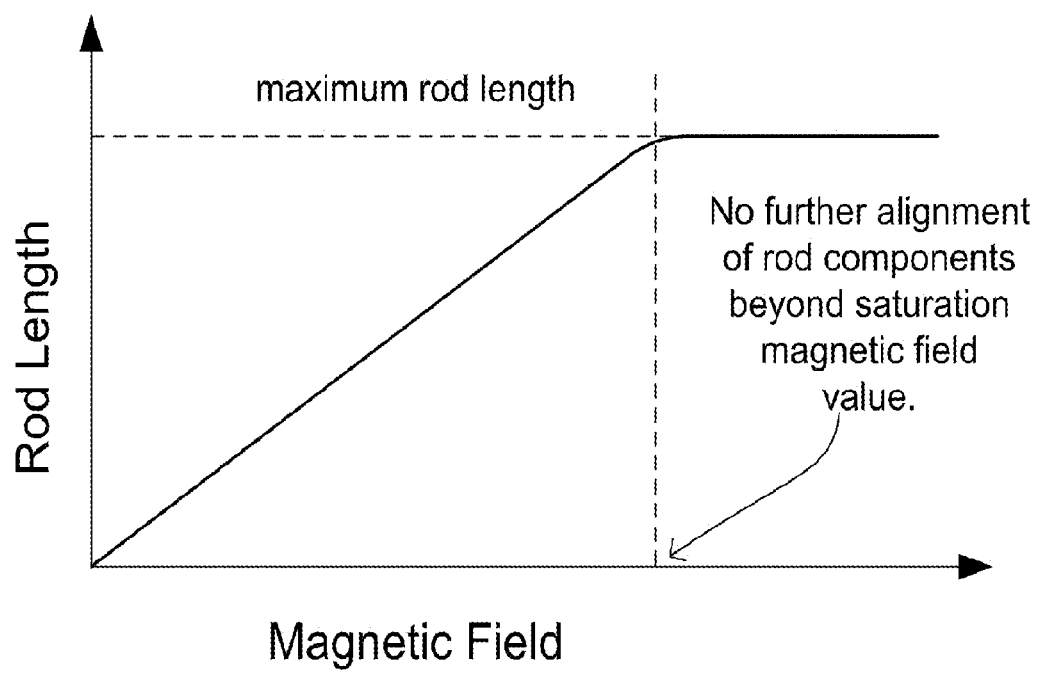

FIG. 16 is a plot of nanoparticle agglomerate rod length as a function of the applied magnetic field, showing a limiting length.

FIGS. 17A-17H depict a sequence of end over end motions leading to translation of the magnetic particle.

Figure 18A:
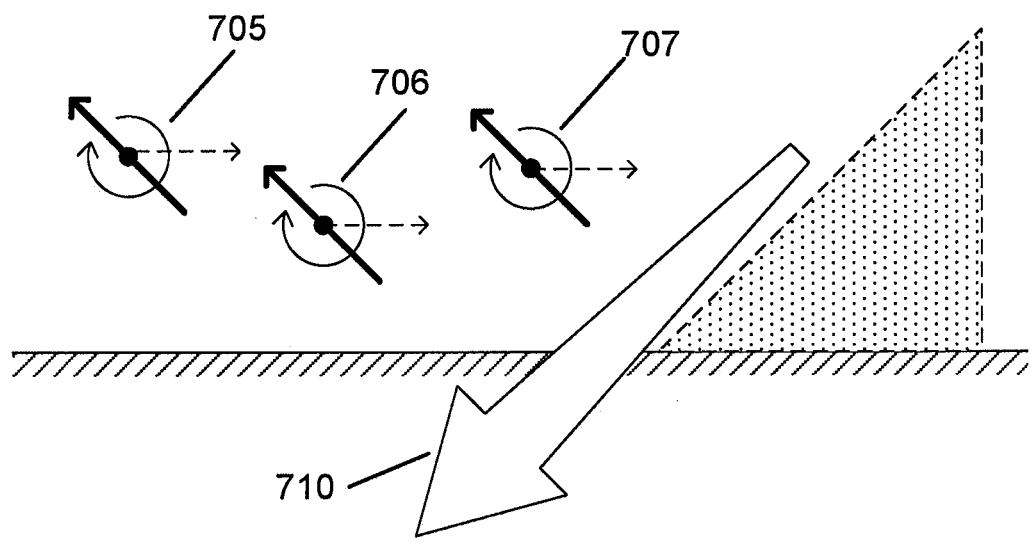
Figure 18B:
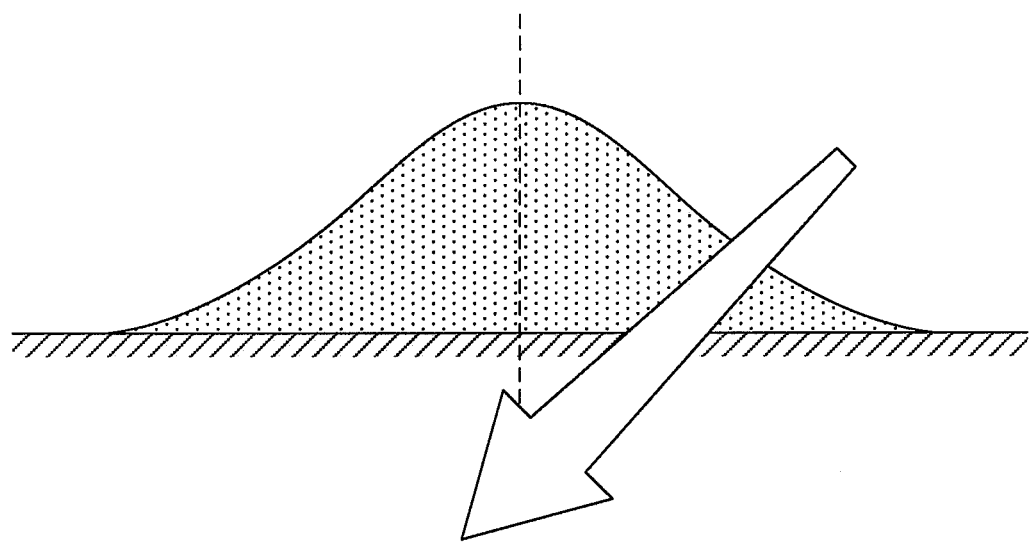

FIGS. 18A and 18B show the characteristic saturation of particles with increased density as a result of rotating motion leading to a buildup of magnetic particles.

Figure 19A:
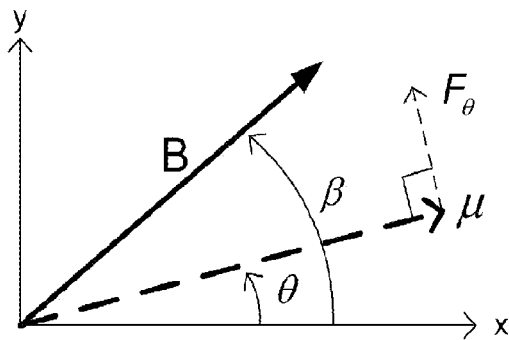
Figure 19B:
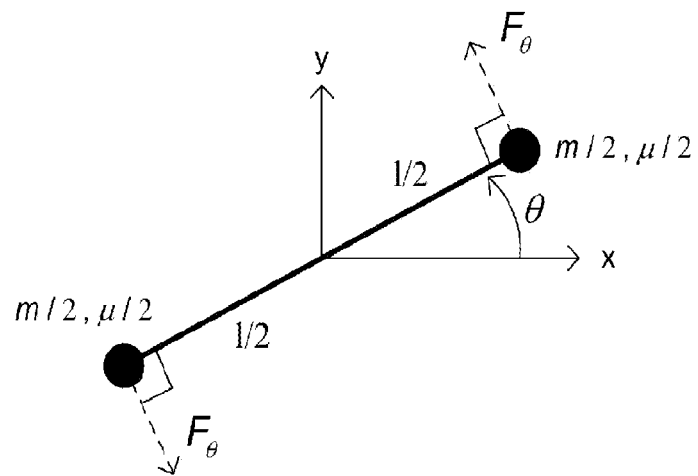

FIGS. 19A and 19B support a derivation of the physics of elements and fields leading to magnetic torque on a nanoparticle rod of this invention.

Figure 19C:
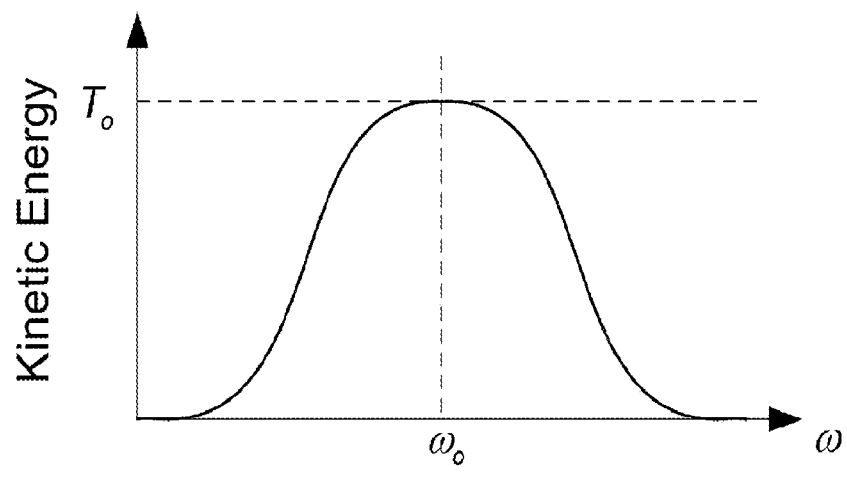

FIG. 19C describes the distribution of kinetic energy as a function of frequency of rotation of the rods.

Figure 20A:
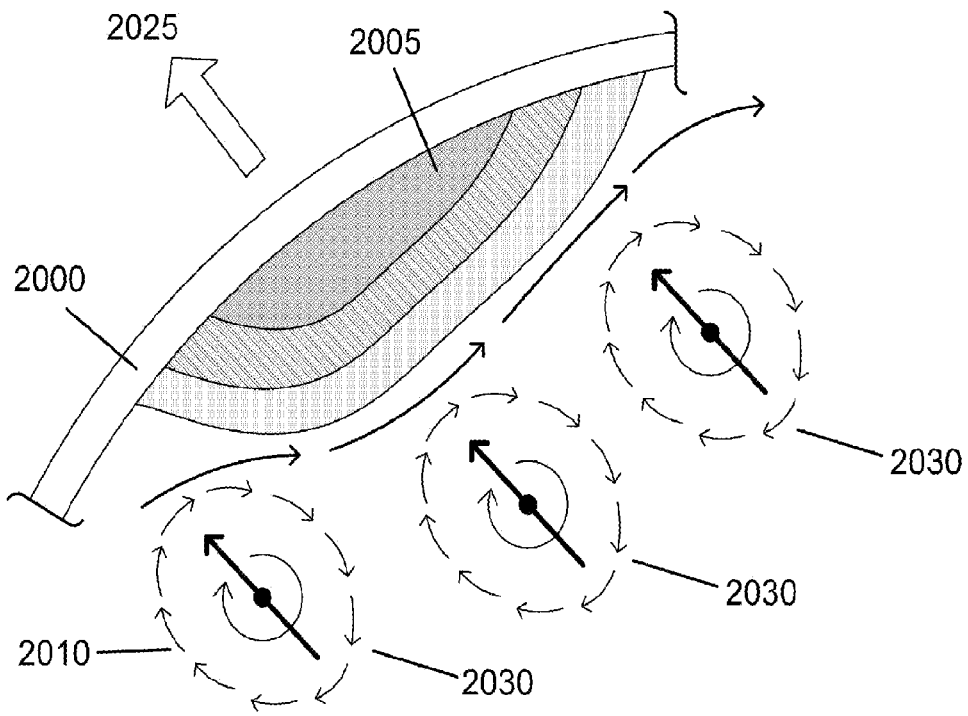

FIG. 20A shows the introduction of turbulence with spinning rods in a vessel with no flow, to treat the occlusion problem shown in FIG. 14A.

Figure 20B:
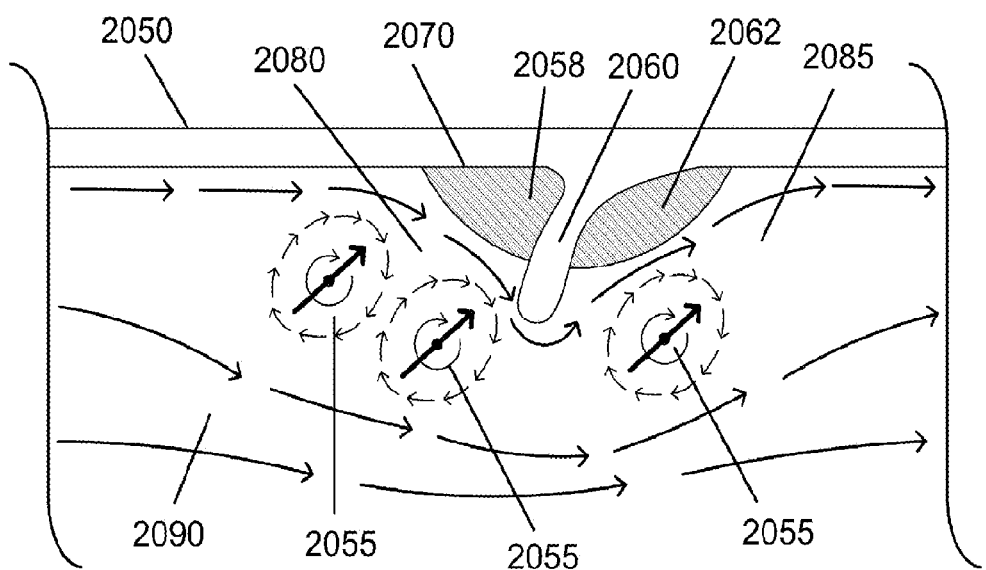

FIG. 20B exhibits motion and effect of drug delivery according to this invention for introduction of turbulence in the occluded flow category shown in FIG. 14B.

Figure 21A:
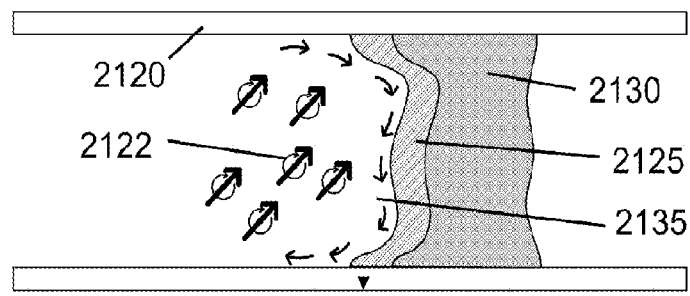

FIG. 21A is a cross section view of a group of rotating rods in circular motion against a total occlusion in a vessel.

Figure 21B:
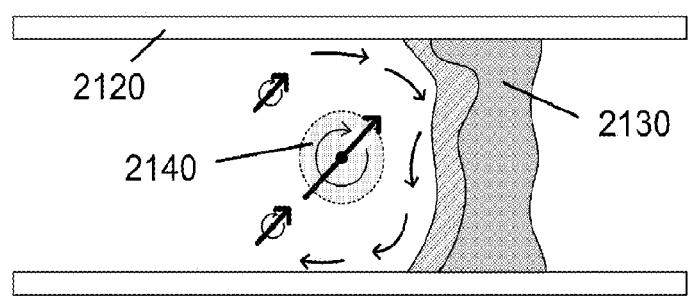

FIG. 21B is a cross section view of the rotation of rods starting to form a ball.

Figure 21C:
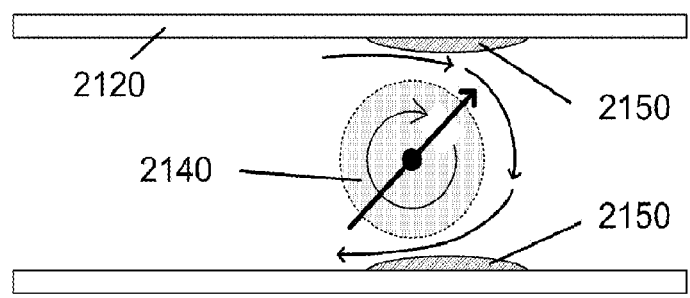

FIG. 21C is a cross section view of the rotating ball of rods and clot material having completely opened the obstructed vein.

Figure 21D:
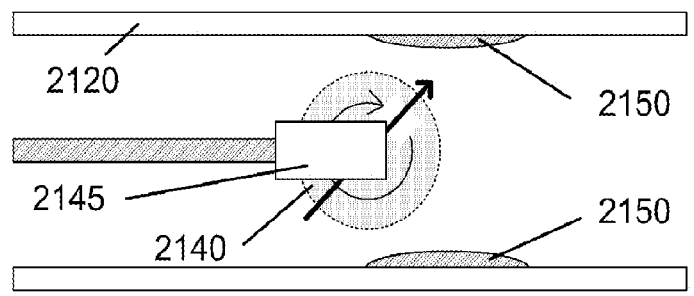

FIG. 21D is a cross section view of the ball of FIG. 21C being removed by a small magnet on a guide wire.

Figure 22:
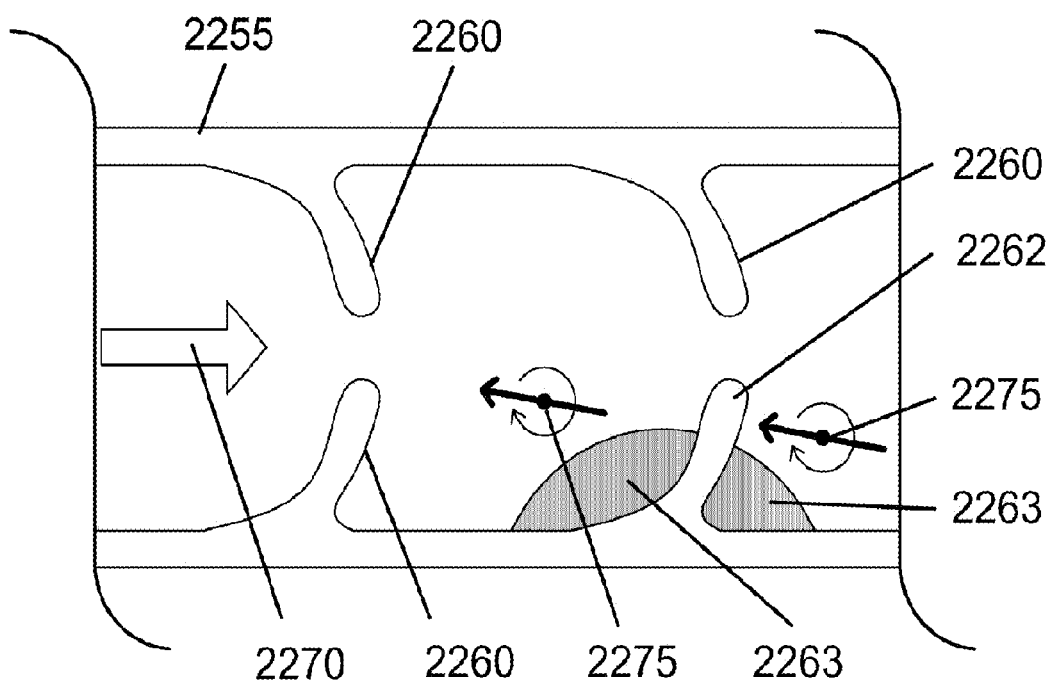

FIG. 22 is a cross section view of a vessel with rotating magnetic carriers applying drugs to safely remove occluding material on a valve leaflet in a blood vessel.

Figure 23:
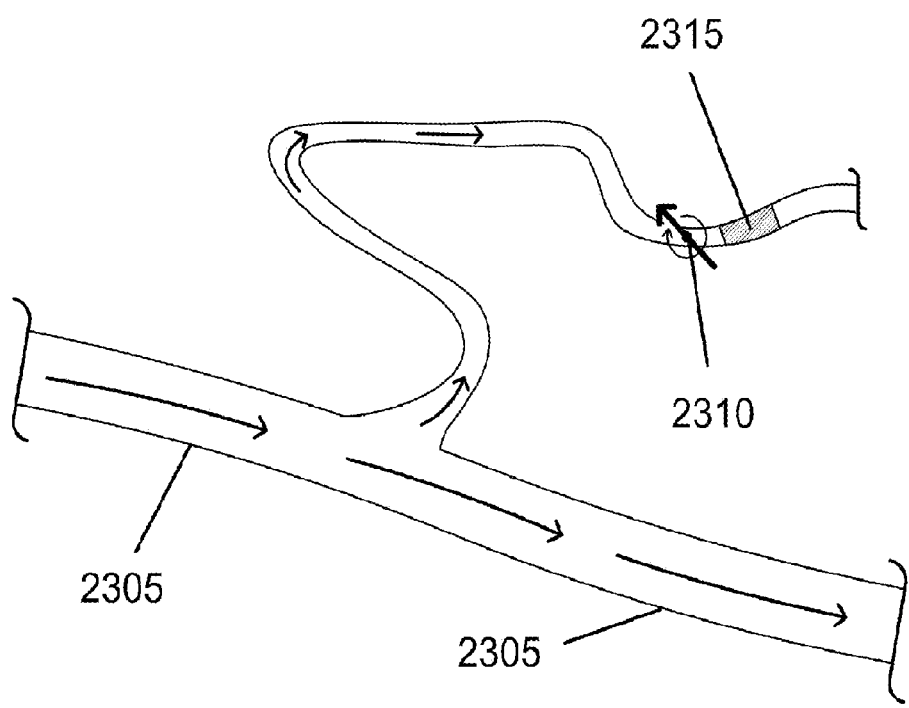

FIG. 23 exhibits the result of end over end motion of a magnetic rod "walk" along a path to a distant clot in a complex vessel.

Figure 24A:
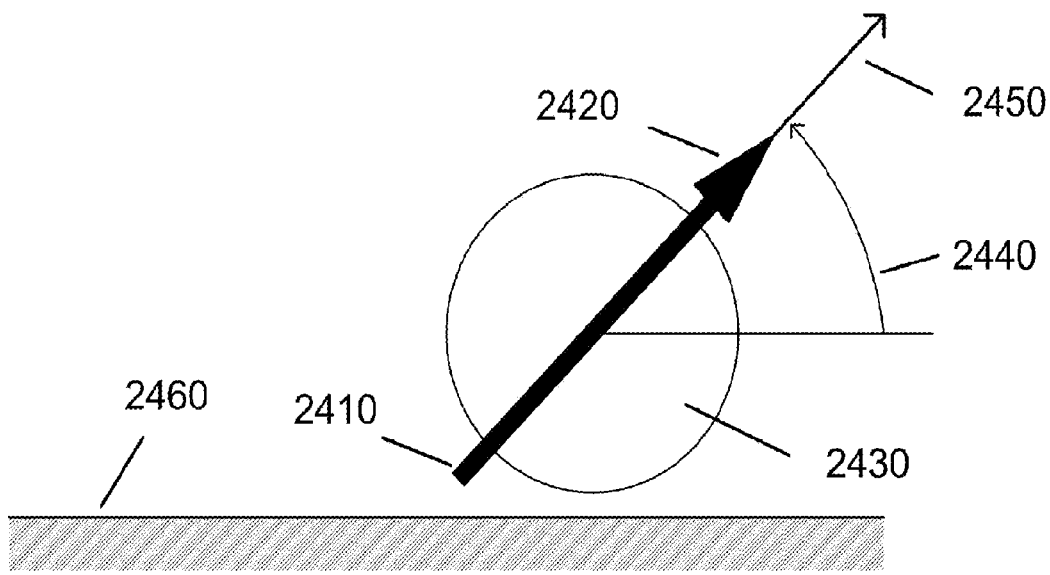
Figure 24B:
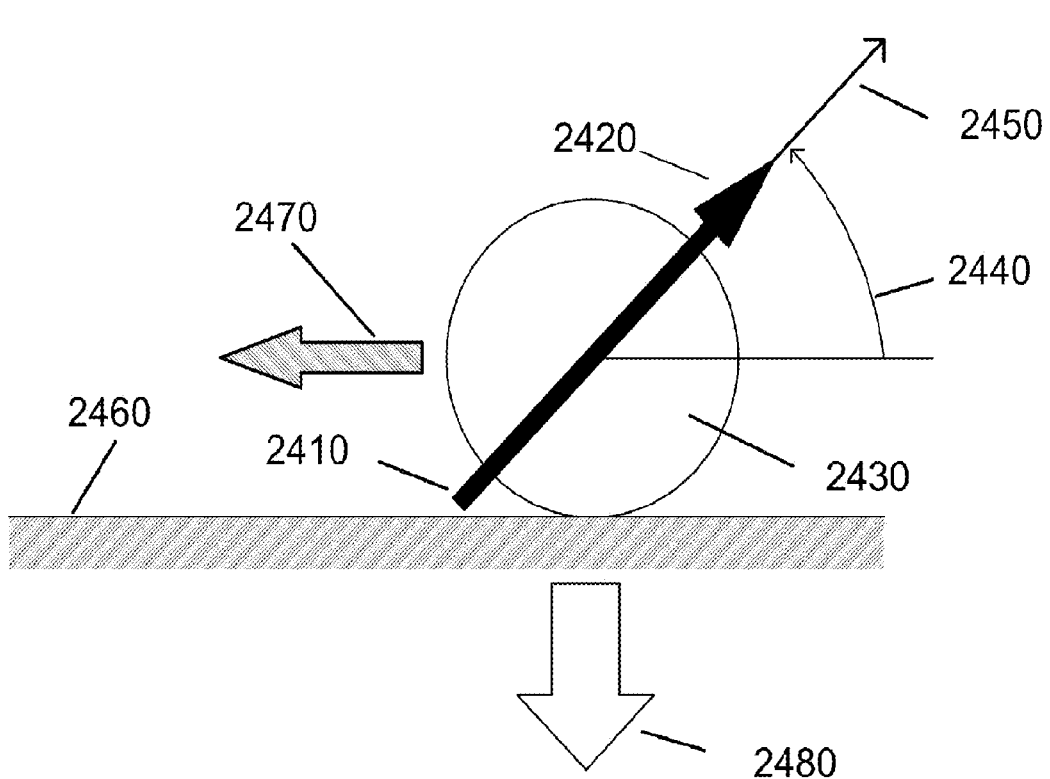

FIGS. 24A and 24B exhibit the generation of motion of a magnetically-enabled thrombectomy device which is depicted as a sphere, where (A) shows no field or gradient applied and (B) shows a field and gradient applied causing the sphere to traverse laterally.

Figure 25A:
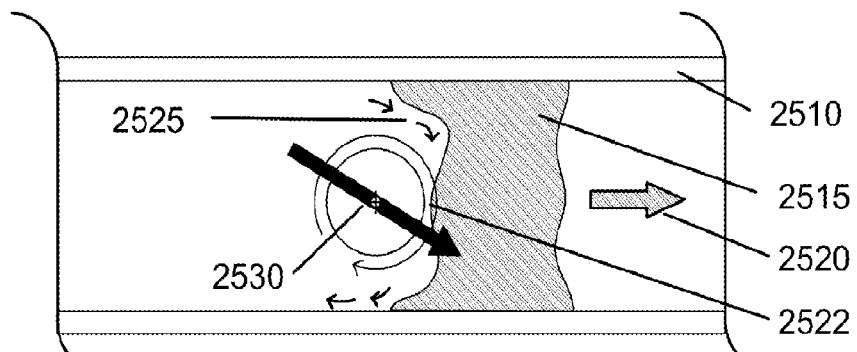

FIG. 25A is a cross section view of a rotating magnetically-enabled thrombectomy sphere in circular motion against a total occlusion in a vessel.

Figure 25B:
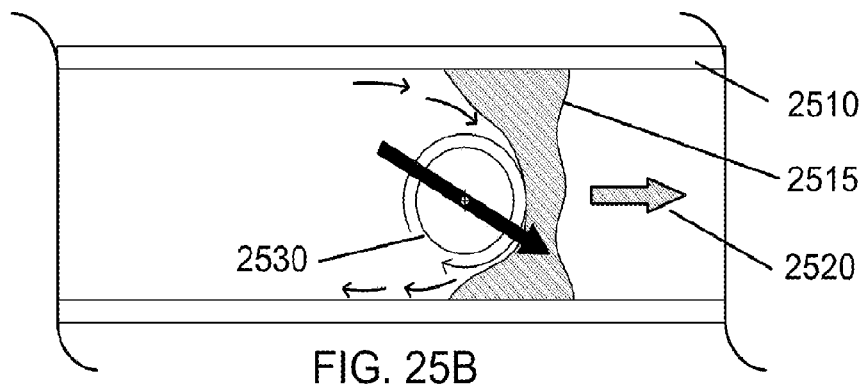

FIG. 25B is a cross section view of the magnetically-enabled thrombectomy sphere wearing away the surface of the occlusion.

Figure 25C:
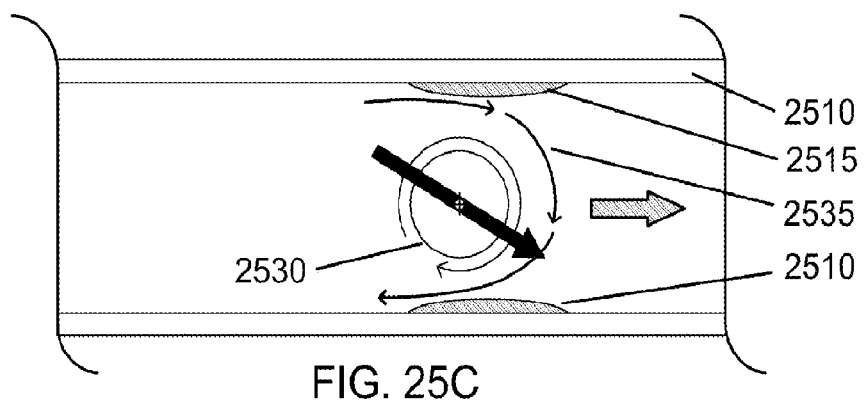

FIG. 25C is a cross section view of the magnetically-enabled thrombectomy sphere having completely opened the obstructed vein.

Figure 25D:
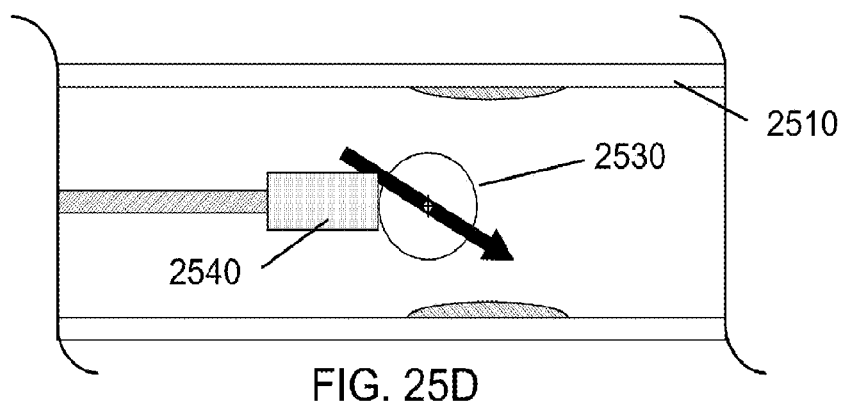

FIG. 25D is a cross section view of the magnetically-enabled thrombectomy sphere being removed by a small magnet on a guide wire.

Figure 26A:
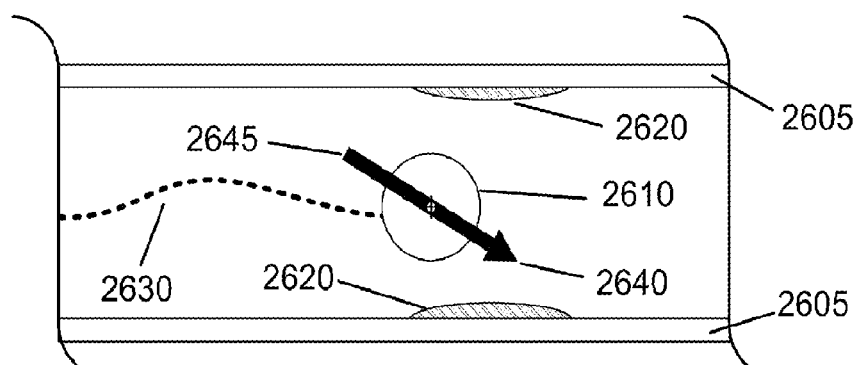

FIG. 26A is a cross section view of the tethered magnetically-enabled thrombectomy sphere having completely opened the obstructed vein.

Figure 26B:
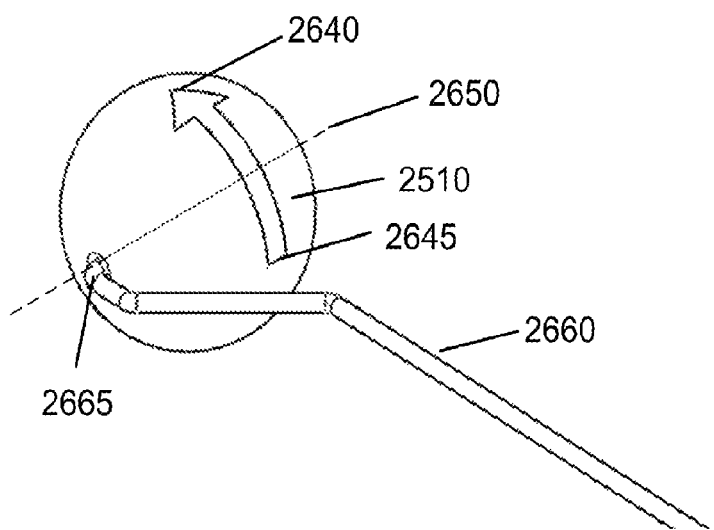

FIG. 26B is a tether embodiment which runs through the magnet's rotational axis.

Figure 26C:
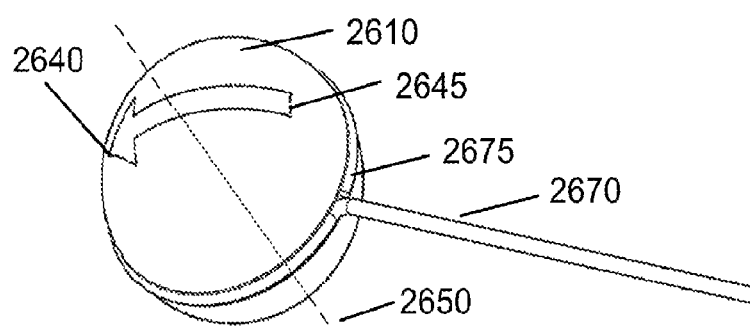

FIG. 26C is a second tether embodiment which loops around the magnet's rotational axis.

Figure 27:
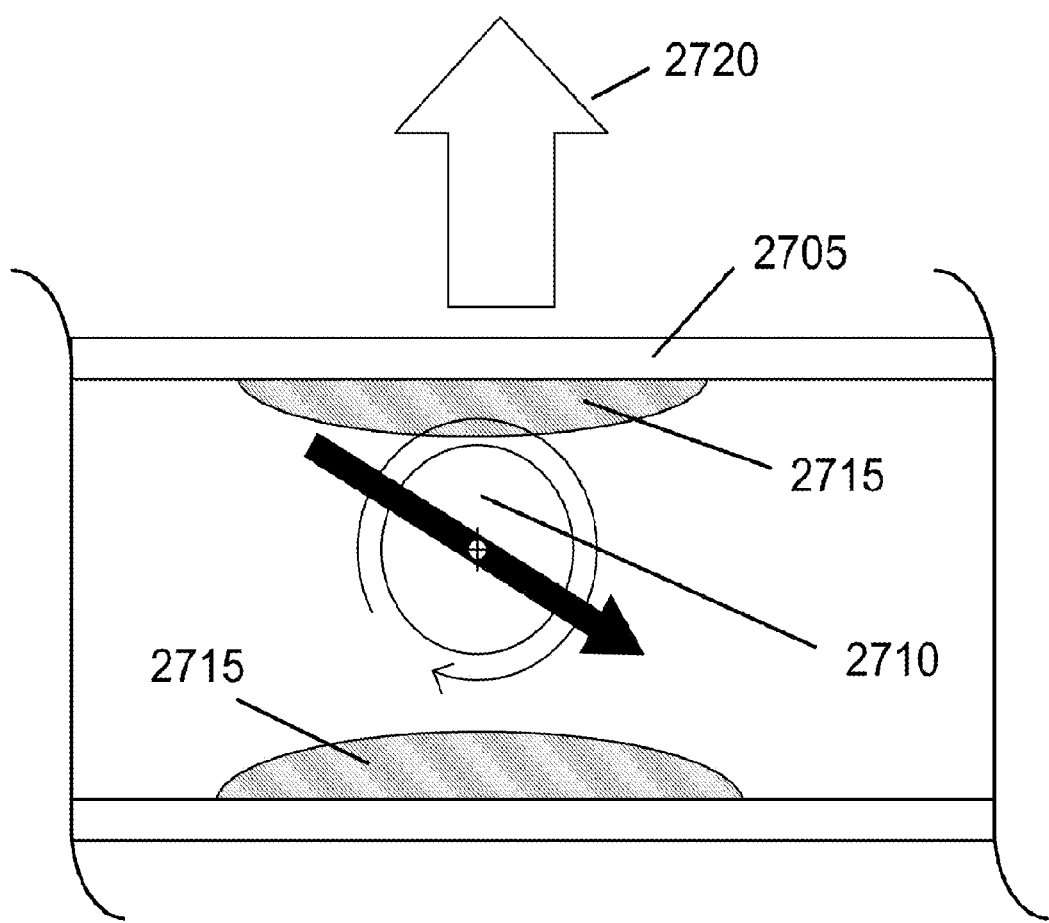

FIG. 27 is a cross section view of a rotating magnetically-enabled thrombectomy sphere in circular motion against plaque on the vessel walls.

Figure 28A:
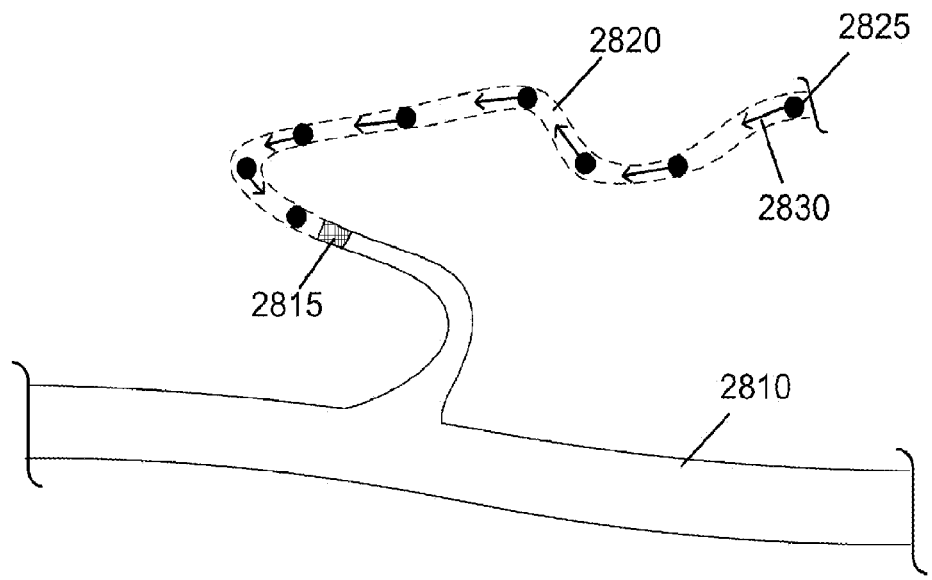

FIG. 28A exhibits the result of end over end motion of a magnetic rod or magnetic ball "walk" along a path to a distant clot in a complex vessel as imaged by an imaging technology.

Figure 28B:
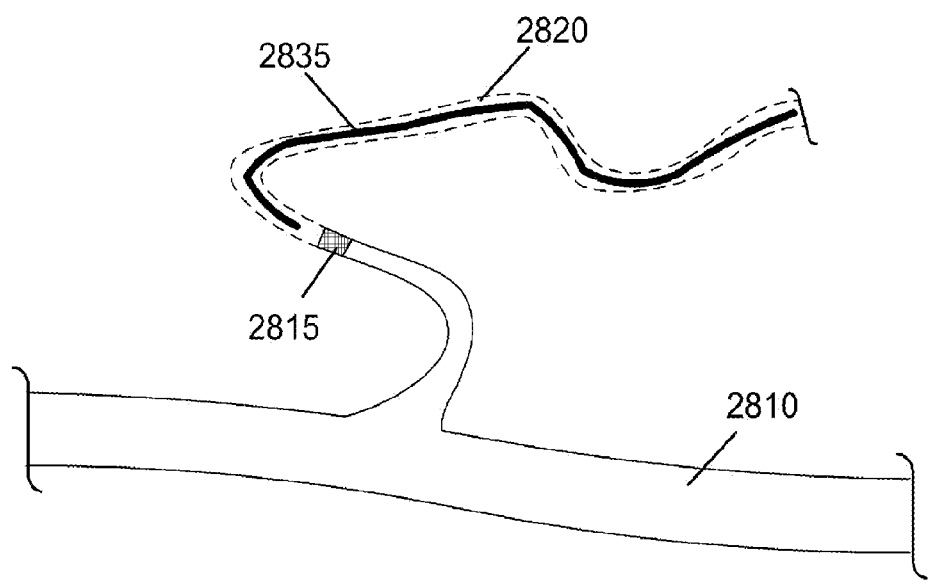

FIG. 28B exhibits the ability to recreate the path based on the measurements made in FIG. 28A.

Figure 29A:
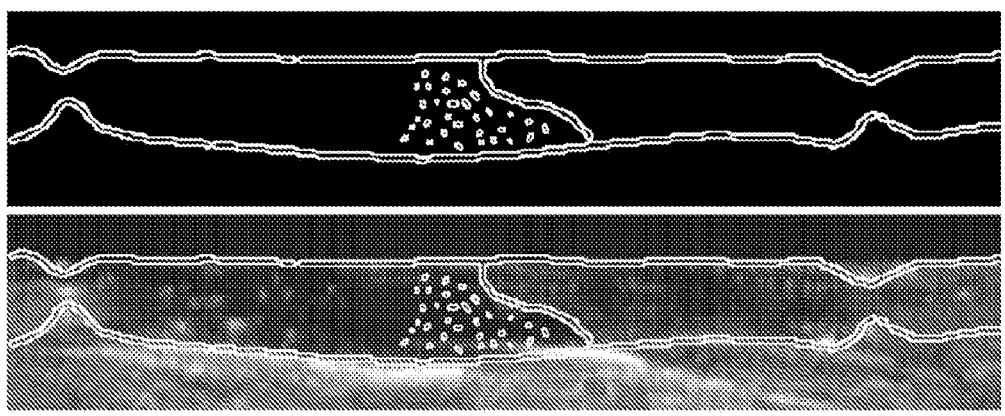
Figure 29B:
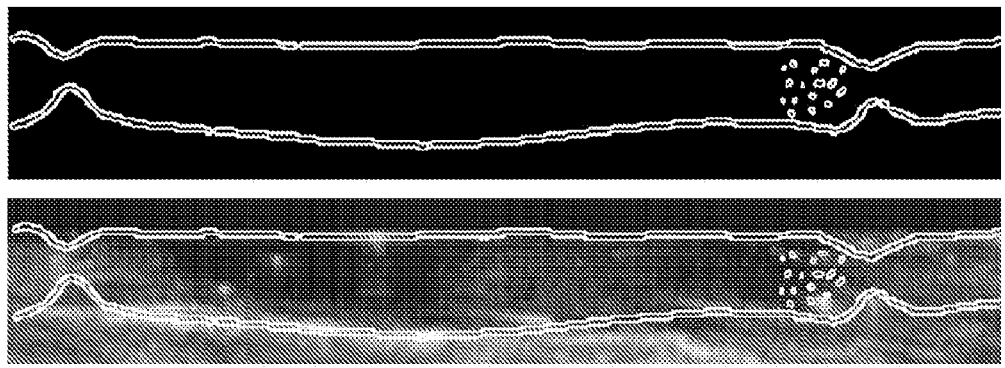

FIGS. 29A and 29B show the clearance of a thrombosis in the vein of a rabbit using the magnetomotive stator system and magnetic nanoparticles.

Figure 30:
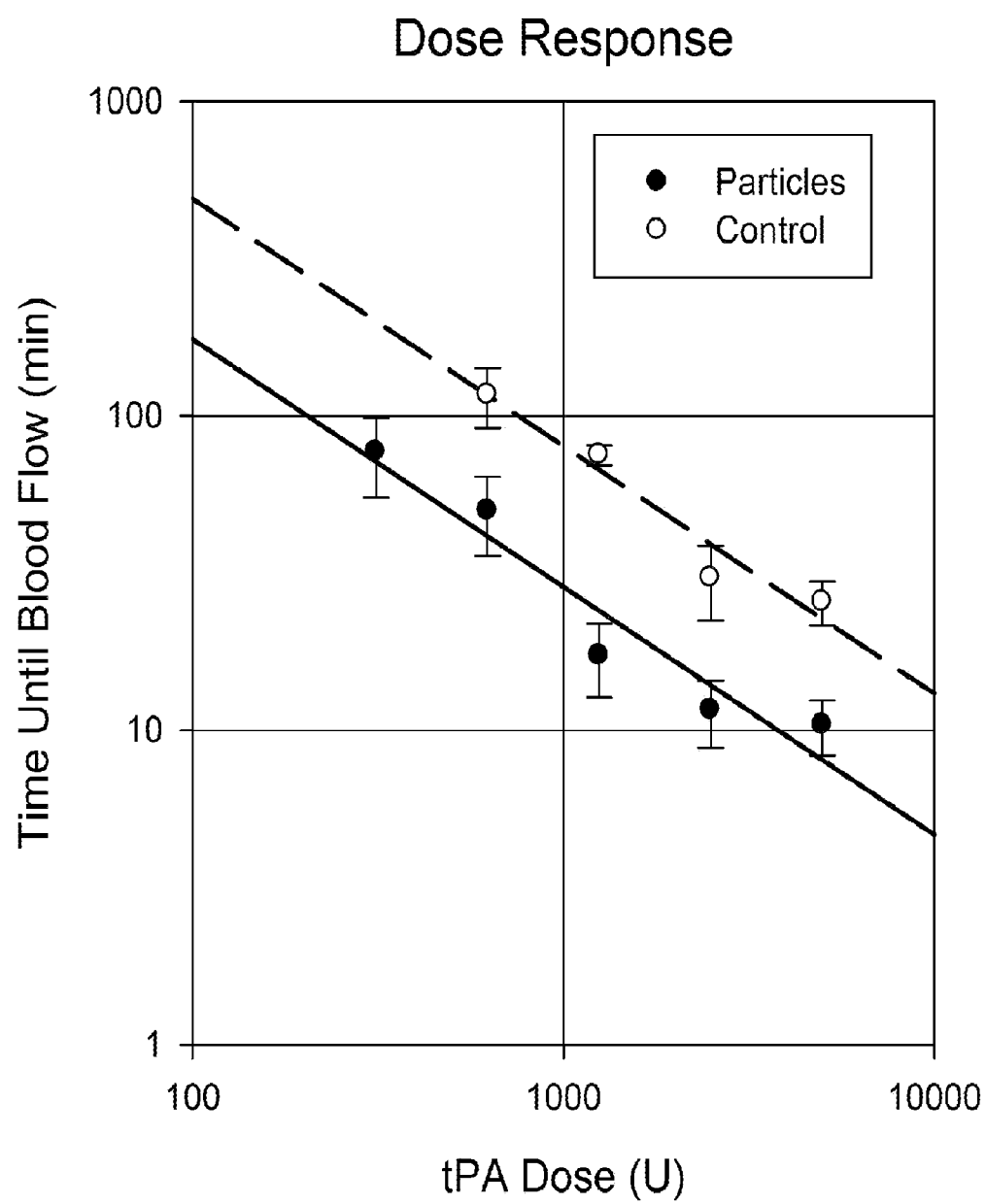

FIG. 30 illustrates the dosage response curve of tPA using the magnetomotive stator system showing both reduced time to increase blood flow in a rabbit, and reduced amount of tPA required to produce the same result.

DETAILED DESCRIPTION

Abbreviations and Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. The nomenclatures utilized in connection with, and the laboratory procedures and techniques of medicinal and pharmaceutical chemistry described herein are those well known and commonly used in the art. Standard techniques are used for pharmaceutical preparation, formulation, and delivery, and treatment of patients. Other chemistry terms herein are used according to conventional usage in the art, as exemplified by The McGraw-Hill Dictionary of Chemical Terms (Parker, S., Ed., McGraw-Hill, San Francisco (1985)). Other terms with respect to magnetic nanoparticle dynamics herein are used according to conventional usage in the art, as exemplified in the textbook Ferrohydro-Dynamics (R. E. Rosensweig, Dover Publications, New York, (1985)).

As utilized in accordance with the present disclosure, the following terms, unless otherwise indicated, shall be understood to have the following meanings:

Patient: As used herein, the term patient includes human and veterinary subjects.

Thrombolytic drug: As used herein, a "thrombolytic drug" includes tissue plasminogen activator (tPA), plasminogen, streptokinase, urokinase, recombinant tissue plasminogen activators (rtPA), alteplase, reteplase, tenecteplase, and other drugs capable of degrading a blood clot or arteriosclerotic plaque. The term "thrombolytic drugs" includes the drugs above alone or co-administered with warfarin and/or heparin.

Magnetic Nanoparticle: As used herein, the term "magnetic nanoparticle" refers to a coated or uncoated metal particle having a diameter between about 1 nm to about 1000 nm, including about 10 nm to about 200 nm, and about 15 nm to about 150 nm, and about 20 nm to about 60 nm, and all integers between 1 and 1000, e.g., 1, 2, 3, 4, 5, . . . 997, 998, 999, and 1000. One of skill in the art can determine appropriate sizes of magnetic nanoparticles depending on the therapeutic target of the system, e.g., very small vessels can accept smaller nanoparticles and larger parts of a circulatory system can accept larger nanoparticles. Examples of such magnetic nanoparticles include superparamagnetic iron oxide nanoparticles. The particles may be made of magnetite and, optionally, be coated with any one or a combination of the following materials: (1) coatings which enhance the behavior of the particles in blood by making them either hydrophilic or hydrophobic; (2) coatings which buffer the particles which optimize the magnetic interaction and behavior of the magnetic particles; (3) contrast agent or agents which allow visualization with magnetic resonance imaging, X-ray, Positron Emission Tomography (PET), or ultrasound technologies; (4) drugs which accelerate destruction of a circulatory system blockage; and (5) thrombolytic drugs. Examples of both coated and uncoated magnetic nanoparticles and methods of making such magnetic nanoparticles are well known in the art, for example those described in U.S. Pat. Nos. 5,543,158, 5,665,277, 7,052,777, 7,329,638, 7,459,145, and 7,524,630. See also Gupta et al., Biomaterials, Volume 26, Issue 18, Jun. 2005, Pages 3995-4021. Those of skill in the art will recognize many other combinations of features that can be included in magnetic nanoparticles useful in the present invention while retaining the magnetic properties for use in the present invention.

Fluid Obstruction: As used herein, the term "fluid obstruction" means a blockage, either partial or complete, that impedes the normal flow of fluid through a circulatory system, including the venous system, arterial system, central nervous system, and lymphatic system. Vascular occlusions are fluid obstructions that include, but are not limited to, atherosclerotic plaques, fatty buildup, arterial stenosis, restenosis, vein thrombi, cerebral thrombi, embolisms, hemorrhages, other blood clots, and very small vessels. Sometimes, fluid obstructions are generally referred to as "clots".

Substantially Clear: As used herein, the term "substantially clear" means removal of all or part of a fluid obstruction that results in increased flow of fluid through the circulatory system. For example, creating a pathway through or around a thrombus that blocks a vein so that blood can flow through or around the thrombus "substantially clears" the vein.

Very Small Vessel: As used herein, the term "very small vessel" means a circulatory system fluid pathway having a diameter from about 1 µm to about 10 µm.

Increased Fluid Flow: As used herein, the term "increased fluid flow" means increasing the throughput of a blocked circulatory system from zero to something greater than zero. In flowing circulatory systems, the term "increased fluid flow" means increasing the throughput from a level prior to administration of a magnetic nanoparticle in a patient to a level greater than that original fluid flow level.

Agglomerate: As used herein, the term "agglomerate" means rotational clustering and chaining of a group of individual magnetic rotors in a manner to develop "rods" from the magnetic nanoparticles as described herein with respect to FIG. 15. Such a group of rotating rotors forms an ensemble in which each individual rotor generally rotates simultaneously and travels in the same direction as a group. The application of the combined field and gradient over time is the manner of assembling the rods. Such a group comprises characteristics different than what can be expected of individual rotors acting alone and creates hydrodynamic forces in a fluid stream or still fluid to create turbulence or enhance the diffusion of a composition or liquid in the fluid stream or still fluid.

Treatment: As used herein, "treatment" is an approach for obtaining beneficial or desired clinical results. For purposes of this invention, beneficial or desired clinical results include, but are not limited to, one or more of the following: improvement or alleviation of any aspect of fluid obstruction in the circulatory system including, but not limited to, fluid obstructions (e.g., stroke, deep vein thrombosis), coronary artery disease, ischemic heart disease, atherosclerosis, and high blood pressure.

Drug, Compound, or Pharmaceutical Composition: As used herein, the terms "pharmaceutical composition," "compound," or "drug" refer to a chemical compound or composition capable of inducing a desired therapeutic effect when properly administered to a patient, for example enzymatic degradation of a thrombus or atherosclerotic plaque.

Effective Amount: An "effective amount" of drug, compound, or pharmaceutical composition is an amount sufficient to effect beneficial or desired results including clinical results such as alleviation or reduction in circulatory system fluid blockage. An effective amount can be administered in one or more administrations. For purposes of this invention, an effective amount of drug, compound, or pharmaceutical composition is an amount sufficient to treat (which includes to ameliorate, reducing incidence of, delay and/or prevent) fluid blockage in the circulatory system, including vascular occlusions in the head and extremities. The effective amount of a drug includes coated or uncoated magnetic nanoparticles formulated to be administered to a patient. The effective amount can also include a drug, compound, or pharmaceutical composition such as thrombolytic drugs. Thus, an "effective amount" may be considered in the context of administering one or more therapeutic agents, and a single agent may be considered to be given in an effective amount if, in conjunction with one or more other agents, a desirable result may be or is achieved.

Reducing Incidence: As used herein, the term "reducing incidence" of fluid blockage in the circulatory system means any of reducing severity (which can include reducing need for and/or amount of (e.g., exposure to) drugs and/or therapies generally used for these conditions, including, for example, tPA), duration, and/or frequency (including, for example, delaying or increasing time to displaying symptoms of circulatory system blockage). As is understood by those skilled in the art, individuals may vary in terms of their response to treatment, and, as such, for example, a "method of reducing incidence of fluid blockage" in an patient reflects administering the effective amount of the magnetic nanoparticles, whether or not in combination with a drug, compound, or pharmaceutical composition, based on a reasonable expectation that such administration may likely cause such a reduction in incidence in that particular individual.

Ameliorating: As used herein, the term "ameliorating" one or more symptoms of circulatory system blockage means a lessening or improvement of one or more symptoms of circulatory system blockage as compared to not administering a magnetic nanoparticle, whether or not in combination with a drug, compound, or pharmaceutical composition, using the system described herein. "Ameliorating" also includes shortening or reduction in duration of a symptom.

Delaying: As used therein, "delaying" the development of a symptom related to circulatory system blockage means to defer, hinder, slow, retard, stabilize, and/or postpone progression of the related symptoms. This delay can be of varying lengths of time, depending on the history of the disease and/or individuals being treated. As is evident to one skilled in the art, a sufficient or significant delay can, in effect, encompass prevention in that the individual does not develop symptoms associated with circulatory system blockage. A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

Pharmaceutically Acceptable Carrier: As used herein, "pharmaceutically acceptable carrier" includes any material which, when combined with a magnetic nanoparticle and/or an active ingredient, is non-reactive with the subject's immune system and allows the active ingredient to retain biological activity. Examples include, but are not limited to, any of the standard pharmaceutical carriers such as a phosphate buffered saline solution, water, emulsions such as oil/water emulsion, and various types of wetting agents. Exemplary diluents for parenteral administration are phosphate buffered saline or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

Pharmaceutically Acceptable: The terms "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

Magnetomotive Stator System and Methods for Wireless Control of Magnetic Rotors

This present invention relates to a system and methods for the physical manipulation of free magnetic rotors using a remotely placed magnetic field-generating stator. In particular, the invention relates to the control of magnetic nanoparticles to increase contact of a therapeutic target in a circulatory system with a pharmaceutical compound which can result in increased fluid flow and the substantial clearance of fluid blockages of the circulatory system. In various aspects, the system enhances diffusion of thrombolytic drugs and uses permanent magnet-based or electromagnetic field-generating stator sources. Magnetic fields and gradients are used to act on magnetic nanoparticle agglomerates and magnetic thrombectomy devices to reduce circulatory system blockages, including vascular occlusions, in a patient. In various aspects, the system and methods of the present invention can be used to treat fluid blockages of the circulatory system in the head (in particular, the brain) and in the extremities of the body, such as the vasculature of arms and legs.

The present invention consists of a magnetically produced scouring process generated by magnetic particles and/or magnetically-enabled thrombectomy devices acting on fluid blockage in combination with the mechanically enhanced dissolving process of the thrombolytic agent that is used. The magnetic actions are derived from a rotating magnetic field from an external source which also provides a pulling magnetic gradient that is not rotating. This provides forces and actions on circulatory system blockages generally without mechanical invasion of the location. The system and methods of the present invention greatly increase drug interaction with the target circulatory system blockage, and can leave residue that may be collected magnetically, and also which in the process does not damage venous walls or valves. Another feature of the present invention is the ability to use drug and stirring conditions so that essentially all of the residue that is removed forms a small soft clump with the nanoparticles that can easily be captured by a tiny magnet on the tip of a guide wire. To achieve these qualities the present invention uses a rotating magnetic field in combination with a directed magnetic gradient to act on magnetic nanoparticles or magnetically-enabled fluid blockage clearing devices.

In one aspect, the rotating field is generated by mechanically rotating a strong permanent magnet having an orientation that rotates the field at the target site, and at the same time presents a steady magnetic gradient in a desired direction. In another aspect, two or more magnetic coils can be used with appropriate phasing to provide rotating fields with the gradient. When three or more coils are used, at least two coils can have axes having some perpendicular component on each other to provide additional magnetic spatial and timing features. For instance, two coils can have perpendicular axes and one can employ current lagging the other by 90 degrees to create a rotating field at the target position. A third coil can be located and oriented to provide appropriate gradients at the target site, as well as independent functions such as modulation.

With electronic controls of the currents, a wide array of fields and gradients can be applied with a large number of time-related events. The result of the basic rotating field with gradient applied to a slurry of nanoparticles is to provide a very specific type of arrangement of the grouping: that is the "agglomeration" of magnetic nanoparticles that in the system and methods of the present invention cause them to form aligned rods of approximately 2 mm in length or less.

A field of about 0.02 Tesla at the target site, in combination with a gradient of about 0.4 Tesla/meter, will create the desired agglomeration of magnetic nanoparticles—separated nanoparticle rods of length varying approximately from one to two millimeters in length. These agglomerates remain largely intact in vitro and in vivo, but are sufficiently flexible to provide "soft brushing" when rotated. It has been observed that on rotation these rods "walk" along a surface in a vessel, and when in contact with a fluid blockage, such as a blood clot, remove minute particles of the clot material with the aid of the thrombolytic drug. They softly "scrub" off fractions of the clot material continuously, in some cases without residue components of significant size. In other cases, depending on the type and location of obstruction, the delivery of thrombolytic drugs can be timed so that the residue ends up in a soft small magnetic ball, which can be captured magnetically and removed. Ultrasound and other imaging technologies can be used to visualize the progress of such scrubbing, for example transcranial ultrasound could be used to confirm clot destruction visually in a cranial embolism or stroke. The use of contrast agents and other agents that enhance visualization of the magnetic nanoparticles are well known in the art.

Using the same rotating magnetic field and gradient apparatus, it has been observed that similar fields of 0.02 Tesla with gradients of 0.4 Tesla/meter at the target site allow precise control over the rotation of a small magnetic ball approximately 1.5 mm in diameter. It has been found that with proper alignment of the magnetic gradient, the ball-like structure can be made to navigate the vessels and increase drug mixing at the blockage. In a similar manner, coatings that comprise thrombolytic agents and/or surface features can be added to enhance destruction of a blockage.

The numerical details of this process can vary, depending on the particular nature of the circulatory system blockage, the thrombolytic drug, and the design of the magnetically-enabled thrombectomy devices. Rotational frequencies (from about 1 to about 30 Hz, including from about 3 to about 10 Hz) are effective with a range of magnetic field magnitudes that can be generated by magnets (from about 0.01 to about 0.1 Tesla), all in a volume of about one cubic foot, or by coils with somewhat larger volume. Gradient strength can be in a range from about 0.01 Tesla/m to about 5 Tesla/m. The gradient direction generally centers on the center of mass for a permanent magnet, and using an electromagnet can center on one of the coils, and in combination, can center between one or more of the coils.

Fluid Blockages of the Circulatory System

Parts of the body where fluid blockages of the circulatory system occur include the legs and the brain. Two major hydrodynamic properties of such blockage are observed in the vasculature: low blood flow or total blockage. In either case, existing modes of delivery of drugs for dissolving occlusions at surfaces or mechanical removal of, for example, thrombus material cannot effectively clear a degraded and impeding layer on a clot surface to be removed to allow fresh drug interaction with an underlayer. This often results in dangerous components moving downstream which can result in a more dangerous blockage or death. In a typical flow situation, there are locations where the flow does not effectively penetrate or target the intended site. In other situations it is not possible to navigate a thrombectomy device to the target due to smallness (e.g., a very small vessel) or complexity of the three-dimensional shape of the occluded vessel.

Different thrombolytic drugs have been used in the thrombolytic process. For example, streptokinase is used in some cases of myocardial infarction and pulmonary embolism. Urokinase has been used in treating severe or massive deep venous thrombosis, pulmonary embolism, myocardial infarction and occluded intravenous or dialysis cannulas. Tissue Plasminogen Activator ("tPA" or "PLAT") is used clinically to treat stroke. Reteplase is used to treat heart attacks by breaking up the occlusions that cause them. In the case of thrombectomy devices, products are manufactured by several companies and employ a range of technologies, including mechanical extraction (Arrow International, Inc., Edward Lifesciences), venturi jet-based mechanism (Boston Scientific, Possis Medical, Inc.), low-power acoustic (OmniSonics Medical Technologies, Inc.), and abrasion and aspiration (ev3).

In the case of stroke, tPA is used successfully in many cases, but in many cases the effect of the drug is to leave downstream residue in clumps large enough to cause further blockage and sometimes death. In addition, the normal thrombolytic dosage administered to patients is related to increased bleeding in the brain. In most cases, the effectiveness of chemical interaction of the thrombolytic agent with the blockage is slow and inefficient, leaving incomplete removal of the blockage. In blockages in the extremities, mechanical means of stirring and guiding the drug are limited, often difficult, and can be dangerous. In another difficult issue, venous valves in the region of the procedure are damaged or not made blockage free in procedures currently used. The present invention provides new systems and methods for significant improvement in dealing with these major obstacles in treating occlusions of the blood flow.

Magnetomotive Stator System

A therapeutic system is provided comprising (a) a magnet having a magnetic field and a gradient for controlling magnetic rotors in a circulatory system, and (b) a controller for positioning and rotating the field and the gradient in a manner to agglomerate and traverse the magnetic rotors with respect to a therapeutic target in the circulatory system. Using the therapeutic system, contact of the therapeutic target with a pharmaceutical composition in the circulatory system is increased. In various aspects, the pharmaceutical composition can be attached to the magnetic rotor, and in other aspects can be administered to the circulatory system separate from the magnetic rotors. In certain instances, the pharmaceutical composition can be a thrombolytic drug.

Therapeutic targets of the system can include fluid obstructions such as atherosclerotic plaques, fibrous caps, fatty buildup, coronary occlusions, arterial stenosis, arterial restenosis, vein thrombi, arterial thrombi, cerebral thrombi, embolism, hemorrhage and very small vessels. In various aspects, the circulatory system is vasculature of a patient, in particular a human patient.

In various embodiments, the therapeutic system comprises a permanent magnet coupled to a motor, and the controller controls a motor to position the magnet at an effective distance, an effective plane with respect to the therapeutic target, and rotates the magnet at an effective frequency with respect to the therapeutic target. In various embodiments, the therapeutic system comprises an electromagnet having a magnetic field strength and magnetic field polarization driven by electrical current, and the controller positions the electromagnet at an effective distance, an effective plane with respect to the therapeutic target, and rotates the magnetic field of the electro-magnet by adjusting the electrical current.

The therapeutic system can further include a display for viewing the magnetic rotors and therapeutic target, and a user interface for controlling the magnetic rotors, such that a user controls the magnetic rotors to clear the therapeutic target by adjusting a frequency of the rotating magnetic field, a plane of the rotating magnetic field with respect to the therapeutic target, and a distance of the rotating magnetic field with respect to the therapeutic target. In various aspects, the therapeutic target can be a thrombosis in a human blood vessel. In various aspects, the magnetic rotors can be magnetic nanoparticles injected into the circulatory system.

In various aspects of the invention, the magnetic rotors traverse through the fluid in the circular motion by repeatedly (a) walking end over end along the blood vessel away from the magnetic field in response to the rotation of the rotors and an attractive force of the magnetic field, and (b) flowing back through the fluid towards the magnetic field in response to the rotation of the rotors and the attractive force of the magnetic field.

In various aspects, the obstruction to be treated using the system is a thrombosis in a human blood vessel, and the magnetic rotors are formed by magnetic nanoparticles injected into the circulatory system. In the system, the magnetic rotors can traverse through the fluid in the circular motion by repeatedly (a) walking end over end along the blood vessel away from the magnetic field in response to the rotation of the rotors and an attractive force of the magnetic field, and (b) flowing back through the fluid towards the magnetic field in response to the rotation of the rotors and the attractive force of the magnetic field.

In another embodiment, a system is provided for increasing fluid flow in a circulatory system comprising a magnet having a magnetic field for controlling magnetic rotors in the fluid, a display for displaying, to a user, the magnetic rotors and the therapeutic target in the fluid, and a controller, in response to instructions from the user, controlling the magnetic field to: (a) position the magnetic rotors adjacent to the therapeutic target, (b) adjust an angular orientation of the magnetic rotors with respect to the therapeutic target, and (c) rotate and traverse the magnetic rotors through the fluid in a circular motion to mix the fluid and substantially clear the therapeutic target.

In various aspects, the display can display real time video of the magnetic rotors and the therapeutic target, and the display can superimpose a graphic representative of a rotation plane of the magnetic field and another graphic representative of the attractive force of the magnetic field on the real time video. In another aspect, the magnet can be a permanent magnet coupled to a motor and a movable arm, and the controller can include a remote control device for a user to manipulate the position, rotation plane and rotation frequency of the magnetic field with respect to the therapeutic target.

In another aspect, the display can adjust the graphics in response to instructions given by the user through the remote control device. In various aspects, the magnet can be an electro-magnet coupled to a motor and a movable arm, and the controller can perform image processing to identify the location, shape, thickness and density of the therapeutic target, and automatically manipulates the movable arm to control the position, rotation plane and rotation frequency of the magnetic field to clear the therapeutic target.

In yet another aspect, the magnetic rotors can be formed by magnetic nanoparticles which combine in the presence of the magnetic field. In another aspect, the fluid can be a mixture of blood and a thrombolytic drug, the blood and thrombolytic drug being mixed by the circular motion of the magnetic rotors to erode and clear the therapeutic target. In yet another aspect, the circular motion of the magnetic rotors can redirect the thrombolytic drug from a high flow blood vessel to a low flow blood vessel which contains the therapeutic target.

Figure 1A:
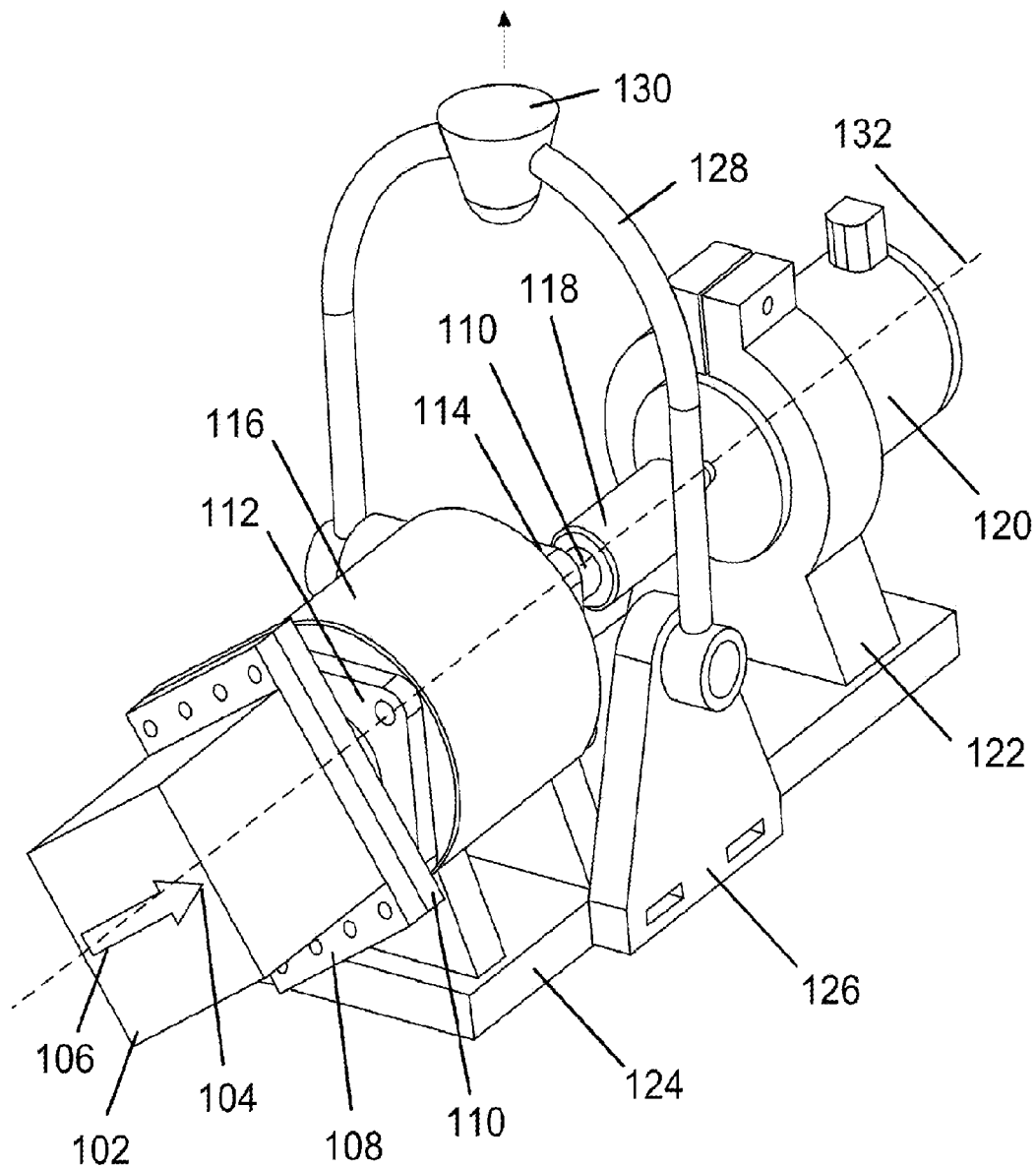
FIGS. 1A and 1B show an example of a permanent-magnet stator system whose magnet's North-South pole rotates in a plane parallel to the system's front face, which is driven by a single motor.
Figure 1B:
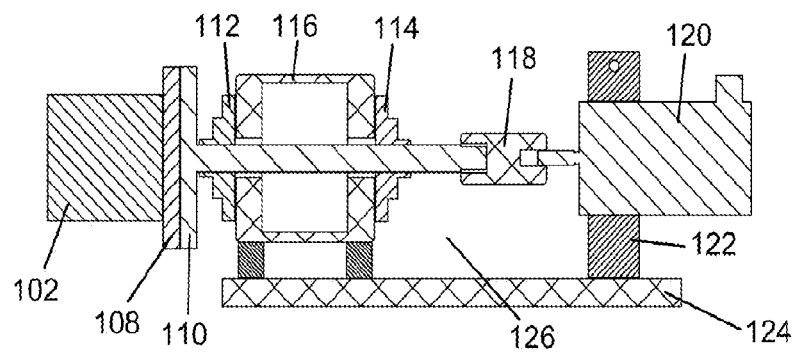

One embodiment of such a magnetomotive stator system is illustrated in FIG. 1A (isometric view) and FIG. 1B (cross-section view). The operation of components is shown for this system involving rotation about a single axis 132. The permanent magnet cube 102 possesses a North 104 and a South 106 magnetic pole. The permanent magnet 102 illustrated here measures 3.5 inches on each side. Note that the permanent magnet 102 may be composed of a number of permanent magnet materials, including Neodymium-Boron-Iron and Samarium-Cobalt magnetic materials, and may be made much bigger or smaller. The shape of the permanent magnet 102 does not need to be a cube. Other configurations of the permanent magnetic material are better in shaping the field so that aspects of the magnetic field and gradient are optimized in terms of strength and direction. In other embodiments, the permanent magnetic material may be configured in a way to make the system more compact. A cylinder composed of permanent magnet material is one such example. However, simple rectangular and cubical geometries tend to be cheaper.

The face of the permanent magnet 102 in which the North 104 and South 106 poles reside is glued or otherwise fastened to a mounting plate 108. The mounting plate can be composed either of magnetic or of nonmagnetic material. Optionally magnetic materials can be used to strengthen the magnetic field for some configurations of the permanent magnetic material. However, nonmagnetic mounting plates are easier to affix to the permanent magnet 102.

This mounting plate 108 is attached to a flange 110 which passes through a first bearing 112 and a second bearing 114, both of which are supported by the bearing mounting structure 116. Most standard bearings are at least partially magnetic. In these cases, the flange 110 should be constructed from a nonmagnetic material to ensure the magnetic field does not travel efficiently from the flange 110 into the bearings 112 and 114. If this were to happen, the bearings would encounter more friction due to the magnetic attraction of the flange 110 to the bearings 112 and 114.

The end of the flange 110 is connected to a coupling 118, which connects to a drive motor 120. The motor may be a DC or an AC motor. A high degree of precision is capable with a servo motor, although these motors tend to cost more. In some cases, a step-down gearbox may be necessary to spin the permanent magnet 102 at the desired frequency, given that most motors typically spin faster than is desired for the wireless control of magnetic rotors as used in the present invention.

The drive motor 120 is attached to a motor support structure 122 which affixes the drive motor 120 to a platform 124. Attached to the platform 124 is a suspension mounting bracket 126 (located but not shown in FIG. 1B), which is connected to a suspension arm 128. The suspension arm 128 possesses an attachment joint 130. The suspension arm 128 may be suspended from overhead, from the side, or from the bottom, depending on the best placement of the magnet stator system.

Operation of the Magnetomotive Stator System

Figure 2:
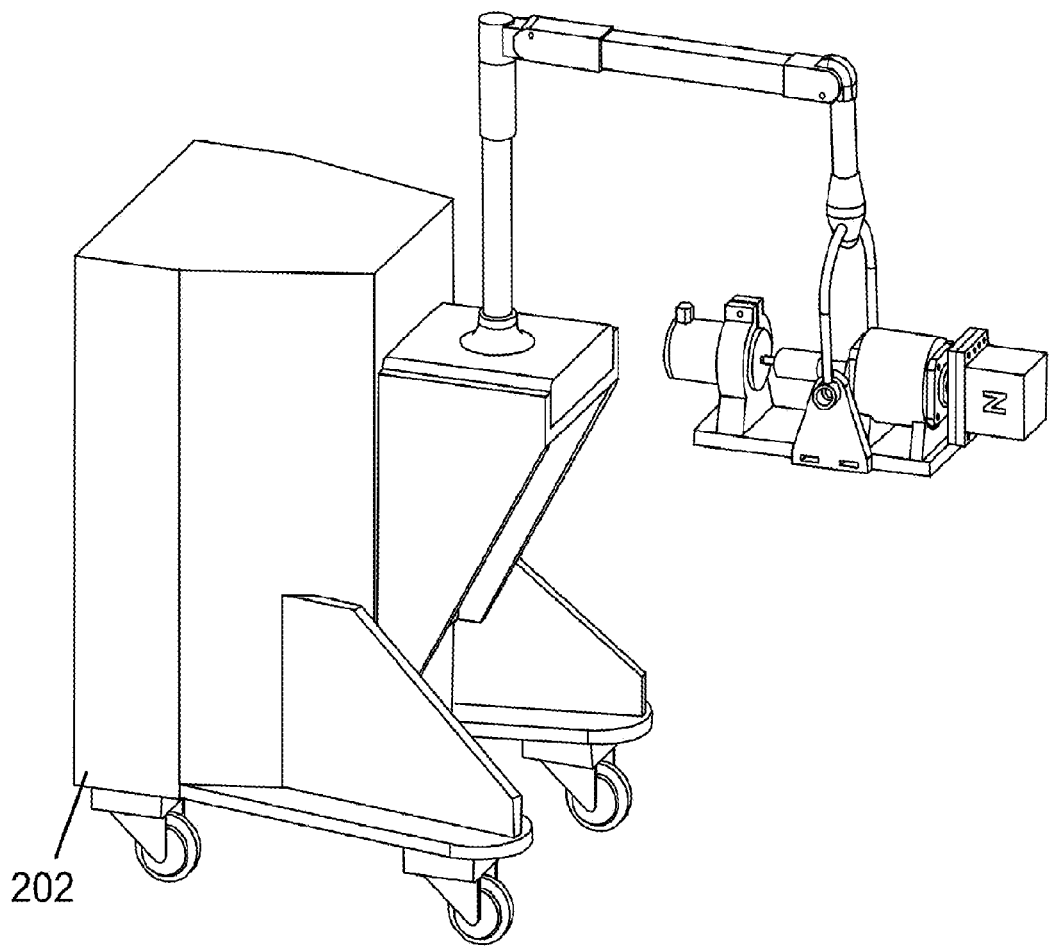
FIG. 2 shows a portable positioner cart to which the magnet system of FIG. 1 is attached.
Figure 6A:
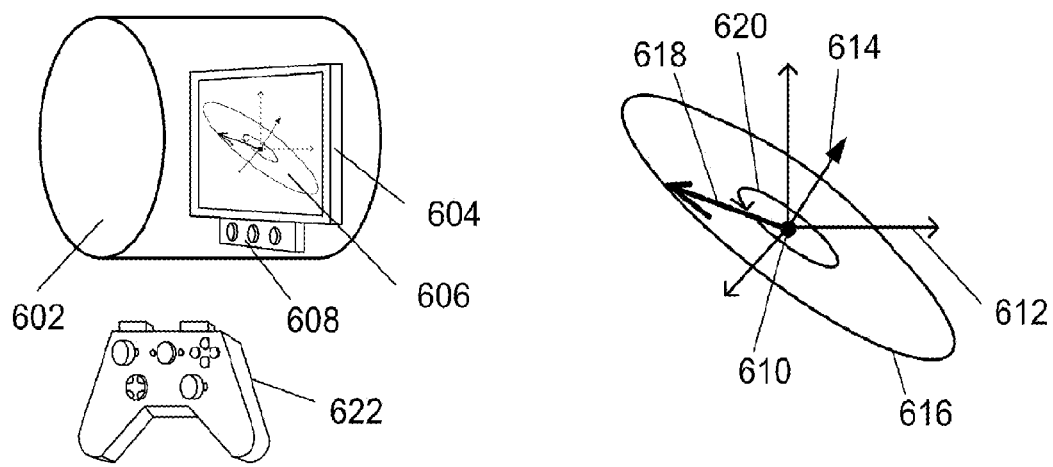
FIGS. 6A to 6C show an example of a user control interface for a magnetic stator system.
Figure 6B:
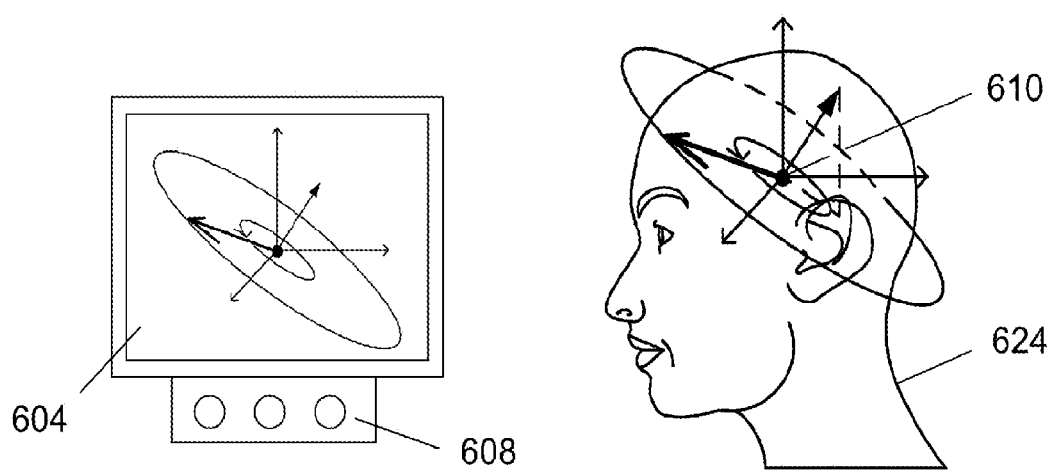
Figure 6C:
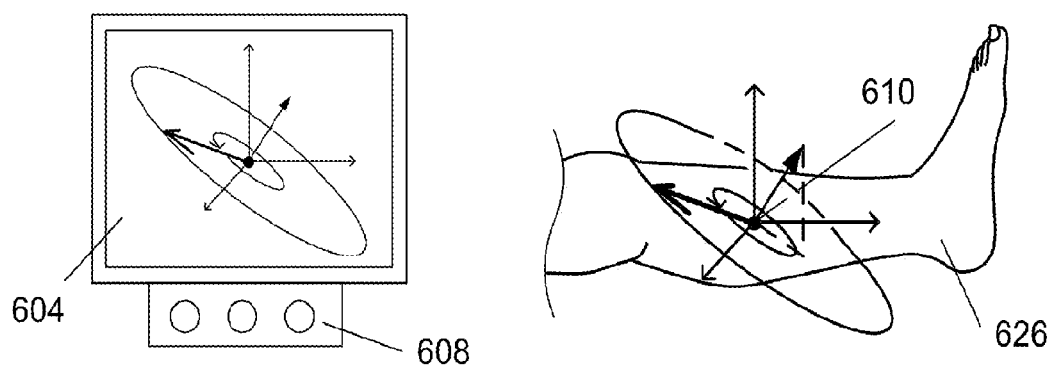

The magnetomotive stator system (shown in FIG. 6, 602) can be positioned by the use of a portable support base 202 as shown in FIG. 2. Once in place, and as shown in FIG. 6, a computer control panel 604 with a computer display 606 and user control buttons 608 are used to specify the orientation of the magnetic rotation plane 616 at the user-defined point in space 610. The field and gradient are manipulated in the physical space 610. The rotation plane's normal vector 614 is specified by the user in the global coordinate system 612 at the point in space 610, using either the control button 608 or a handheld controller 622. Within the magnetic rotation plane 616 is the initial orientation of the magnetic field 618, which may be set automatically by the computer. The user specifies the direction of the magnetic field rotation 620 in the magnetic rotation plane 616.

Figure 7:
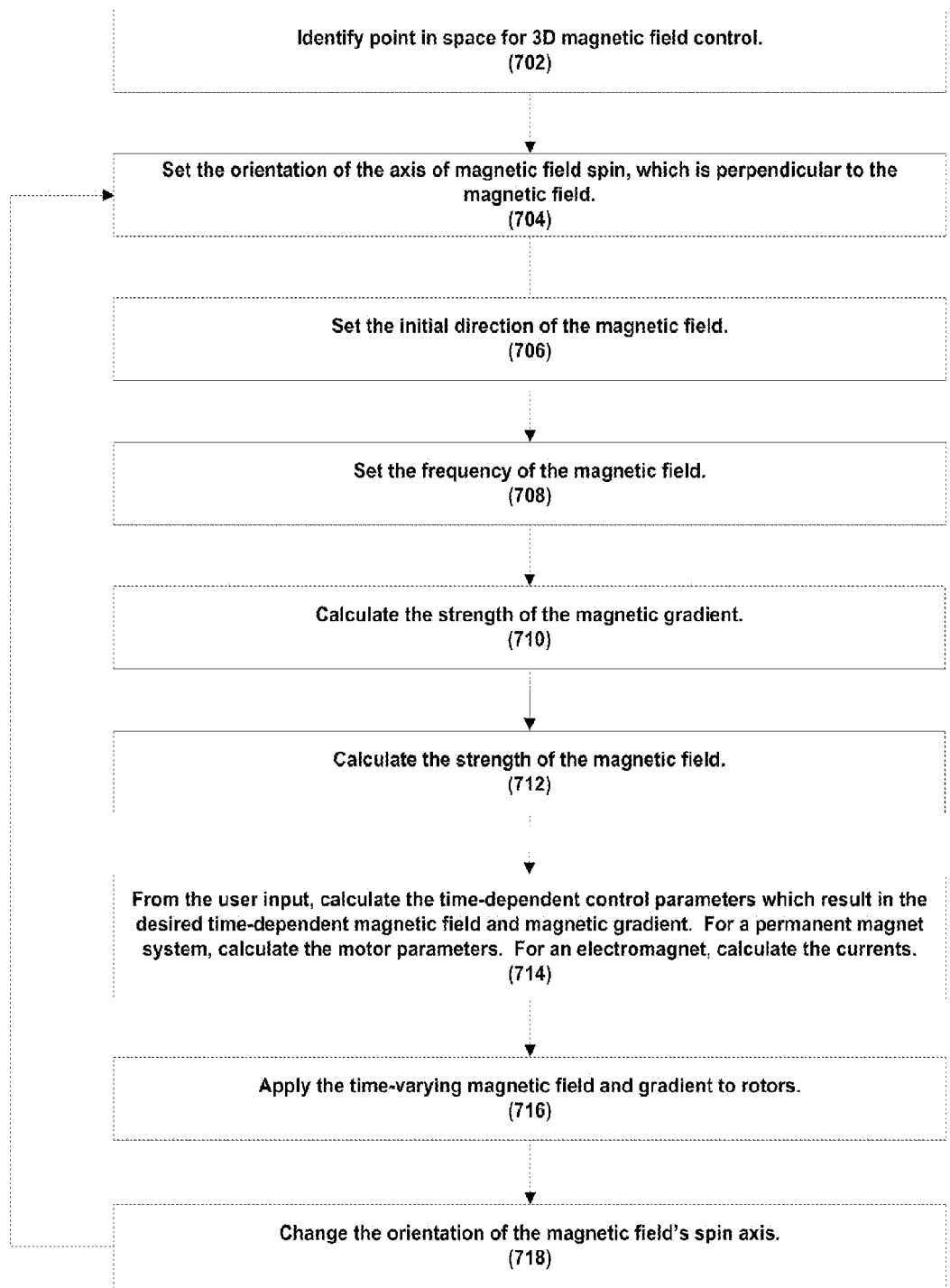
FIG. 7 shows an algorithm example that will allow a user to define a field rotation in space for the wireless control of magnetic rotors.

The computer process is illustrated in FIG. 7. The identification of the point in space 610 corresponds to 702 in the algorithm. Likewise, the specification of the rotation plane's normal vector 614 corresponds to 704 in the algorithm. Using a right-handed coordinate system, the field rotates clockwise around the normal vector 614. The computer automatically sets the initial direction of the magnetic field 618, which is illustrated in the computer algorithm as 706. The user sets the frequency of field rotation 708 within the magnetic rotation plane 616. The strength of the magnetic gradient is calculated 710 as is the strength of the magnetic field 712. From these data, the control parameters are calculated for the magnet system 714. For a permanent magnet system, the control parameters correspond to the rotation speed of the drive motor(s). For an electromagnet system, the control parameters describe the change in current in time. Once calculated, the magnetomotive stator system is turned on 716. If it is desired that the magnetic rotation plane 616 be changed, which is depicted in step 718 of FIG. 7, the algorithm loops to the input for the rotation plane's normal vector 614, which corresponds to 704 in the algorithm.

Assuming the magnetomotive stator system of FIG. 1A is attached to the portable support base 202, the platform 124 may be oriented by the user through the suspension mounting brackets 126 which are attached to the suspension arm 128, which is itself attached to the suspension arm attachment joint 130. The suspension arm attachment joint 130 connects to the arm positioner which connects to the portable support base 202. The suspension arm attachment joint 130 allows rotation of the magnet system about the end of the arm positioner. The suspension arm attachment joint 130 also allows the platform base 124 to be rotated in the plane perpendicular to that allowed by the suspension arm attachment joint 130. The motor 120, which is attached to the platform base 124 via the motor support structure 122, spins at the desired frequency. This motion is coupled to the mounting flange 110 via the drive coupling 118. The first bearing 112 and the second bearing 114 allow for the mounting flange 110 to rotate smoothly. These bearings are affixed to the platform 124 via the bearing mounting structure 116. The spinning flange 110 is rigidly attached to the magnet mounting plate 108, which is attached to the permanent magnet 102. Thus, the motor 120 spin is transmitted to the permanent magnet 102. The location of the North magnetic pole 104 and the South magnetic pole 106 at the ends of the permanent magnet 106, results in the desired magnetic field rotation plane 616. In this magnetic field rotation plane 616, the magnetic field rotates parallel to the front face of the magnet for all points located on the central drive axis 132.

For the manipulation of magnetic particles within the body, the user-defined point in space 610 may be inside the head 624 for ischemic stroke therapies in which magnetite particles are manipulated to rapidly and safely destroy clots. Likewise, the user-defined point in space 610 may be inside the leg 626 for deep-vein thrombosis therapies in which magnetite particles are manipulated to rapidly and safely destroy clots.

In the example of magnetic particle manipulation, the magnetic particle 802, which possesses a particle North magnetic pole 804 and a particle South magnetic pole 806, is rotated by the clockwise rotating magnetomotive-generated magnetic field 812 relative to the particle reference coordinate system 808. This results in the magnetic particle spinning in the direction of the clockwise rotation angle 810. When a magnetic gradient 814 is applied and a surface 816 is present, the clockwise rotating magnetomotive-generated magnetic field 812 results in traction against the surface, resulting in translation 818 to the right.

In the presence of a fluid 820 contained within an enclosing region 822, the manipulation of the magnetic particles when combined with the magnetic gradient 814 results in circulating fluid motion 824. When used to destroy vessel obstructions 830 within a blood vessel 828, which contains blood 826, the magnetomotive-generated mixing results in better mixing of the clot-busting (thrombolytic) drug. This allows for the thrombolytic dose to be lowered which, by reducing the bleeding associated with higher doses of thrombolytic drugs, results in a safer procedure. It also speeds the thrombolytic process.

Therefore, methods are also provided for increasing fluid flow in a circulatory system comprising: (a) administering a therapeutically effective amount of magnetic rotors to the circulatory system of a patient in need thereof, and (b) applying a magnet to the patient, the magnet having a magnetic field and a gradient for controlling the magnetic rotors in a circulatory system, and (c) using a controller for positioning and rotating the field and the gradient in a manner to agglomerate and traverse the magnetic rotors with respect to a therapeutic target in the circulatory system of the patient, wherein contact of the therapeutic target with a pharmaceutical composition in the circulatory system is increased and fluid flow is increased.

In various aspects, the pharmaceutical composition can be attached to the magnetic rotor. In other aspects, the pharmaceutical composition can be administered to the circulatory system of the patient separate from the magnetic rotors. In various embodiments, the pharmaceutical composition is a thrombolytic drug.

In various aspects, therapeutic target can be a fluid obstruction such as atherosclerotic plaques, fibrous caps, fatty buildup, coronary occlusions, arterial stenosis, arterial restenosis, vein thrombi, arterial thrombi, cerebral thrombi, embolism, hemorrhage and very small vessel. In yet another aspect, the circulatory system is vasculature of a patient, particularly a human patient.

In yet another aspect, the magnet can be a permanent magnet coupled to a motor, and the controller can control a motor to position the magnet at an effective distance, an effective plane with respect to the therapeutic target, and rotates the magnet at an effective frequency. In another aspect, the magnet can be an electromagnet having a magnetic field strength and magnetic field polarization driven by electrical current, and the controller can position the electromagnet at an effective distance, an effective plane with respect to the therapeutic target, and rotates the magnetic field of the electro-magnet by adjusting the electrical current.

The system of the method can further include a display for viewing the magnetic rotors and therapeutic target, and a user interface for controlling the magnetic rotors, wherein a user controls the magnetic rotors to increase contact of the therapeutic target with a pharmaceutical composition in the circulatory system by adjusting a frequency of the rotating magnetic field, a plane of the rotating magnetic field with respect to the therapeutic target, and a distance of the rotating magnetic field with respect to the therapeutic target.

In various aspects, the therapeutic target can be a thrombosis in a human blood vessel. In another aspect, the magnetic rotors can be magnetic nanoparticles injected into the circulatory system. In particular, the therapeutic target is a full or partial blockage of a vein bivalve. In yet another aspect, the magnetic rotors traverse through the fluid in the circular motion by repeatedly (a) walking end over end along the blood vessel away from the magnetic field in response to the rotation of the rotors and an attractive force of the magnetic field, and (b) flowing back through the fluid towards the magnetic field in response to the rotation of the rotors and the attractive force of the magnetic field.

In various aspects, the rotor is a magnetic nanoparticle of a diameter from about 20 nm to about 60 nm. In another aspect, the therapeutic target is a vascular occlusion in the patient head or a vascular occlusion in the patient leg.

In yet another embodiment, a method is provided for increasing drug diffusion in a circulatory system comprising (a) administering a therapeutically effective amount of magnetic rotors to the circulatory system of a patient in need thereof, and (b) applying a magnet to the patient, the magnet having a magnetic field and a gradient for controlling the magnetic rotors in a circulatory system, and (c) using a controller for positioning and rotating the field and the gradient in a manner to agglomerate and traverse the magnetic rotors with respect to a therapeutic target in the circulatory system of the patient, wherein diffusion of a pharmaceutical composition in the circulatory system at the therapeutic target is increased.

In various aspects, the pharmaceutical composition can be attached to the magnetic rotor. In other aspects, the pharmaceutical composition can be administered to the circulatory system of the patient separate from the magnetic rotors. In various embodiments, the pharmaceutical composition is a thrombolytic drug.

In various aspects, therapeutic target can be a fluid obstruction such as atherosclerotic plaques, fibrous caps, fatty buildup, coronary occlusions, arterial stenosis, arterial restenosis, vein thrombi, arterial thrombi, cerebral thrombi, embolism, hemorrhage and very small vessel. In yet another aspect, the circulatory system is vasculature of a patient, particularly a human patient.

In yet another aspect, the magnet can be a permanent magnet coupled to a motor, and the controller can control a motor to position the magnet at an effective distance, an effective plane with respect to the therapeutic target, and rotates the magnet at an effective frequency. In another aspect, the magnet can be an electromagnet having a magnetic field strength and magnetic field polarization driven by electrical current, and the controller can position the electromagnet at an effective distance, an effective plane with respect to the therapeutic target, and rotates the magnetic field of the electro-magnet by adjusting the electrical current.

The system of the method can further include a display for viewing the magnetic rotors and therapeutic target, and a user interface for controlling the magnetic rotors, wherein a user controls the magnetic rotors to increase contact of the therapeutic target with a pharmaceutical composition in the circulatory system by adjusting a frequency of the rotating magnetic field, a plane of the rotating magnetic field with respect to the therapeutic target, and a distance of the rotating magnetic field with respect to the therapeutic target.

Additional Embodiments of the Magnetomotive Stator System

Figure 3:
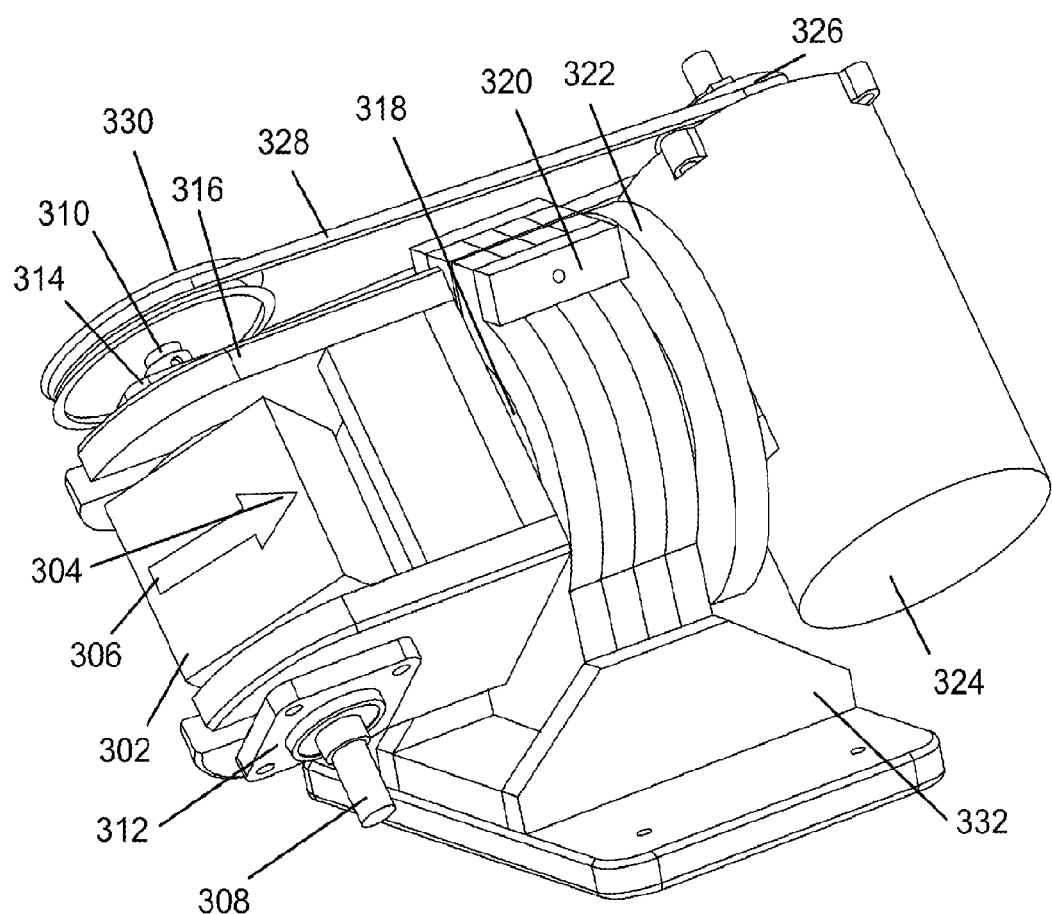
FIG. 3 shows an example of a permanent-magnet stator system whose magnet's North-South pole rotates in a plane perpendicular to the system's front face, which is driven by a single motor.

FIG. 3 depicts an embodiment in which the magnet is made to spin in a plane that is perpendicular to that shown in FIG. 1. Here the permanent magnet 302, which possesses a North magnet pole 304 and a South magnet pole 306, possesses two support flanges. The first magnet flange 308 passes through the first bearing 312 and the second magnet flange 310 passes through the second bearing 314. The bearings are supported by a magnet support structure 316. The magnet support structure is connected to a center shaft 318, which is supported by the support 320 for the center shaft. The center shaft 318 is attached to the motor mounting plate 322, to which is attached the drive motor 324. In this embodiment, the magnet drive motor sheave 326 is connected to the drive belt 328. The drive belt 328 is connected to the magnet sheave 330. The support for the center shaft 320 is attached to the magnet assembly support structure 332.

In this embodiment, the permanent magnet 302 is made to spin in the plane perpendicular to the front face so that the North magnet pole 304 and South magnet pole 306 rotate in the same plane. The drive motor 324 turns the motor sheave 326, which turns the drive belt 328. The drive belt 328 then turns the magnet sheave 330, which is attached to the second magnet flange 310. The first magnet flange 308 and second magnet flange 310 pass through the first bearing 312 and second bearing 314, respectively. Both magnet flanges 308 and 310 are attached to the permanent magnet 302, thus allowing the drive motor 324 to spin the permanent magnet 302.

Figure 4A:
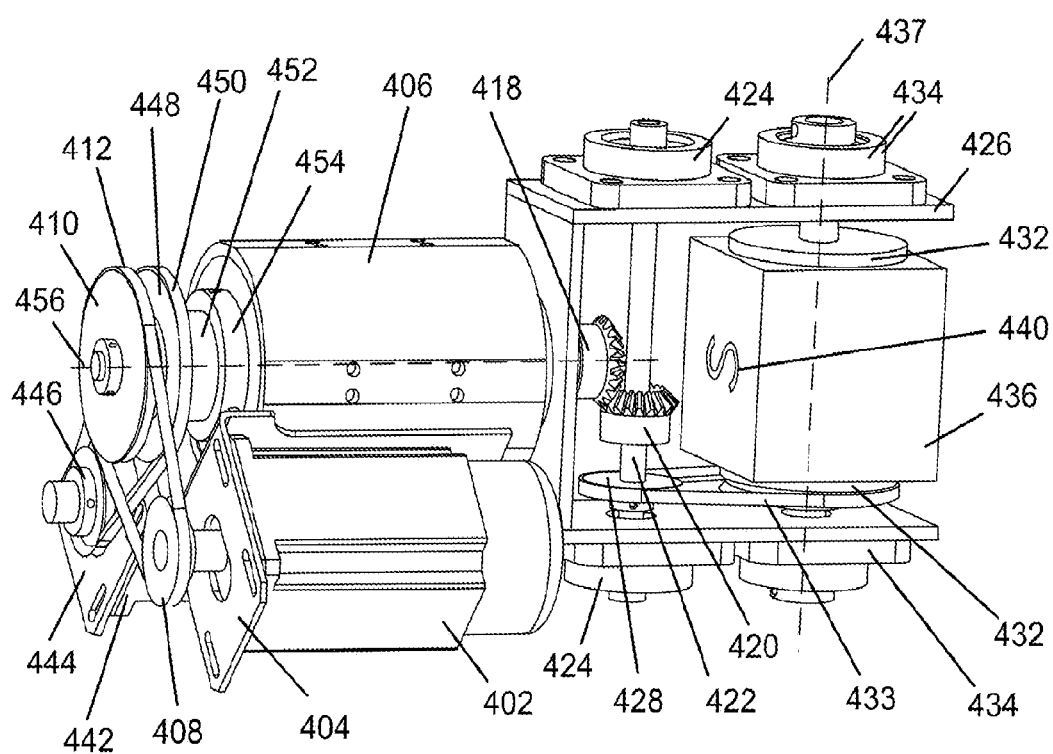
FIGS. 4A and 4B (cross-section of 4A) show an example of a permanent-magnet stator system driven by two motors, allowing the magnet to be rotated in any plane.
Figure 4B:
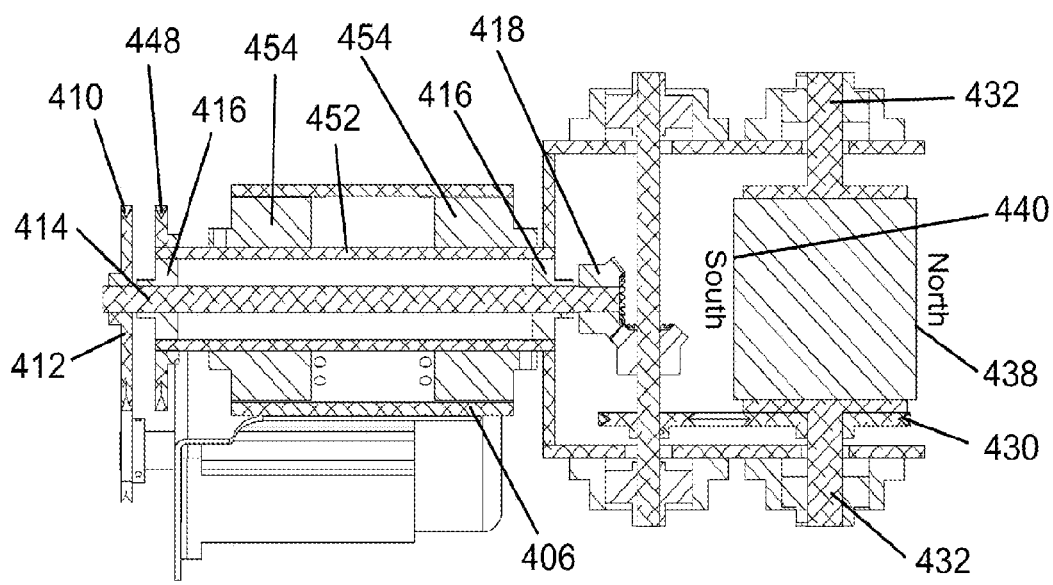

In FIG. 4, a permanent magnet 436 is depicted that is capable of being rotated in any plane using a two-motor system. The magnet possesses a North magnet pole 438 and a South magnet pole 440. The first motor 402 is attached to the central support 406 via the first motor flange 404. Attached to the first motor 402 is the first motor pulley 408. The first motor pulley 408 is connected to the first axle pulley 410 via the first motor belt 412. The first axle pulley 410 is attached to the first axle 414 which passes through the first axle bearings 416. At the end of the first axle 414 is the first miter gear 418. Said first miter gear 418 engages the second miter gear 420. The second miter gear 420 is attached to the second miter gear axle 422, which passes through the second miter gear bearings 424. The second miter gear bearings 424 are attached to the magnet support yoke 426. The second miter gear pulley 428 is connected to the second miter gear axle 422. Said second miter gear axle 422 is connected to the magnet pulley 430 by the magnet belt 433. The magnet pulley 430 is attached to one of the two magnet flanges 432. The magnet flanges 432 pass through the magnet bearings 434. A second motor 442, which is attached to the central support 406 by the second motor flange 444, which possesses a second motor pulley 446. Said second motor pulley 446 is connected to the second axle pulley 448 by the second motor belt 450. The second axle pulley 448 is connected to the second axle 452, which passes through the second axle bearings 454.

In this example, the first motor 402 turns the first motor pulley 410, which transmits the rotation to the first axle pulley 410 via the first motor belt 412. The first axle pulley 410 turns the first axle 414, which is made free to turn using the first axle bearings 416. Turning the first axle 414 results in the turn of the first miter gear 418, which is connected to the first axle 414. The first miter gear 418 transmits the rotation to the second miter gear 420, which turns the second miter gear axle 422. The turn of the second miter gear axle 422 is made possible using the second miter gear bearings 424. The turn of the second miter gear axle 422 results in a turn of the second miter gear pulley 428, which turns the magnet pulley 430 via the magnet belt 433. The magnet pulley 430 turns the magnet flanges 432, which results in a turn of the magnet 436 around a first axis 437.

The second motor 442 turns the second motor pulley 446, which turns the second axle pulley 448 via the second motor belt 450. The turns of the second axle pulley 448 results in a turn of the second axle 452, which is made free to rotate using the second axle bearings 454, thus allowing the magnet 436 to be rotated around a second axis 456.

Figure 5:
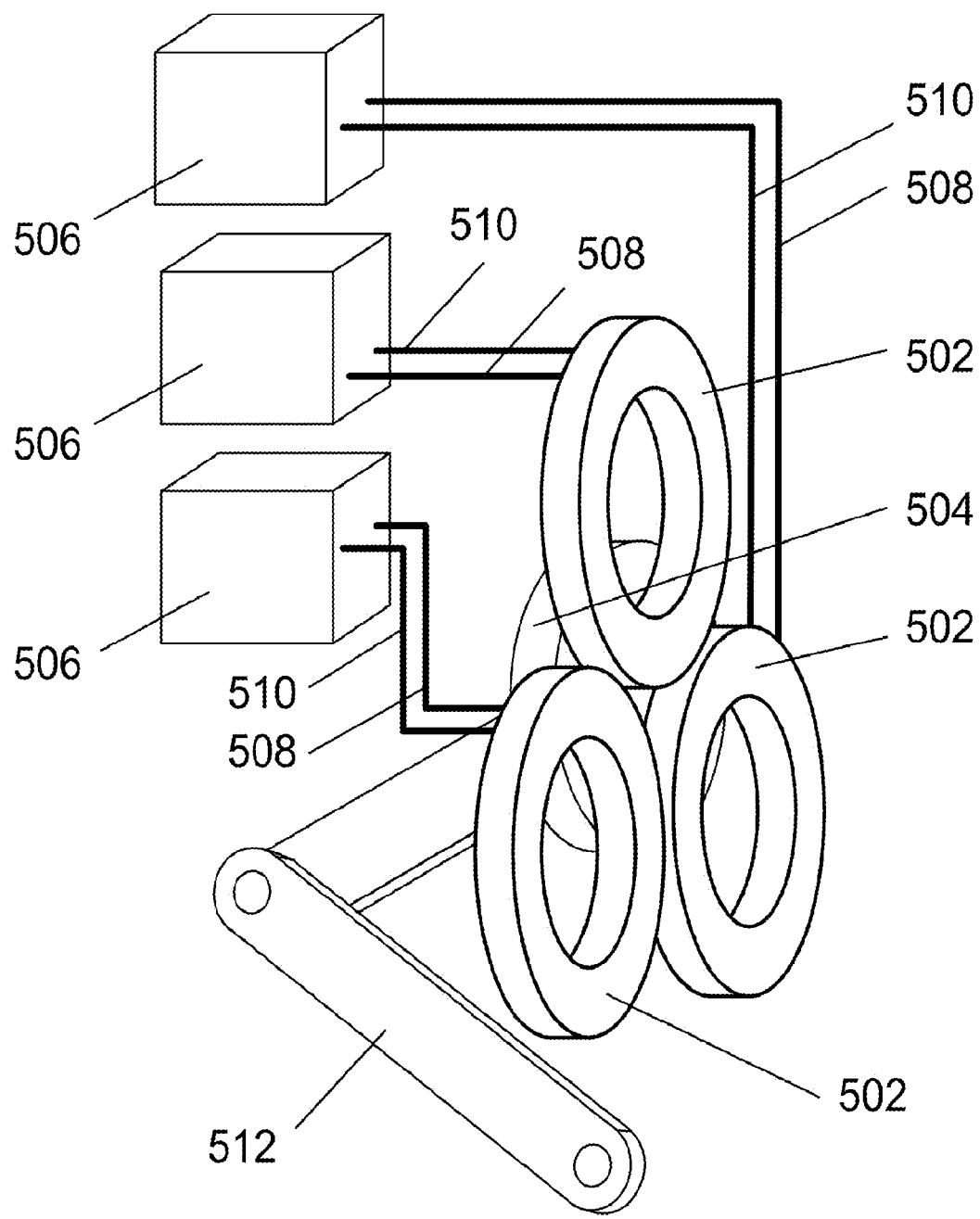
FIG. 5 shows an example of a three-electromagnet stator system, with power supplies, attached to an arm positioner.

FIG. 5 is an example of a magnetomotive system comprised of electromagnetic coils 502. The electromagnetic coils 502 are attached to a support structure 504. Each electromagnetic coil 502 is connected to a power supply 506 via a power supply cable 508 and power supply return cable 510. The support structure is connected to a two-segment arm positioner 512. In this example, each power supply 506 delivers power to its respective electromagnetic coil 502 via the power supply cable 508 and the power supply return cable 510. The two-segment arm positioner 512 allows the support structure 504 to be positioned in space.

Magnetomotive Stator System and Magnetic Tool Rotor

In yet another embodiment, a therapeutic system is provided for increasing fluid flow in a circulatory system comprising a magnet having a magnetic field for controlling a magnetic tool in the fluid, and a controller positioning and rotating the magnetic field with respect to the therapeutic target to rotate an abrasive surface of the magnetic tool and maneuver the rotating abrasive surface to contact and increase fluid flow through or around the therapeutic target. In various aspects, the circulatory system can be vasculature of a patient, particularly a human patient. In various aspects, the magnetic tool can be coupled to a stabilizing rod, and the magnetic tool rotates about the stabilizing rod in response to the rotating magnetic field. In yet another aspect, the magnetic tool can include an abrasive cap affixed to a magnet which engages and cuts through the therapeutic target. In another aspect, the controller positions the magnetic tool at a target point on the therapeutic target, and rotates the magnetic tool at a frequency sufficient to cut through the therapeutic target. The magnet can be positioned so that poles of the magnet periodically attract the opposing poles of the magnetic tool during rotation, the magnetic tool is pushed towards the therapeutic target by a stabilizing rod upon which the magnetic tool rotates. In another aspect, the magnet can be positioned so that the poles of the magnet continuously attract the opposing poles of the magnetic tool during rotation, and the magnetic tool is pulled towards the therapeutic target by an attractive force of the magnet.

FIG. 9 shows one use of the magnetomotive stator system to wirelessly manipulate a mechanical thrombectomy device (also referred to as a "magnetic tool" above). In this example, a vessel obstruction 830 inside a blood vessel 828 is unblocked by a rotating magnet 902 which possesses a North magnet pole 904 and a South magnet pole 906 in directions transverse to the axis 908. The magnet 902 follows the external magnetic field vector 812, which is generated wirelessly by the magnetomotive stator system. The external magnetic field vector 812 changes in time in the direction of the magnetic field rotation angle 810. The rotation of the magnet 902 is stabilized by passing a stabilizing rod 908 through a hole in the magnet 902. The magnet 902 is free to rotate about the stabilizing rod 908. An abrasive cap 910 is affixed to the magnet 902 which engages the vessel obstruction 830. This abrasive cap 910 may use a coating or surface treatment that ensures minimal damage to healthy tissue and maximal damage to the vessel obstruction 830.

One advantage of using the magnetic tool, when larger magnetic rotors are used, the use of the magnetic gradient, which may be time-varying, and a time-varying magnetic field allows for devices to be constructed which possess a magnet capable of rotating at the distal end. The result is that these devices can be made much smaller and cheaper than existing clinical devices used to amplify the effects of pharmaceuticals or to bore through obstructions in the vasculature. More importantly, commercial technologies that use a rotation mechanism within a vessel or chamber require a mechanical or electrical transmission system from the proximal end to the distal end, which can complicate the device, make the device more expensive, and increase the overall size. The present invention generates mechanical action wirelessly at the tip without the need for the mechanical or electrical transmission system, thereby allowing the device to be smaller, simpler, and cheaper to manufacture.

FIGS. 10A and 10B illustrate an example method of use of a magnetomotive stator system and magnetic nanoparticles for the treatment of a vascular occlusion in the brain 1004, in accordance with an embodiment of the invention. FIG. 10B shows a drip bag 1006 and an injection needle 1008 coupled to a conduit or tubing inserted at an injection location 1010 of an arm 1012 of a patient. FIG. 10A is a close-up schematic illustration of a portion of the vasculature of the brain 1004 including a blood vessel 828 where blood flow 1002 is unobstructed and a vessel branch having an obstruction 830. FIG. 10A also illustrates a rotating magnetic nanoparticle (e.g., FIG. 8B) near the obstruction 830.

For example, the system may be used in a clinical setting for the enhancement of tPA which is injected intravenously. Magnetic particles would be injected either before, after, or attached to a thrombolytic. The magnet system, which is placed close to the patient and near the clot, would be activated. However, the system would not need to be generating a changing magnetic field at this time in that the gradient would be sufficient to collect particles at the desired obstruction. When magnetic mixing is desired, the magnetic field would be made to alternate in time which, when combined with the magnetic gradient, which may or may not be varying in time, causes the action of the thrombolytic to be enhanced. Thus, the clot could be destroyed faster and better as compared to other approaches.

Magnetically-Enhanced Drug Diffusion

FIG. 11 shows how to magnetically enable control over the diffusion of a chemical injected into a moving fluidic system. In this model, fluid-A is travelling and permeates the system (white region in FIG. 11A). At a later time, fluid-B is injected (shaded region). FIG. 11B shows the problem. Fluid-B is limited in its ability to penetrate the "leg" because the velocity of the flow does not travel far into the leg. The system then must rely on diffusion to dilute fluid-A with fluid-B. This can take a very long time.

Figure 11A:
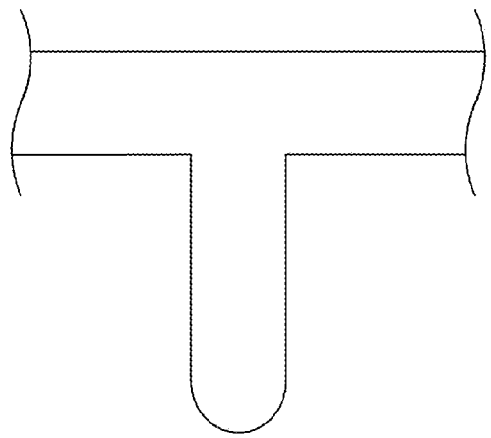
Figure 11B:
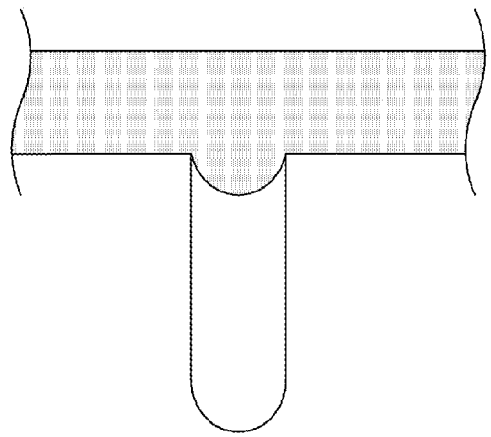
Figure 11C:
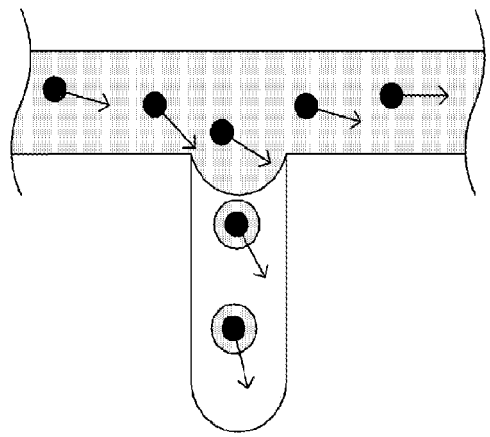
Figure 11D:
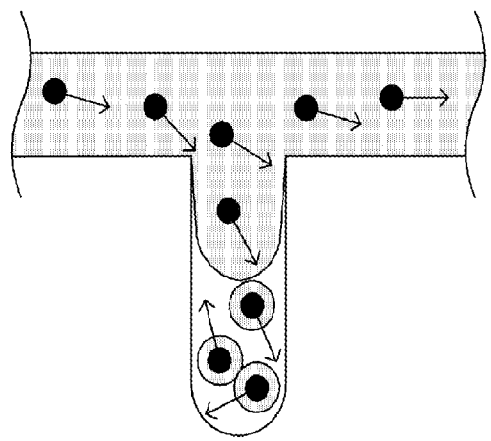
Figure 11E:
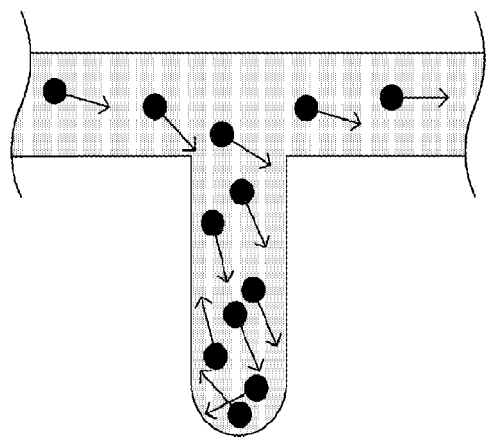

What has been observed is that when magnetic nanoparticles are placed into fluid-B, and a magnetic field and gradient are imposed to pull some of the nanoparticles out of the stream into the leg, which take a bit of fluid-B with them (FIG. 11C). Time-varying aspects can be changed to amplify the action. For example, the rate of field rotation, the strength of the magnetic gradient, the orientation of the source field, and the size and strength of the magnetic particle. In time, more particles collect at the bottom of the leg and begin to set up circulation patterns, which distribute fluid-B into fluid-A much faster than is possible via diffusion alone. The longer the process runs, the more particles are collected, and the stronger the mixing effect becomes, until fluid-A is essentially replaced with fluid-B.

In the case of clot destruction, the leg represents a blocked vein or artery. As the figure depicts, to contact a thrombolytic drug to the surface of the blockage, only the force of diffusion is involved if the obstruction is sufficiently far from the main flow. Therefore, thrombolytic drugs, and other pharmaceutical compositions effective in substantially clearing a fluid blockage from a circulatory system, are limited in their effectiveness; relying on diffusion in vivo could result in negative clinical outcomes. Because thrombolytic drugs, and pharmaceutical compositions effective in substantially clearing a fluid blockage from a circulatory system have a relatively short half-life, it is an advantage of the present magnetomotive stator system to speed the process. If the objective is to deliver a therapeutic concentration of fluid-B at the end of the leg which is a fraction of the concentration in the main flow, the present invention is able to obtain the same therapeutic concentration of fluid-B for a much smaller dose of fluid-B initially injected (See FIG. 30). This means the present invention provides enhanced therapeutic advantages allowing the use of a smaller dose of a pharmaceutical composition, some of which can cause bleeding or even death.

Another advantage of the present invention is, in the case of the magnetic tool, the system is capable of grinding away large volumes of thrombus or other blockage material, such as atherosclerotic plaque material, quickly and very precisely. It has been observed that a 2 french hole (⅔ mm) was cut through a mock atherosclerotic clot using the wireless magnetomotive stator system of the present invention. With respect to the use of magnetic nanoparticles in the present invention, the present system allows for precise control of magnetic particles to create a relatively "gentle" scouring action that allows the leaf valves in the veins to remain intact and undamaged. With respect to the magnetic tool, this action can be used in combination with thrombolytic drugs to remove clot material in an occluded artery or vein. When used with a thrombolytic in the blood clot, thrombolytic could be helpful when mechanical action is intended to be minimized. Using magnetic nanoparticles, the material removed from the blocked vein can be captured with a small magnet on a guide wire. Depending on the mode of operation, the removed material has been observed to be small (less than 1 mm size clot particles), or ball mixtures of clot material, drug and magnetic particles. Both the magnetic particle collection and magnetic tool objects are capable of being visualized with standard imaging technologies allowing for computer-reconstructed path planning.

FIG. 12 is a drawing of another embodiment of the magnetic field generator of this invention. In this figure, the generator 1200 is comprised of permanent magnet source 1205 with North 1206 and South 1207 poles, mounted so two separate rotations about axis 1210 and about axis 1215 are enabled. For spin about axis 1210, magnet source 1205 is rotated by pulley belt 1225, which is driven by geared shaft 1226, in turn driven by driving gear 1230. Gear 1230 is mounted on thrust bearing 1235 and driven by motor 1240 mounted on rotor system 1225, 1226, 1230 that enables rotation about the spin axis 1210 using a motor 1245. A separate drive system enables rotation about second axis 1215 using components 1220, thrust bearing 1235, and motor 1240. The generator is positioned with the jointed arm 1250. An advantage of preferred embodiment 1200 over second preferred embodiment 1300, shown schematically in FIG. 13, is the simplicity, smaller size, and lower cost. A disadvantage is the lack of some of the added features of control and complexity of the second preferred embodiment 1300.

FIG. 13 is a schematic drawing of yet another embodiment of the field and gradient generating device of this invention. Shown is a block diagram of a magnetic field generator 1300 of this invention. Three coils, 1301, 1302, and 1303, are fed currents from drivers 1311, 1312, and 1313, through connections 1321, 1322, and 1323, respectively. Drivers 1311, 1312, and 1313 are current sources each controlled separately by distributing circuit 1330, which receives information from computer 1335. Each current source, 1311, 1312, 1313, is capable of generating a sine wave current sufficient to provide the peak magnetic field required. In many cases this will be a peak field of less than 0.3 Tesla. If desired in individual cases, the currents may have more complex temporal variations than sine waves. As determined by computer 1335, in response to physician input 1341, the distribution and types of currents and their sequences to each of the coils will be calculated by the computer. The specific operational instructions from programs in computer 1335 are based on knowledge of the particular operation, with specific instructions thereby provided for operating according to the present procedure input by the physician. An advantage of the second preferred device 1300 of this advantage over first preferred device 1200, is the added flexibility in type of fields generated from the more complex magnetic field sources and the computer input, and the added refinement to the new procedures.

The design of the circuits, power supplies and controls of generator 1300 is composed of individual units to perform with these properties and specifications using methods that are well known to one skilled in the field of magnetic coil design, power supplies, and computers and logic circuitry.

Two major classes of blockage in the medical cases to be treated by methods of this invention are partial and total. Partial blockage yields, in general, low blood flow, while total blockage will result in no blood flow. In both cases the effectiveness of a drug delivered to remove the clot by conventional means will generally be difficult and inefficient. The delivery of the drug to the surface of a clot is in principle difficult and inefficient in spite of special methods to stir the drug-blood mixture near a clot. Major limits to present methods of removing the blockages include the difficulty of effective drug action on an occlusion, the incompleteness of removal of dislodged material, damage to vessels and adverse effects of downstream components of the removed material. FIGS. 14A and 14B exhibit the underlying physical reasons for the difficulty and inefficiency of conventional treatments of a blood clot, and for which the present invention provides major improvement.

FIG. 14A is a cross sectional view of a typical accumulation of occluding material in a bend of a section of a blood vessel 1400 having no flow, illustrating a common difficulty in using a drug for dissolving the material. Adjacent a vessel wall 1405 is a target region of deposited occluding material 1410, the "clot", with internal boundary edge 1415. Here the physician has introduced a drug 1425 in the vicinity of the clot. This exhibits the typical situation of a stagnant action layer 1430 of partially interacting material and layer 1435 of more concentrated but less effective drug. Layers 1430 and 1435 separate the clot from the more concentrated thrombolytic drug 1425 that had been injected into the vessel 1400 in that general region. Motion and distribution of the drug can arise only from thermal agitation and slow dispersion as a means of refreshing contact between the clot and the injected drug, which makes the action extremely slow and inefficient. Some practitioners have introduced metal stirrers, venturi flow-based jets, and sound-based agitation technologies to increase efficiency, but the difficulties and limitations of those methods have been documented.

FIG. 14B is a cross section view of a target occlusion 1455 formed against a wall 1460 of a vessel 1465 having a stiffened valve leaflet 1470, with low blood flow in a region 1480 and with very low fluid (mixed blood and drug) flow at the clot surface 1457. This results in little interaction on the clot of a drug 1475 injected upstream into the region 1480, without using excessive quantities of it. Traditional approaches, involve closing off the vessel and slowly injecting thrombolytic agent, with slow, inefficient dissolving of the clot, and the injection of large quantities of thrombolytic drug, thus exhibiting approximately the same difficulties of the case with a blocked vein. Some conventional treatments provide artificial mechanical, venturi flow-based, and sound-based agitation in region 1480 in attempts to enhance the efficiency of interaction at the clot surface 1485. Catheters with jets may spray thrombolytic drugs in attempts to get more efficient dissolution of the clot. Removal of the occluding material is sometimes performed by insertion of mechanical devices, with considerable difficulty and with danger to the valve. All of these methods may be helpful in some cases, but are generally of limited effectiveness.

FIG. 15A through 15C exhibit the underlying process of this invention in the development of rods from magnetic nanoparticles. They show a cross section of the sequence of structuring of coated or uncoated magnetic particles with increasing magnetic field. Increase of the field during a rising part of the cycle causes more and more particles to align into longer rods.

These are shown with zero field in FIG. 15A as nanoparticles in a random disposition of particles 1505, arrayed so as to be roughly evenly distributed in space, and having a certain statistical fluctuation in position. In FIG. 15B, when a small external magnetic field 1510 is applied to the same group of particles, they are formed into a loose array 1515 of short, oriented magnetic "rods". At a certain larger field 1520, depending on nanoparticle size and optional coating, shown in FIG. 15C, the same particles aligned as magnetic rods 1525 have become longer. In this figure, it is depicted that the rods are uniform in size although that is not strictly the case, nor is it necessary. This magnetic process can be viewed in two ways: a) the field increase from FIG. 15A to FIG. 15B being that in a single (slow) cycle of magnetic field alternation, or b) the increase over a number of cycles as the peak-to-peak magnitude of the field generated is increased. Depending on the absolute scale and oscillating frequency, the actions are not reversed during a given cycle of oscillation. In general, as used in the present invention, the method applies magnetic fields of approximately 0.02 to 0.2 Tesla, and the rods vary from 0.1 to 2 mm length, although other ranges may be useful.

At a certain rotating magnetic field strength and field rotation frequency, depending on nanoparticle size and optional coating, the rods will reach a saturation field and achieve a maximum length, developing as depicted in the graph of FIG. 16. The rod growth is not necessarily exact, and the curve illustrates a general nature of the growth. Each fully developed rod may contain a number of nanoparticles, as many as 10 or many more, depending on their size, and the magnitude of the rotating magnetic field. The rods are not stiff, depending on the magnetic field and gradient, and on the amount of magnetite in each particle as well as the nanoparticle size. Other materials may be attached to each particle for chemical, magnetic, and imaging reasons. That chemical can be a thrombolytic drug. The thrombolytic drug can also be injected independently.

Figure 17:
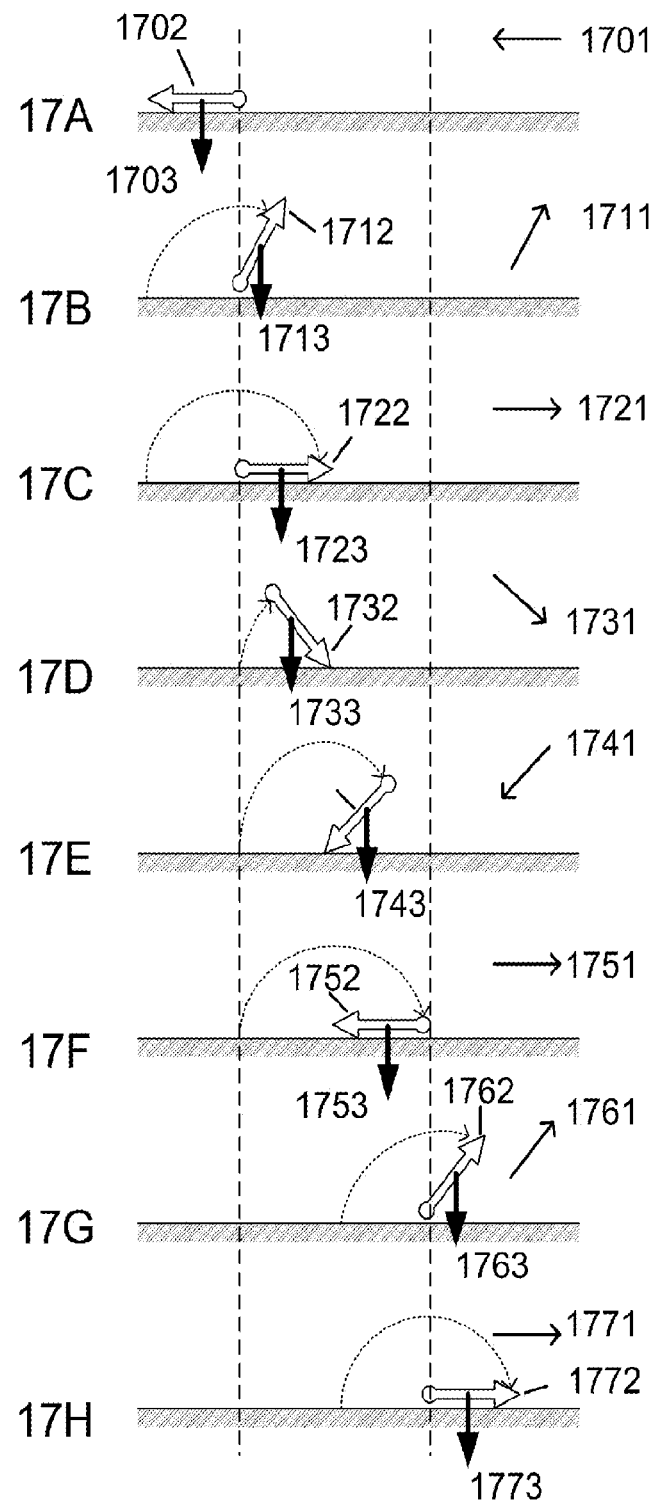

FIG. 17 exhibits the geometric features of the end-over-end walk of a single rotating rod acting from application of a rotating magnetic field emanating from a fixed source in space. It displays a sequence of 8 positions of a single rotating rod as it rotates and walks, so as to exhibit the directions of field and pulling force of the gradient. It is to be understood that the effective magnetic moments of individual particles are continually aligned with the local magnetic field, so that they maintain the interactions to retain the rod and its magnetic moment, while the field and rod are rotating, that is, maintaining alignment of the rod with the field.

Without being bound by a particular theory, and as will be discussed in the following section in equations [1] and [2], the field B establishes a torque, but it does not exert a pulling force on the rod moment, while the gradient G exerts a pulling force but no turning torque on the moment. Therefore, a rotating magnet source will have a pulling gradient towards it, shown as the downward arrows in all stages of FIG. 17. Smaller magnetic nanoparticles, generally below 150 nm diameter, act primarily as permeable materials, which will automatically align with the local field without the need to individually rotate in space. In any case, they will form the rods as described above, which themselves have moderate rigidity on the nano-scale, but are very soft in the millimeter scale of treatments of this invention. In FIG. 17, trigonometric labeling illustrates the geometrical (angular) aspects of changing components of the force and torques on the particles as related to the walk of the rod towards the right in response to the rotating field. In other words, the rods act approximately as fixed magnetic rods. In the figure, the field direction in each of the 8 positions, is shown by arrows 1701, 1711, 1721, etc. as the field rotates clockwise. The rod magnetic moments 1702, 1712, 1722, etc. follow that direction. In each stage shown, however, the arrows 1703, 1713, 1723, etc. point downward towards the center of the rotating field source, according to equation [2] below. On the scale of the rod lengths, about 2 mm, the movement to the right is small relative to the distance to the source magnet.

FIGS. 18A and 18B illustrate the development of a limit to the concentration of magnetic rods when the source magnetic field is rotating, about a fixed position of the source magnet. The gradient, unlike the field, will always pull towards the magnetic center of the source. The field B itself, only creates a torque τ of alignment on a tiny magnetic dipole moment μ

$$\tau = \mu B \sin \Phi, \quad [1]$$

where Φ is the angle between the direction of the moment μ and the field B. A uniform field without gradient will not create a force on the moment μ. However, a gradient G will create a force F on tiny moment μ according to $$F = \mu G \cos \Phi, \quad [2]$$

where Φ is the angle between the direction of the moment μ and of the gradient G.

FIG. 18A shows the nature of the spatial "resolution" of the system in an open location for the rods. For a fixed location of the rotating magnet source, the pull towards it from the gradient will change direction as the rods 1805, 1806 and 1807 have walked to the right. They will have increased distance, hence a loss of strength of the field. In FIG. 18A, as the rotating external field source will have remained at the left shown by arrow 1810, the rod locations have moved to the right of the fixed rotating magnet, (here below and off screen). At the stage shown here, the arrows depicting the three rods 1805, 1806, and 1807 have moved far to the right from the center of the rotating source magnet system. Relative to their size, and their distance to the magnet source, this distance to the right has increased so that the field source and gradient are at an angle and are reduced in magnitude. The gradient, in the direction shown by large arrow 1810, pulls on the particles and rods, which are driven by the traction provided according to the force of equation [2] at their locations. The gradient G is falling off with distance from the source, typically by a factor between the inverse cube and inverse fourth power of distance, while the field is falling off with distance from the source roughly as the inverse cube of distance from the source center. In this walking they are also losing attractive gradient, needed to pull them down onto a walking surface. They ultimately lose traction. The consequence of this, shown in plot FIG. 18B illustrates the distribution of particles that has occurred when the angle of the gradient is changed from left to right, as a result of the mechanism described in FIG. 18A below. This graph is for a fixed location of the magnet source, and is useful in describing the "resolution" of the walking rod system. In practice the source can be moved if desired for a long occlusion, depending on the medical strategy for treating it.

A consequence of the action described in FIG. 18A, is that for a fixed location of the rotating magnet source the force reduction with distance as the rods walk will result in a distribution of rod activity approximately as shown in FIG. 18B, where the arrow simply points to a region of maximum density at closest location to magnet, and represents the position dependence of the rod walking, which is of maximum strength when the rods are closest to the magnet source.

The magnetic mechanics of a single rotating rod provide the soft brush quantities of this invention according to the following calculations. It is to be understood that these conditions apply directly only for rod bundles that have relatively sparsely attached clot material. As discussed below, an extremely useful mode of operating rods in a rotating field in which the clot material is allowed to become bundled with the rods, leading to soft clumps that are stable and magnetically removable. Such a mode will not follow the calculations of this section. Nevertheless, the calculations of this section will show the underlying behavior of the rotating scouring rods when lightly loaded, and a mode that may be used in cases of small occlusion material, or cases where the delicacy of the procedure or size of vein may not allow clumps of material to be endured. Such cases may arise in some occlusions in the brain.

Here, for simplicity the rods are treated as rigid. FIG. 19A is a diagram exhibiting trigonometric detail of the creation of rotational force and energy on the rotating rods that in turn creates turbulence to enhance drug mixing and interaction with the surface of the clot. The elements of the action of the magnetic rotating field B are shown at a given moment on a single rod of magnetic moment μ in a plane defined by directions of the rod magnetic moment, and the direction of the field B at an instant when B is directed at an angle β from the x-axis. At this instant the (constant) moment μ is directed at an angle θ from the x-axis. Therefore, at this instant the magnitude of the torque r generated on the moment μ by the external source magnet is given by $$\tau = \mu B \sin(\beta-\theta), \quad [3]$$

FIG. 19B shows, in coordinates centered at the center of a symmetrical rod the angular force F(θ) exerted on the rod, which is assumed to be symmetrical. This is the practical situation when the rod size is small compared with the distance to the magnet source. The resulting force $$F_\theta = 2\mu(B/L)\sin(\beta-\theta) \quad [4]$$

is generated by the field B at the ends of a rod of length L.

A drag force might be approximated from standard mechanics with angular dependence $\dot\theta^2$, that is $$F_{drag} = -C\dot\theta^2 \quad [5]$$

where C is a proportional constant. Under that (standard) assumption, the final equation of motion for a symmetric rod is $$ml\ddot\theta/4 = 2\mu\beta/l[\sin(\beta-\theta)] - C\dot\theta^2 \quad [6]$$

Further, defining an angle α=β−θ and letting β=ωt, with ω an angular rotational frequency, then $\dot\alpha = \dot\beta - \dot\theta$ and therefore, $\ddot\alpha = -\ddot\theta$. Equation [3] becomes $$Ml\ddot\theta/4 = (2\mu B/l)\sin\alpha - C(\omega-\dot\alpha)^2 \quad [7]$$

For a constant lead angle α, this simplifies to $$\sin\alpha = cl\omega^2/2\mu B \quad [8]$$

A maximum frequency $\omega_o$ that preserves a constant lead angle α is $$\omega_o^2 = 2\mu B/cl, \quad [9]$$

where α=π/2, that is, 90 degrees.

At some angular frequency greater than $\omega_o$ the moment t cannot follow the field rotation and the system becomes destabilized. At much higher frequency, the motion essentially halts, since the field leads by less than π/2 and for the other half of the time greater than π/2. Thus the two torques cancel. From this reasoning the kinetic energy will show a frequency dependence such as shown in FIG. 19C. Specifically, the kinetic energy T is $$T = 2 \times (1/2)(m/2)(l/2)^2\dot\theta^2 \quad [10]$$

FIG. 19C is a graph expressing this dependence of kinetic energy of the rod on frequency of rotation in which the maximum energy $T_o = (ml^2/8)\omega_o^2$ where ω=$\dot\theta$. That is, the peak rotational kinetic energy available for a single rod depends on the rod mass, length, and is quadratic in the angular velocity up to the point where the rod cannot follow the field rotation.

With the above understanding of the formation and mechanical behavior of a rod of magnetic nanoparticles, the use of the system and methods of this invention as it applies most simply to medical applications can be shown. The system of nanoparticles has been found to behave (and appear visually) as a group of flexible magnetic rods acting on occlusions in blood vessels. First, the treatment of the two characteristic problematic cases discussed with FIGS. 14A and 14B, above, will be shown with the introduction of rotating rods.

FIG. 20A illustrates the practical benefit of the introduction of turbulence with spinning rods of the present invention. A portion of a vessel having complete spatial blockage, shows the treatment by the methods of this invention of the problem shown with FIG. 14A, where it was treated conventionally. FIG. 20A is a cross section view of lumen 2000 with no flow, having a clot 2005, with a fresh supply of thrombolytic drug 2010 being injected near the occlusion. Three spinning magnetic rods 2030 (not to scale) have been shown injected along with the fresh drug 2010, and they generate local turbulence as they are pulled in the direction 2025 of a rotating magnet source (not shown here). With a clockwise spinning rotation, the rods are shown co-mingling with the fresh drug, and brushing the surface of the clot 2005 as they move slowly to the left as the external rotating magnetic field source moves. The tiny particles of clot 2005 accumulate at the right 2035, where they will form a ball, when the rotation is continued, as shown in FIG. 21A. The situation is to be compared with that of FIG. 14A, in a static application of drug that would have little mixing action, and must depend on lengthy time for removal of the clot.

FIG. 20B is a cross section view of the upper part of a lumen 2050 in which the methods and device of the present invention are shown solving the problem of inefficient clot removal by standard methods in the case as shown in FIG. 14B. This case might represent partial blockage in a leg artery. Here there is slowly flowing blood 2090 in the partially blocked lumen 2050, as was exhibited in FIG. 14B. Clot material 2058 and 2062 has built up around valve leaflet 2060, stiffening it and causing the significant but not total flow reduction. In this case the vessel 2050 is not totally closed, and the reduced flow is due to the partial occlusion and rigidity of rigid valve 2060. As described in FIG. 14B the blood flow, though slow, carries off injected drug with inefficient contact with the occluding material. In the method of the present invention the actions of rotating scouring rods 2055 are shown acting on clots 2058 and 2062, to greatly increase the drug contact, as well as provide gentle scuffing on a tiny scale. Turbulent flow in regions 2080 and 2085 is generated by the rotating rods 2055 whose tiny, somewhat flexible structure can work in such regions without damaging the vessel wall 2070 or valve leaf 2060. In some cases the removed magnetically infused material will be collected downstream by magnetic means.

When the rotation is continued under certain conditions (especially low flow) the clot material and magnetic nanoparticles can form a magnetic ball, as described in FIG. 21B below. Again, without being bound by a particular theory, it is believed that as the magnetic particles circulate they engage the surface of the thrombus. As the thrombus breaks into tiny pieces, the magnetic particles become encapsulated in a ball-like structure that is composed of the magnetite and thrombus materials. This structure has several advantageous properties.

1. The object accelerates the destruction of the thrombus by increasing the surface area of interaction and by causing more efficient circulation of the thrombolytic drug.

2. The structure captures smaller emboli, encasing them in the ball structure, thereby preventing them from escaping.

3. The structure will continue to break down slowly as that structure is lysed by the thrombolytic drug.

4. Alternatively, the structure can be recollected with a magnet-tipped device, thereby capturing the larger emboli and the magnetic particles.

With appropriate rate of delivery of drug, depending on the nature and age of a clot and of magnetic rod interaction, the magnetic rod scouring process can be arranged to mix clot material and rods, as described, to provide small, roughly spherical balls of clot material, combined with the magnetic rods. Essentially those conditions are determined by the rate of application and concentration of the thrombolytic drugs during the magnetic procedure. Physicians trained in the treatment of occlusions will use judgment of the rate of delivery of drug in order to form the ball of optimal properties (stiffness and size) for completion of the removal.

An application of this technique is described as follows. FIG. 21A is a cross section view of a blood vessel 2120, totally occluded by clot 2130, with no blood flow. Here magnetic rods 2122 are stirring the region just proximal to occlusion 2130 with clockwise rotation of the magnetic field, causing circulation pattern 2135. The mixing region 2125 contains a mixture of clot material, thrombolytic drug, and a small amount of magnetic rod material.

In the cross section view of FIG. 21B, this rotational interaction in blood vessel 2120 has continued and a ball 2140 begins to form of material stripped from thrombus 2130 using captured emboli, and a small amount of magnetic rod material.

In FIG. 21C the rotating ball 2140 has become enlarged and accelerates the therapy. It has opened the blocked channel in vessel 2120, leaving minor remains 2150 of occlusion material. The ball 2140 is still rotating and held in location by the force from the gradient of the rotating magnetic source (not shown).

FIG. 21D shows the means of capture and removal of completed clot ball 2140. At an appropriate time, before restored blood flow has pushed the thrombus ball 2140 downstream, a magnet-tipped probe 2145 is inserted and captures the ball structure 1040 for removal by retracting the magnet probe 2145.

FIG. 22 is a cross section view of a blood vessel 2255 containing valve leaflets 2260, one of which, 2262, has occluding material 2263 that has stiffened valve 2262 to become non-functional. Blood is flowing slowly in the direction of arrow 2270. An external magnetic field generator, (not shown here but such as shown in FIG. 12 or FIG. 13), has generated a rotating field in this region into which rotating nanoparticle rods 2275 are acting on clot deposits 2263 in the manner shown, for example, in FIG. 20B above. The magnetic rods 2275 shown may actually be members of a large number of such rods in the space adjacent the clots 2263. The rods are flexible and can be brushed to lengths shorter than the approximately one to two millimeters as described above, in order to function on the narrow corners of 2263. In laboratory tests the rods 2275 have functioned to remove material in model spaces such as 2263 that were approximately 2 centimeters wide and 3 millimeters deep and removed approximately 100 cubic millimeters of thrombus material.

FIG. 23 is a cross section drawing of a small blood vessel 2300 branching off a larger vessel 2305. The small vessel may be tortuous as shown, but does not hinder the walking travel such as that of a magnetic rod 2310 shown approaching clot 2315, which might be a clot in a brain or otherwise. Such small clots 2315 can be scrubbed as described for other, generally larger vessels such as 2255 in FIG. 22 above. The scrubbing can be generated to remove very small pieces of occluding material with the appropriate field and gradient choices. These particles may be up to a few microns in size, and will not cause further downstream damage. An advantage of this method of clearing a clot such as 2315 is that the occlusion might be total and difficult to reach by conventional existing methods, but the external rotating field will walk the rods to the occlusion point. The thrombolytic drug may then be introduced conventionally, if possible, at the site of the clot. At that point the stirring activity of the rods 2310 will make the drug act much faster than a static delivery.

Although magnetic particles are sufficient to gently clear delicate structures, it may sometimes be necessary to rapidly remove material quickly, as is the case for ischemic stroke in which parts of the brain are starved of blood. The same principles used with magnetic particles may be employed with larger magnetic structures which are specifically designed to rapidly remove the occlusion by mechanical abrasion while simultaneously increasing the flow of thrombolytic drugs to the blockage. These larger magnetic structures, termed here as thrombectomy devices, may be spheres with an abrasive material bonded on the surface. They can be sub-millimeter in size up to a millimeter or more, always with the consideration that removal after the particular procedure is necessary. This technique will likely result in smaller residual emboli than is typically seen with conventional techniques. A further advantage of this method over existing procedures is the controllable magnetic character of the removed material. The thrombectomy device, which is depicted as a sphere with a magnetic moment in this invention (i.e., a "magnetic ball"), may be tethered to simplify retrieval of the device. Alternatively, the device can be recovered in a manner similar to that proposed for the magnetic particles, namely, the use of a magnetically-tipped guide wire. The ball's surface may be comprised of any one or a combination of the following:

1. Contrast agent or agents which allow visualization with magnetic resonance imaging, X-ray, PET, or ultrasound technologies.
2. Drugs which accelerate destruction of the blockage.
3. Optimized surface geometries to accelerate grinding.
4. Abrasive surfaces to accelerate grinding.

FIG. 24A illustrates elements of the basic operation of the magnetically-enabled thrombectomy device which is presented as a sphere 2430 in this invention. The ball 2430 possesses a permanent magnetic moment with South 2410 and North 2420 ends. An externally applied magnetic field 2450 which advances in the counter-clockwise direction 2440 causes the ball to rotate. If the magnetic gradient is absent, as is the case in this FIG. 24A, no traction is generated against the surface 2460 and the ball does not translate.

FIG. 24B depicts the same case as 13A except that a magnetic gradient 2480 is present in an essentially fixed given direction 2480 which generates a force in the direction of 2480 acting on the magnetic ball 2430 to press it against the vessel wall. As a result, traction is created and translational motion occurs in direction 2470 with the counter clockwise rotation 2440 of the field.

An application of this technique is described as follows. FIG. 25A is a cross section view of a blood vessel 2510, totally occluded, with no blood flow. Here a magnetic ball 2530 is stirring the region just proximal to occlusion 2515 while mechanically grinding the occlusion's surface 2522. Contact against surface 2522 is created by a gradient in direction 2520 which results in a translational force in direction 2520. Clockwise motion of ball 2530 causes circulation pattern 2525 which accelerates action of the thrombolytic drug.

In the cross section view of FIG. 25B the rotational interaction in blood vessel 2510 has continued and ball 2530 has deeper penetration into occlusion 2515 in the translation direction 2520.

In FIG. 25C the rotating magnetically-enabled ball 2530 has opened the blocked channel 2535 in vessel 2510 leaving minor remains of occlusion material 2515.

FIG. 25D shows a means of capture and removal of the magnetically-enabled ball 2530 from the vessel 2510. The external field 2520 is no longer rotated or is removed which causes the ball to no longer translate to the right. At an appropriate time, before restored blood flow has pushed thrombectomy ball 2530 downstream, a magnet-tipped probe 2540 is inserted and captures ball 2530 for removal by retracting magnet probe 2540.

Cross sectional view FIG. 26A shows a tethered 2630 magnetically-enabled ball 2610 in vessel 2605. The tether 2630 allows the ball 2610 to rotate with the magnetic field, using attachments to be shown in FIG. 26B or 26C. In this figure, the North 2640 and South 2645 ends of the magnet are depicted at the ends of the black arrow. A free rotation of the magnet field 2640-2645 allows grinding of the thrombus or plaque material 2620 inside of the vessel 2605. The tether 2630 ensures the magnet 2610 can be manually retrieved without the need of the magnetically-tipped wire 2540 that was depicted in FIG. 25D. Tether 2630 will not wind on the ball 2610 under rotation when designed according to methods and devices of FIGS. 26B and 26C.

FIG. 26B shows a first embodiment of a tether 2660 which allows rotation around the magnet 2610 axis 2650. In this depiction, the tether end 2665 is inserted through the rotational axis 2650 loosely to ensure free rotation about the axis 2650. North 2640 and South 2645 arrow depicts magnetization direction of ball 2610.

FIG. 26C shows a second embodiment of a tether. Tether 2670 allows rotation around the magnet 2610 axis 2650 (perpendicular to loop 2675). In this depiction, the tether is loop 2675 which loosely surrounds the magnet's axis 2650 to ensure free rotation about the axis 2650. The North 2640 and South 2645 ends of arrow 2680 depict magnetization direction of ball 2610.

The technologies described in this invention also may be used in removing vulnerable plaque 2715 on a vessel 2705 wall depicted in FIG. 27. In FIG. 27, a cross section view of a blood vessel 2705 is shown with vulnerable plaque 2715 on the top and bottom of the vessel 2705. A rotating magnetic ball 2710 is shown grinding the plaque 2715 in a manner similar to that used on the occlusion 2515 depicted in FIG. 25C and the tethered depiction 2630 in FIG. 26A. This is made possible by using an externally-generated gradient 2720 to direct the action upwards towards the plaque 2715. It is assumed that thrombolytic drugs may also be present to ensure the ejected material is dissolved.

To ensure the magnetic particles and magnetically-enabled thrombectomy device are capable of being seen with modern imaging technologies, the particles must possess a coating which makes them opaque to that imaging technology. Example contrast coatings include x-ray, PET, MR and ultrasound. An advantage of such coatings is the ability to reconstruct a vessel which would normally be invisible due to the lack of blood flow in that region. Likewise, the ability to control and recollect the particles results in less toxic side effects as is seen with traditional contrast agents. For example, X-ray contrast agents typically require multiple injections because they are swept away with blood flow and are not able to travel in high concentrations down low-flow vessels.

FIG. 28A is a cross section drawing of a small blood vessel 2820 branching off a larger vessel 2810. The small vessel 2820 may be tortuous as shown, but does not hinder the walking travel of magnetic rod collection and the rolling motion of a magnetically-enabled ball. Both technologies are depicted as starting at the right side of the small vessel 2820 and approaching a blockage 2815. At subsequent points in time, the location of the magnetic ball or magnet rod collection 2825 is identified at the points indicated by 2826, 2827, 2828, and 2829. The translation direction of the particle collection or magnetic ball 2825 is indicated by the arrow 2830 extending from the body.

FIG. 28B is the same cross section drawing depicted in FIG. 28A. In this view, the imaged locations of the particle collection or the magnetic ball are connected allowing a computer to reconstruct the path 2835. This path can be referenced against preoperative images to confirm the anatomy and to plan procedures requiring navigation along the path.

Compositions for Use in the System

Various formulations of magnetic nanoparticles, whether formulated in combination with pharmaceutical compositions or not, may be used for administration to a patient. Those of skill in the art will recognize how to formulate various pharmaceutical compositions, drugs and compounds for co-administration with the magnetic nanoparticles hereof, or administration separate from the nanoparticles. Those of skill in the art will also recognize how to formulate coated nanoparticles in addition to uncoated nanoparticles that may depend on the coating and the therapeutic target to be treated. In some embodiments, various formulations of the magnetic nanoparticles thereof may be administered neat. In other embodiments, various formulations and a pharmaceutically acceptable carrier can be administered, and may be in various formulations. Pharmaceutically acceptable carriers are known in the art. For example, a carrier can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing (2000).

In some embodiments, the magnetic nanoparticles are formulated for administration by injection (e.g., intraperitoneally, intravenously, subcutaneously, intramuscularly, etc.), although other forms of administration (e.g., oral, mucosal, etc.) can be also used depending on the circulatory system blockage to be treated. Accordingly, the formulations can be combined with pharmaceutically acceptable vehicles such as saline, Ringer's solution, dextrose solution, and the like. The particular dosage regimen, i.e., dose, timing and repetition, will depend on the particular individual, that individual's medical history, and the circulatory system blockage to be treated. Generally, any of the following doses may be used: a dose of about 1 mg/kg body weight; at least about 750 µg/kg body weight; at least about 500 µg/kg body weight; at least about 250 µg/kg body weight; at least about 100 µg/kg body weight; at least about 50 µg/kg body weight; at least about 10 µg/kg body weight; at least about 1 µg/kg body weight, or less, is administered. Empirical considerations, such as the half-life of a thrombolytic drug, generally will contribute to determination of the dosage.

Advantages of the Magnetomotive Stator System

Having described the magnetomotive stator system and methods of controlling magnetic nanoparticles and other magnetic rods (e.g., magnetic tools), several advantages can be observed when compared to devices and pharmaceutical compositions currently on the market. First, the ability to combine the magnetic gradient with the magnetic field in an advantageous way that allows for magnetic rotors to be controlled from a distance, as opposed to catheters and cannulae which may cause unintended injury to a patient. Second, The ability to construct a compact mechanism that allows for the magnetic field to be changed in time in a simple and precise way, as well as possibly optimized so that control over the wireless rotors, is a significant enhancement in view of pharmaceutical compositions that are hard to precisely control in vivo at normal dosages.

In addition, when the magnetic rotors consist of magnetic nanoparticles, such as magnetite, the rotors can be manipulated in a way that results in better mixing of a chemical or pharmaceutical agent that is in the vicinity of the magnetic particles. The use of the magnetic gradient combined with a time-varying magnetic field allows for flow patterns to be created which then amplifies the interaction of the chemical or pharmaceutical. This mechanism has been observed in animal models for the destruction of clots within the endovascular system using tPA as a thrombolytic. The pharmaceutical compositions can also be attached to the magnetic nanoparticles to perform the same function. As a result, less of those agents would be required for patient treatment provided that the particles are able to be navigated to and interact with the desired targets using the magnetic gradient and the time-varying magnetic field of the system of the present invention.

The magnetomotive system can make use of an easy-to-understand user-interface which allows the user to control the rotation plane of the magnetic field in a way that is not presently found.

The magnetomotive system can also be used to move particles within small channels in a manner superior to approaches attempted with non-varying magnetic fields. The combined use of the magnetic gradient with a time-varying magnetic field allows for the particles to travel into small vessels, at which point therapy can be directed.

The invention will be further described in the following examples, which do not limit the scope of the invention described in the claims.

EXAMPLES

Aspects of the present teachings may be further understood in light of the following examples, which should not be construed as limiting the scope of the present teachings in any way.

Example 1—Administration of Magnetic Particles to Rabbits

Anesthetized rabbits were used to create an endovascular obstruction model by using the jugular veins and generating a clot at this location using thrombin, a natural product that produces blood clots. Once a stable clot was established, tPA (an enzyme commonly used to dissolve clots in endovascular obstruction patients), and magnetic nanoparticles were directed to the clot location and time needed to dissolve the clot was recorded. See FIG. 30. After varying time points, the animals were euthanized, the remaining clots were weighed and analyzed and tissues were collected to ensure that there was no damage to the vessel itself.

The endovascular obstruction model allows the determination whether the magnetomotive stator system can re-open a vein or artery faster than with tPA alone, and if the dosage of tPA can be reduced the amount of tPA required without causing damage to the vein. The data gathered from the present endovascular obstruction studies clearly show that the magnetomotive stator system significantly speeds up the "clot-busting" activity of tPA.

Detailed Protocol

Summary: Deep Vein Thrombosis is a common and potentially deadly condition, and current treatment options can do more harm than good in some cases. Our aim is to use a non-survival anesthetized rabbit model of venous thrombosis to determine whether we can substantially increase the efficiency of current pharmacological treatment by manipulating commonly used MRI contrast media magnetically (Magnetic particles in imaging: D. Pouliquen et. al., Iron Oxide Nanoparticles for use as an MRI contrast agent: Pharmacokinetics and metabolism; Magnetic Resonance Imaging Vol. 9, pp 275-283, 1991).

Magnetics: The iron nanoparticles described above are currently used in humans and considered safe.

Introduction: Deep Vein thrombosis (DVT) can be asymptomatic, but in most cases the affected areas are painful, swollen, red and engorged superficial veins. Left untreated, complications can include tissue necrosis and loss of function in the affected limb. The most serious complication is that the clot could dislodge and travel to the lungs resulting in a pulmonary embolism (PE) and death. Current treatment of DVT includes high doses of lytic enzymes such as streptokinase and tissue plasminogen activator (tPA), sometimes augmented with mechanical extraction (Angiojet, Trellis Infusion System). The doses of lytic enzymes are such that in many patients (particularly elderly) the risk of hemorrhage is high and poor outcomes common (A review of antithrombotics: Leadley R J Jr, Chi L, Rebello S S, Gagnon A. J Pharmacol Toxicol Methods, Contribution of in vivo models of thrombosis to the discovery and development of novel antithrombotic agents, 2000 Mar.-Apr., (2): 101-16; A review of potential tPA complications: Hemorrhagic complications associated with the use of intravenous tissue plasminogen activator in treatment of acute myocardial infarction, The American Journal of Medicine, Volume 85, Issue 3, Pages 353-359 R. Califf, E. Topol, B. George, J. Boswick, C. Abbottsmith, K. Sigmon, R. Candela, R. Masek, D. Kereiakes, W. O'Neill, et al.). The aim of the present DVT model is to allow determination of whether the magnetomotive stator system enhances the activity of tPA at the site of the thrombus such that a significantly lower dose of tPA can be used, greatly reducing the risk of hemorrhage. Further, current mechanical thrombolytics are known to damage endothelium. Following each experiment, the vessel segment is evaluated histologically for endothelial integrity.

Procedure: This is a non-survival procedure. New Zealand White rabbits (1.5-2.5 kg) are anesthetized using Ketamine 35 mg/kg, Xylazine 5 mg/kg IM and the ventral neck shaved and prepared for surgery. Mask induction using isoflurane gas may be used to deepen the anesthetic plane to allow for orotracheal intubation. Once intubated, the animal is moved to the operating room and administered isoflurane gas anesthesia (1-5%, to surgical effect) for the duration of the procedure. Heart rate, respiratory rate, body temperature and end-tidal $CO_2$ are monitored while the animal is under anesthesia. In an effort to reduce the number of animals and reduce the variability among studies, bilateral 10-12 cm incisions are made paramedian to the trachea and sharp/blunt dissection is used to isolate the jugular veins. If no significant complications arise, the total number of animals are reduced accordingly.

An ultrasonic flow probe is placed on the distal portion of the isolated vessel and baseline blood flow data is collected for 30 minutes. Following stabilization of venous flow, silk (or other braided, uncoated) suture (5 or 6-0, taper needle) is passed transversely through the center of the vessel lumen at the distal aspect of the area to be occluded, and secured with a loose knot (see reference #5). The function of this suture is to act as an anchor for the clot and prevent embolism. Then, a ligature is placed on the proximal and distal portion of the vessel (proximal in relation to the flow probe) to occlude flow. Ultimately a 2 or 3 cm segment of the vessel is isolated with ligatures. 100-200 U bovine thrombin is administered intravenously (27-30 g needle) into the space approximately 1 mm proximal the first ligature. The proximal ligature is placed immediately following withdrawal of the thrombin needle. The entry site of the needle is closed with a small drop of Vetbond® to prevent bleeding during the lysis procedure. The clot is allowed to mature and stabilize for 30 minutes at which time the ligatures are removed and tPA or a combination of tPA with magnetic nanoparticles (described above) are injected at the antegrade aspect of the vein (27-30 g needle, entry hole again sealed with Vetbond®). A dynamic magnetic field is applied to the location and dissolution of the clot is monitored continuously for up to 3 hours via ultrasonic flowmetry. Following re-establishment of flow the animals are euthanized while still under anesthesia with an i.v. overdose of pentobarbital (150 mpk). The experimental vessel segment and residual clot is then collected, weighed and fixed for further analysis. Dosages of tPA used in the endovascular obstruction model range from about 312.5 U to about 5000 U.

Groups: The study is accomplished in 2 phases, Pilot and Proof of Concept. Both phases include the procedures outlined here, but the Pilot Phase utilize only the left jugular, leaving the other a naïve histological comparator.

Pilot Groups

1. Thrombin only, no tPA. This group will establish the baseline mass of our thrombus and allow assessment of thrombus stability.

n=30.

2. tPA only, dose ranging to establish a fully efficacious dose (100% re-cannulation) n=6×3 doses=18

3. tPA only, dose ranging to establish a sub-optimal dose (either 100% effective in 25-50% of subjects, or re-cannulation in all subjects but only 25-50% of flow rate). tPA is notoriously variable, so the sub-optimal dose may be difficult to find. n=3×4 doses=12

Device alone to establish optimum particle concentration n=3×3 concentrations=9

Proof of Concept Groups:

Note: "n" numbers may be combined with pilot data depending on initial data quality, further reducing animal requirements.

1. Optimal tPA. n=6
2. Sub-optimal tPA. n=6
3. Device alone. n=6
4. Device+Optimal tPA. n=6
5. Device+sub-optimal tPA. n=6

Two questions can be answered using the present endovascular obstruction model:

Small Vessels: Following the completion of the thrombosis procedure in the jugular veins, the surgical plane of anesthesia is continued and a laparotomy performed. A portion of the bowel is exteriorized and bathed in saline to prevent drying. One of the large veins in the mesentery is tied off and cannulated with PE10. A mixture of iron particles and fluorescein (12.5 mg/ml in 100 ul) is injected and photographed under black light. This allows the determination of whether the fluorescein diffuses into the very small veins surrounding the bowel, and illustrates that the magnetomotive stator system directs magnetic nanoparticles to the small vasculature.

Safety: Is damage done to the endothelial lining using the magnetomotive stator system? Does it create hemolysis? The present endovascular obstruction model allows a determination via review of the vena cava. Following the completion of the thrombosis procedure in the jugular veins, the surgical plane of anesthesia is continued and a laparotomy performed. A 5-6 cm segment of the vena cava is isolated and all branches tied off. The vessel is tied off and cannulated with PE10. Either iron nanoparticles (12.5 mg/ml in 100 µl) or saline (100 µl) is injected and the vessel and is magnetically controlled for 3 hours. At the end of 3 hours the blood is removed from the vessel segment via venipuncture and sent for assessment of hemolysis. Following euthanasia the vessel segment is explanted for histological evaluation of the endothelium. Three experiments are performed with particles and three without.

Arterial Access

Using the DVT model described above, it has been demonstrated that the magnetomotive stator system significantly enhances tPA efficacy in this rabbit model. See FIGS. 29 and 30. Tissues have been gathered that were evaluated histologically. There is no damage observed to tissue when examined histologically.

OTHER EMBODIMENTS

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

REFERENCES CITED

Citation of a reference herein shall not be construed as an admission that such is prior art to the present invention.

What is claimed is:

1. A method of facilitating treatment of a total occlusion in a vessel of a subject through external magnetomotive manipulation of magnetic particles, the method comprising:
introducing a plurality of magnetic particles within vasculature of the subject,
orienting a permanent magnet external to the vessel to establish a magnetic rotation plane of the permanent magnet, wherein the permanent magnet has a magnetic field and a directed magnetic gradient;
programming a controller to rotate the permanent magnet in a manner sufficient to agglomerate the magnetic particles to form a plurality of magnetic rods within the vasculature to travel toward the total occlusion in the vessel in an end over end walking motion, wherein the end over end walking motion of each of the magnetic rods generates a stirring motion within the vessel proximal to the total occlusion, and wherein the stirring motion facilitates contact of at least one of (i) an agent configured to facilitate visualization with an imaging modality or (ii) a drug configured to accelerate destruction of the total occlusion, by enhancing diffusion of the agent or the drug to a region of the total occlusion.

2. The method of claim 1:
wherein the permanent magnet is rotatably coupled to a motor by a movable arm,
wherein the permanent magnet is configured to rotate about two different axes of rotation, and
wherein the particles comprises magnetite.

3. The method of claim 1, wherein the agent or the drug is attached to the magnetic particles prior to introducing the magnetic particles.

4. The method of claim 1, wherein the agent or the drug is introduced within the vasculature separate from the magnetic particles.

5. The method of claim 1, wherein the permanent magnet is rotatably coupled to a motor by a movable arm.

6. The method of claim 1, further comprising adjusting one or more of a position, the magnetic rotation plane, and a rotation frequency of the permanent magnet.

7. The method of claim 6, wherein said adjusting is performed in response to at least one characteristic of the total occlusion.

8. The method of claim 7, wherein the at least one characteristic is selected from the group consisting of: a location, a shape, a thickness, and a density of the total occlusion.

9. The method of claim 7, wherein the at least one characteristic is determined from one or more images of a region of the vessel in which the total occlusion is located.

10. The method of claim 1, wherein said orienting a permanent magnet is performed based on preoperative images of the vessel.

11. A method of facilitating treatment of a blockage within a vessel of a subject through external magnetomotive manipulation of magnetic particles, the method comprising:
administering a plurality of magnetic particles within vasculature of the subject,
positioning a magnet external to the vessel to establish a magnetic rotation plane of the magnet, wherein the magnet has a magnetic field and a directed magnetic gradient;
programming a controller to position and rotate the magnet in a manner sufficient to agglomerate the magnetic particles to form a plurality of agglomerations within the vasculature, wherein the agglomerations travel within the vasculature toward the blockage within the vessel in an end-over-end motion under influence of the magnetic field and the directed magnetic gradient of the magnet;
wherein the end-over-end motion of each of the agglomerations generates a stirring motion within the vessel proximal to the blockage, and
wherein the stirring motion facilitates contact of at least one of (i) an agent configured to facilitate visualization with an imaging modality or (ii) a drug configured to accelerate destruction of the blockage, by enhancing diffusion of the agent or the drug to a region of the blockage.

12. The method of claim 11:
wherein the magnet is a permanent magnet,
wherein the permanent magnet is rotatably coupled to a motor by a movable arm,
wherein the permanent magnet is configured to rotate about two different axes of rotation, and
wherein the particles comprises magnetite.

13. The method of claim 11, wherein the agent or the drug is attached to the magnetic particles prior to introducing the magnetic particles.

14. The method of claim 13, wherein the agent or the drug is coated on the magnetic particles.

15. The method of claim 11, wherein the agent or the drug is introduced within the vasculature separate from the magnetic particles.

16. The method of claim 11, wherein the magnet is rotatably coupled to a motor by a movable arm.

17. The method of claim 11, wherein the blockage comprises a total occlusion.

18. The method of claim 11, wherein the agglomerations comprise rotating rods.

19. The method of claim 11, wherein the agglomerations comprise spheres.

20. The method of claim 11, wherein the blockage comprises a partial blockage.

* * * * *

UNITED STATES PATENT AND TRADEMARK OFFICE
CERTIFICATE OF CORRECTION

PATENT NO. : 10,813,997 B2  
APPLICATION NO. : 16/032796  
DATED : October 27, 2020  
INVENTOR(S) : Francis M. Creighton Page 1 of 1

It is certified that error appears in the above-identified patent and that said Letters Patent is hereby corrected as shown below:

On the Title Page

Column 2, Item (56), Line 3, under Other Publications, delete "2006" and insert --2008--.

On Page 3, Column 1, Item (56), Line 21, under U.S. Patent Documents, delete "06/2010" and insert --08/2010--.

On Page 4, Column 2, Item (56), Line 20, under Other Publications, delete "227-243." and insert --227-243,--.

On Page 5, Column 1, Item (56), Line 1, under Other Publications, delete "Shyarn" and insert --Shyam--.

In the Specification

In Column 27, Line 10, delete "r" and insert --$\tau$--.

In Column 27, Line 44, delete "T" and insert --$\mu$--.

Signed and Sealed this  
Thirtieth Day of March, 2021

Drew Hirshfeld  
*Performing the Functions and Duties of the*  
*Under Secretary of Commerce for Intellectual Property and*  
*Director of the United States Patent and Trademark Office*